(12) United States Patent
Higashiura et al.

(10) Patent No.: US 7,939,552 B2
(45) Date of Patent: May 10, 2011

(54) BENZYLOXYPROPYLAMINE DERIVATIVE

(75) Inventors: Kunihiko Higashiura, Hyogo (JP); Takashi Ogino, Hyogo (JP); Kazuhito Furukawa, Hyogo (JP)

(73) Assignee: Nippon Zoki Pharmaceutical Co., Ltd., Osaka (JP)

( * ) Notice: Subject to any disclaimer, the term of this patent is extended or adjusted under 35 U.S.C. 154(b) by 178 days.

(21) Appl. No.: 11/887,072

(22) PCT Filed: Mar. 29, 2006

(86) PCT No.: PCT/JP2006/306451
§ 371 (c)(1),
(2), (4) Date: Feb. 25, 2008

(87) PCT Pub. No.: WO2006/106727
PCT Pub. Date: Oct. 12, 2006

(65) Prior Publication Data
US 2008/0262230 A1      Oct. 23, 2008

(30) Foreign Application Priority Data
Mar. 31, 2005   (JP) ................................ 2005-103326

(51) Int. Cl.
*A61K 31/445* (2006.01)
*A61K 31/165* (2006.01)
*A61K 31/44* (2006.01)
*C07D 213/81* (2006.01)
*C07D 211/30* (2006.01)
*C07D 211/82* (2006.01)
*C07C 233/00* (2006.01)

(52) U.S. Cl. ........ 514/354; 546/323; 546/225; 546/337; 564/185; 514/617; 514/330; 514/357

(58) Field of Classification Search ................. 546/323, 546/337, 225; 514/354, 330, 617, 357; 564/185
See application file for complete search history.

(56) References Cited

U.S. PATENT DOCUMENTS

| | | | |
|---|---|---|---|
| 5,472,978 A | 12/1995 | Baker et al. | |
| 6,441,237 B1 | 8/2002 | Stransky et al. | |
| 2003/0125557 A1 | 7/2003 | Jasserand et al. | |

FOREIGN PATENT DOCUMENTS

| | | |
|---|---|---|
| JP | A-06-509090 | 10/1994 |
| JP | A-2002-537282 | 11/2002 |
| JP | A-2003-113160 | 4/2003 |

OTHER PUBLICATIONS

Caplus Abstract 2000:592689, "Preparation of 3-phenoxy- and 3-phenylalkoxy-2-phenylpropylamines as inhibitors of the voltage-dependent sodium channel.", Stransky et. al, Aug. 24, 2000.*
C. Genicot et al., "Discovery of Orally Bioavailable $NK_1$ Receptor Antagonists," *Bioorganic & Medicinal Chemistry Letters*, vol. 13, Oct. 29, 2002, pp. 437-442.

* cited by examiner

*Primary Examiner* — Janet L Andres
*Assistant Examiner* — Heidi Reese
(74) *Attorney, Agent, or Firm* — Oliff & Berridge, PLC

(57) ABSTRACT

Disclosed is a novel benzyloxypropylamine derivative having an excellent tachykinin receptor antagonistic effect. This compound shows a good transfer into the blood and a long blood half-life in the blood kinetic test using a guinea pig orally administered with the compound and is stable in an animal plasma. The compound also shows a high transfer to the central nervous system when it is orally administered to a guinea pig at a certain dose. Accordingly, the benzyloxypropylamine derivative is quite useful as a novel anti-tachykinin agent.

20 Claims, 1 Drawing Sheet

BENZYLOXYPROPYLAMINE DERIVATIVE

TECHNICAL FIELD

The present invention relates to a novel benzyloxypropylamine derivative and a pharmaceutically acceptable salt and hydrate thereof and also relates to a pharmaceutical agent containing said compound as an effective ingredient.

BACKGROUND ART

Tachykinin is a general name for a group of peptides having similar structures and, in mammals, substance P(SP), neurokinin A (NKA) and neurokinin B (NKB) are representative ones. They are neuropeptides widely distributed in living bodies and the substance where the physiological function was most specifically studied is a substance P. The substance P is a peptide comprising 11 amino acids and showing hypotensive action, contracting action for smooth muscles, promoting action for secretion of saliva, exciting action for neurons, inducing action for pain reaction. It has been known to be related to various diseases such as digestive disease, neulogic disease, respiratory disease, and has been suggested to deeply participate particularly in inflammation, allergy, carcinoid syndrome, chronic pain, headache, Crohn's disease, depression, nausea, etc. Accordingly, an antagonist to tachykinin such as the substance P is useful as pharmaceuticals such as an anti-inflammatory agent, an agent for allergic diseases, an analgesic, an antiemetic, an agent for irritable bowel syndrome, an agent for skin diseases, an agent for vasospastic diseases, an agent for cerebral ischemic diseases, an antidepressant, an antianxiety agent, an agent for autoimmune diseases, a muscle relaxant and an antispasmodic.

Various anti-tachykinin compounds have been developed and reported with a purpose of developing the therapeutic agents for the above mentioned diseases in which tachykinin participates. However, there are problems in their pharmacokinetics such as a undesirable transfer into the blood and their safety whereby anti-tachykinin compounds having novel structures have been demanded. For example, in the Non-Patent Document 1, benzyloxyphenethylpiperazine derivatives in which a partial structure thereof is similar to the structure of the compounds of the present invention are reported. However they are the compounds having a clearly different structure from the benzyloxypropylamine derivatives of the present invention which are linear molecule without piperazine skeleton.

Non-Patent Document 1: Bioorganic & Medicinal Chemistry Letters, vol. 13, pages 437 to 442 (2003)

DISCLOSURE OF THE INVENTION

An object of the present invention is to provide a novel compound which is useful as an anti-tachykinin agent having an excellent pharmacokinetics.

The present inventors have carried out intensive studies for benzyloxypropylamine derivatives and, as a result, they have found that a novel 2-phenylbenzyloxypropylamine derivative represented by the following formula (I) has an excellent anti-substance P action and is useful as a pharmaceutical agent, whereupon they have achieved the present invention.

The benzyloxypropylamine derivative of the present invention is a strong antagonist to tachykinin receptors having a novel structure. It exhibits a preferred pharmacokinetic property of a good transfer into the blood, a long half-life period in the blood and an excellent transfer into the central nervous system (CNS) in a pharmacokinetic test in the blood and a test for transfer into the CNS by oral administration to guinea pigs, whereby it has a desirable utility as a pharmaceutical agent.

BEST MODE FOR CARRYING OUT THE INVENTION

Figure 1:
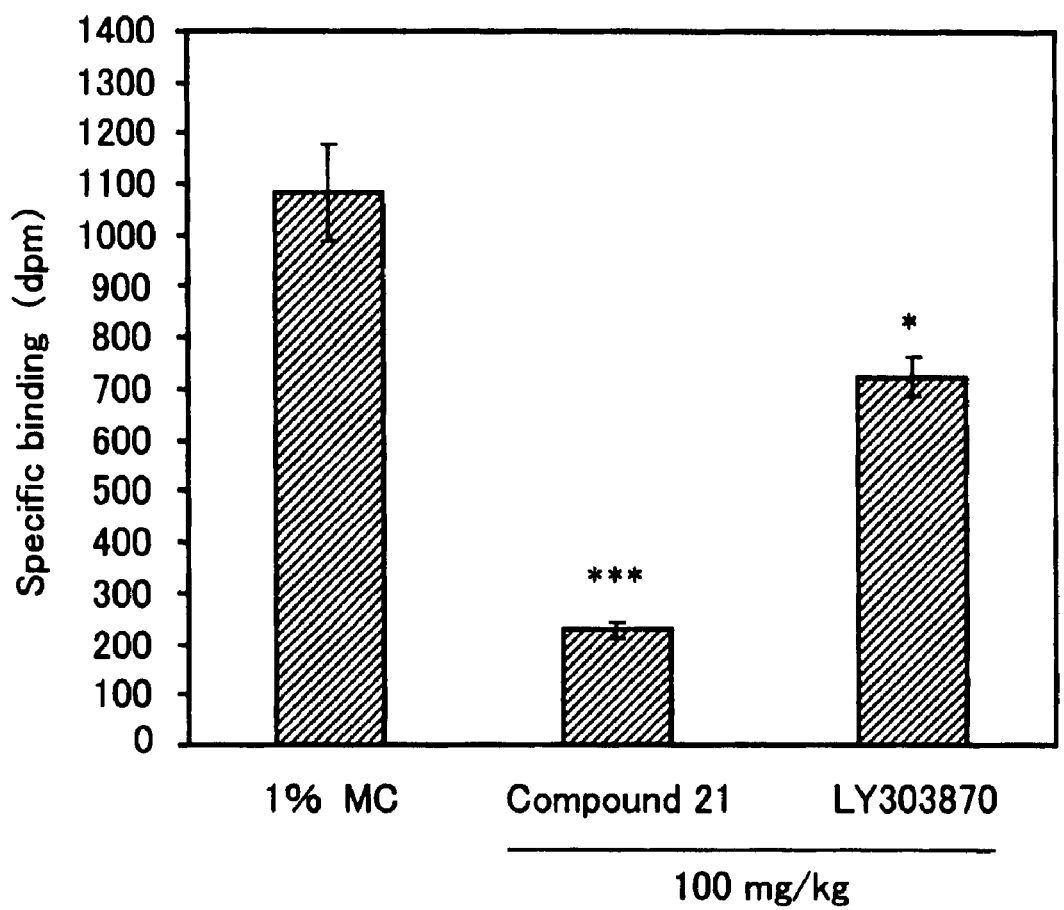
FIG. 1 is an example of the result which shows the transfer of the compound of the present invention into the CNS when it is orally administered to guinea pigs.

The present invention relates to a novel benzyloxypropylamine derivative represented by the following formula (I) and a pharmaceutically acceptable salt or hydrate thereof and also relates to a pharmaceutical agent such as an anti-tachykinin agent containing said compound as an effective ingredient.

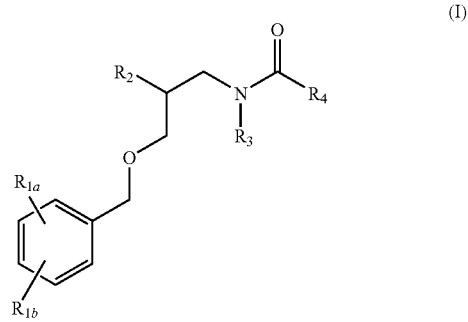

[In the formula, $R_{1a}$ and $R_{1b}$, which may be the same or different, is hydrogen, halogen, $C_{1-4}$ alkyl or trifluoromethyl; $R_2$ is phenyl which may be optionally substituted with halogen or diphenylmethyl; $R_3$ is hydrogen, $C_{1-4}$ alkyl or acetoxymethyl; and $R_4$ is a substituent selected from the following (a) to (j):

(a) piperidinyl which may be optionally substituted with $C_{1-4}$ alkyl, piperidinyl, carboxymethyl, tert-butoxycarbonyl, tert-butoxycarbonylmethyl or amino, (b) piperidinylamino which may be optionally substituted with tert-butoxycarbonyl, (c) piperidinylmethyl which may be optionally substituted with carboxy or tert-butoxycarbonyl, (d) pyridyl which may be optionally substituted with one or two group(s) selected from $C_{1-4}$ alkyl, $C_{1-4}$ alkoxy, halogen, hydroxy, oxy, amino, carboxy and benzyl, (e) $C_{1-4}$ alkyl which is substituted with pyridyl, oxypyridyl, carboxy, amino or tert-butoxycarbonylamino, (f) $C_{2-4}$ alkenyl which is substituted with pyridyl or oxypyridyl, (g) phenyl which may be optionally substituted with a group selected from hydroxy, carboxy, ethoxycarbonyl, halogen, $C_{1-4}$ alkyl which may be optionally substituted with piperidinyl, pyrrolidinyl, amino, halogen or tert-butoxycarbonylamino and amino which may be optionally substituted with one or two $C_{1-4}$ alkyl or tert-butoycarbonyl, (h) cyclohexyl which may be substituted with amino or tert-butoxycarbonylamino, (i) pyrazinyl and (j) quinolyl.]

In the substituent for the above formula (I), $C_{1-4}$ alkyl is preferably a linear or branched alkyl group such as methyl, ethyl, propyl, isopropyl, butyl, isobutyl, sec-butyl and tert-butyl.

C$_{1-4}$ Alkoxy is preferably a linear or branched alkoxy group such as methoxy, ethoxy, propyloxy, isopropyloxy and butyloxy.

C$_{2-4}$ Alkenyl is preferably a linear or branched alkenyl group such as vinyl, allyl, propenyl, isopropenyl, 1-butenyl and 2-butenyl.

Preferred compounds of the present invention are given as follows.

N-[3-(3,5-Bis(trifluoromethyl)benzyloxy)-2-phenylpropyl]-1-methylpiperidine-4-carboxamide [Compound 1]
N-[3-(3,5-Bis(trifluoromethyl)benzyloxy)-2-(4-fluorophenyl)propyl]-1-methylpiperidine-4-carboxamide hydrochloride [Compound 2]
N-[3-(3,5-Bis(trifluoromethyl)benzyloxy)-2-phenylpropyl]-1-isopropyl piperidine-4-carboxamide [Compound 3]
N-[3-(3,5-Bis(trifluoromethyl)benzyloxy)-2-phenylpropyl] piperidine-4-carboxamide hydrochloride [Compound 4]
N-[3-(3,5-Bis(trifluoromethyl)benzyloxy)-2-(4-fluorophenyl)propyl]piperidine-4-carboxamide hydrochloride [Compound 5]
N-[3-(3,5-Bis(trifluoromethyl)benzyloxy)-2-phenylpropyl] isonicotinamide [Compound 6]
N-[3-(3,5-Bis(trifluoromethyl)benzyloxy)-2-(4-fluorophenyl)propyl]isonicotinamide [Compound 7]
N-[3-(3,5-Bis(trifluoromethyl)benzyloxy)-2-phenylpropyl] nicotinamide [Compound 8]
N-[3-(3,5-Bis(trifluoromethyl)benzyloxy)-2-(4-fluorophenyl)propyl]nicotinamide [Compound 9]
N-[3-(3,5-Bis(trifluoromethyl)benzyloxy)-2-(4-fluorophenyl)propyl]pyridine-2-carboxamide [Compound 10]
N-[3-(3,5-Bis(trifluoromethyl)benzyloxy)-2-phenylpropyl]-2-chloroisonicotinamide [Compound 11]
N-[3-(3,5-Bis(trifluoromethyl)benzyloxy)-2-(4-fluorophenyl)propyl]-2-hydroxyisonicotinamide [Compound 12]
N-[3-(3,5-Bis(trifluoromethyl)benzyloxy)-2-phenylpropyl]-6-methylnicotinamide [Compound 13]
N-[3-(3,5-Bis(trifluoromethyl)benzyloxy)-2-phenylpropyl]-2-chloro-6-methylnicotinamide [Compound 14]
N-[3-(3,5-Bis(trifluoromethyl)benzyloxy)-2-phenylpropyl]-2,6-dichloronicotinamide [Compound 15]
N-[3-(3,5-Bis(trifluoromethyl)benzyloxy)-2-phenylpropyl]-2,6-dichloro-5-fluoronicotinamide [Compound 16]
N-[3-(3,5-Bis(trifluoromethyl)benzyloxy)-2-phenylpropyl]-2,6-dimethoxynicotinamide [Compound 17]
N-[3-(3,5-Bis(trifluoromethyl)benzyloxy)-2-phenylpropyl] quinoline-4-carboxamide [Compound 18]
N-[3-(3,5-Bis(trifluoromethyl)benzyloxy)-2-(4-fluorophenyl)propyl]quinoline-4-carboxamide [Compound 19]
N-[3-(3,5-Bis(trifluoromethyl)benzyloxy)-2-phenylpropyl]-1-oxyisonicotinamide [Compound 20]
N-[3-(3,5-Bis(trifluoromethyl)benzyloxy)-2-(4-fluorophenyl)propyl]-1-oxyisonicotinamide [Compound 21]
N-[3-(3,5-Bis(trifluoromethyl)benzyloxy)-2-phenylpropyl]-1-oxynicotinamide [Compound 22]
N-[3-(3,5-Bis(trifluoromethyl)benzyloxy)-2-(4-fluorophenyl)propyl]-1-oxynicotinamide [Compound 23]
N-[3-(3,5-Bis(trifluoromethyl)benzyloxy)-2-phenylpropyl]-1-oxypyridine-2-carboxamide [Compound 24]
N-[3-(3,5-Bis(trifluoromethyl)benzyloxy)-2-(4-fluorophenyl)propyl]-1-oxypyridine-2-carboxamide [Compound 25]
4-[3-(3,5-Bis(trifluoromethyl)benzyloxy)-2-phenylpropylcarbamoyl]-1-methylpyridinium iodide [Compound 26]
4-[3-(3,5-Bis(trifluoromethyl)benzyloxy)-2-(4-fluorophenyl)propylcarbamoyl]-1-methylpyridinium iodide [Compound 27]
3-[3-(3,5-Bis(trifluoromethyl)benzyloxy)-2-phenylpropylcarbamoyl]-1-methylpyridinium iodide [Compound 28]
3-[3-(3,5-Bis(trifluoromethyl)benzyloxy)-2-(4-fluorophenyl)propylcarbamoyl]-1-methylpyridinium iodide [Compound 29]
1-Benzyl-4-[3-(3,5-bis(trifluoromethyl)benzyloxy)-2-phenylpropylcarbamoyl]pyridinium chloride [Compound 30]
1-Benzyl-4-[3-(3,5-bis(trifluoromethyl)benzyloxy)-2-(4-fluorophenyl)propylcarbamoyl]pyridinium chloride [Compound 31]
1-Benzyl-3-[3-(3,5-bis(trifluoromethyl)benzyloxy)-2-phenylpropylcarbamoyl]pyridinium chloride [Compound 32]
N-[3-(3,5-Bis(trifluoromethyl)benzyloxy)-2-phenylpropyl]-2-pyridin-4-ylacetamide [Compound 33]
N-[3-(3,5-Bis(trifluoromethyl)benzyloxy)-2-(4-fluorophenyl)propyl]-2-pyridin-4-ylacetamide [Compound 34]
N-[3-(3,5-Bis(trifluoromethyl)benzyloxy)-2-phenylpropyl]-2-pyridin-3-ylacetamide [Compound 35]
N-[3-(3,5-Bis(trifluoromethyl)benzyloxy)-2-(4-fluorophenyl)propyl]-2-pyridin-3-ylacetamide [Compound 36]
N-[3-(3,5-Bis(trifluoromethyl)benzyloxy)-2-phenylpropyl]-2-pyridin-2-ylacetamide [Compound 37]
N-[3-(3,5-Bis(trifluoromethyl)benzyloxy)-2-(4-fluorophenyl)propyl]-2-pyridin-2-ylacetamide [Compound 38]
N-[3-(3,5-Bis(trifluoromethyl)benzyloxy)-2-phenylpropyl]-2-(1-oxypyridin-4-yl)acetamide [Compound 39]
N-[3-(3,5-Bis(trifluoromethyl)benzyloxy)-2-(4-fluorophenyl)propyl]-2-(1-oxypyridin-4-yl)acetamide [Compound 40]
N-[3-(3,5-Bis(trifluoromethyl)benzyloxy)-2-phenylpropyl]-2-(1-oxypyridin-3-yl)acetamide [Compound 41]
N-[3-(3,5-Bis(trifluoromethyl)benzyloxy)-2-(4-fluorophenyl)propyl]-2-(1-oxypyridin-3-yl)acetamide [Compound 42]
N-[3-(3,5-Bis(trifluoromethyl)benzyloxy)-2-phenylpropyl]-2-(1-oxypyridin-2-yl)acetamide [Compound 43]
N-[3-(3,5-Bis(trifluoromethyl)benzyloxy)-2-(4-fluorophenyl)propyl]-2-(1-oxypyridin-2-yl)acetamide [Compound 44]
N-[3-(3,5-Bis(trifluoromethyl)benzyloxy)-2-phenylpropyl]-3-pyridin-4-ylacrylamide [Compound 45]
N-[3-(3,5-Bis(trifluoromethyl)benzyloxy)-2-phenylpropyl]-3-pyridin-3-ylacrylamide [Compound 46]
N-[3-(3,5-Bis(trifluoromethyl)benzyloxy)-2-(4-fluorophenyl)propyl]-3-pyridin-3-ylacrylamide [Compound 47]
N-[3-(3,5-Bis(trifluoromethyl)benzyloxy)-2-phenylpropyl]-3-pyridin-4-ylpropionamide [Compound 48]
N-[3-(3,5-Bis(trifluoromethyl)benzyloxy)-2-phenylpropyl]-3-pyridin-3-ylpropionamide [Compound 49]
N-[3-(3,5-Bis(trifluoromethyl)benzyloxy)-2-(4-fluorophenyl)propyl]-3-pyridin-3-ylpropionamide [Compound 50]
N-[3-(3,5-Bis(trifluoromethyl)benzyloxy)-2-phenylpropyl]-3-(1-oxypyridin-4-yl)propionamide [Compound 51]
N-[3-(3,5-Bis(trifluoromethyl)benzyloxy)-2-phenylpropyl]-3-(1-oxypyridin-3-yl)propionamide [Compound 52]
N-[3-(3,5-Bis(trifluoromethyl)benzyloxy)-2-phenylpropyl]-3-(1-oxypyridin-4-yl)acrylamide [Compound 53]
N-[3-(3,5-Bis(trifluoromethyl)benzyloxy)-2-phenylpropyl]-3-(1-oxypyridin-3-yl)acrylamide [Compound 54]
N-[3-(3,5-Bis(trifluoromethyl)benzyloxy)-2-(4-fluorophenyl)propyl]-3-(1-oxypyridin-3-yl)acrylamide [Compound 55]
N-[3-(3,5-Bis(trifluoromethyl)benzyloxy)-2-phenylpropyl]-4-hydroxybenzamide [Compound 56]
N-[3-(3,5-Bis(trifluoromethyl)benzyloxy)-2-phenylpropyl]-4-fluorobenzamide [Compound 57]

N-[3-(3,5-Bis(trifluoromethyl)benzyloxy)-2-phenylpropyl]-4-dimethyl aminobenzamide [Compound 58]
N-[3-(3,5-Bis(trifluoromethyl)benzyloxy)-2-phenylpropyl]-4-diethylaminobenzamide hydrochloride [Compound 59]
N-[3-(3,5-Bis(trifluoromethyl)benzyloxy)-2-phenylpropyl] terephthalamic acid [Compound 60]
4-Amino-N-[3-(3,5-bis(trifluoromethyl)benzyloxy)-2-phenylpropyl]benzamide hydrochloride [Compound 61]
4-Amino-N-[3-(3,5-Bis(trifluoromethyl)benzyloxy)-2-(4-fluorophenyl) propyl]benzamide hydrochloride [Compound 62]
4-Aminomethyl-N-[3-(3,5-Bis(trifluoromethyl)benzyloxy)-2-phenylpropyl]benzamide hydrochloride [Compound 63]
N-[3-(3,5-Bis(trifluoromethyl)benzyloxy)-2-phenylpropyl]-4-pyrrolidin-1-ylmethylbenzamide hydrochloride [Compound 64]
N-[3-(3,5-Bis(trifluoromethyl)benzyloxy)-2-phenylpropyl]-4-piperidin-1-ylmethylbenzamide hydrochloride [Compound 65]
Ethyl N-[3-(3,5-bis(trifluoromethyl)benzyloxy)-2-phenylpropyl]terephthalamate [Compound 66]
tert-Butyl {4-[3-(3,5-bis(trifluoromethyl)benzyloxy)-2-phenylpropylcarbamoyl]phenyl}carbamate [Compound 67]
tert-Butyl {4-[3-(3,5-bis(trifluoromethyl)benzyloxy)-2-(4-fluorophenyl)propylcarbamoyl]phenyl}carbamate [Compound 68]
tert-Butyl {4-[3-(3,5-bis(trifluoromethyl)benzyloxy)-2-phenylpropylcarbamoyl]benzyl}carbamate [Compound 69]
N-[3-(3,5-Bis(trifluoromethyl)benzyloxy)-2-phenylpropyl]-4-chloromethylbenzamide [Compound 70]
tert-Butyl 4-[3-(3,5-bis(trifluoromethyl)benzyloxy)-2-phenylpropylcarbamoyl]piperidine-1-carboxylate [Compound 71]
tert-Butyl 4-[3-(3,5-bis(trifluoromethyl)benzyloxy)-2-(4-fluorophenyl) propylcarbamoyl]piperidine-1-carboxylate [Compound 72]
tert-Butyl N-{2-[3-(3,5-bis(trifluoromethyl)benzyloxy)-2-phenylpropylcarbamoyl]ethyl}carbamate [Compound 73]
3-Amino-N-[3-(3,5-bis(trifluoromethyl)benzyloxy)-2-phenylpropyl]propionamide hydrochloride [Compound 74]
tert-Butyl N-{2-[3-(3,5-bis(trifluoromethyl)benzyloxy)-2-(4-fluorophenyl)propylcarbamoyl]ethyl}carbamate [Compound 75]
3-Amino-N-[3-(3,5-bis(trifluoromethyl)benzyloxy)-2-(4-fluorophenyl)propyl]propionamide hydrochloride [Compound 76]
tert-Butyl {4-[3-(3,5-bis(trifluoromethyl)benzyloxy)-2-phenylpropylcarbamoyl]butyl}carbamate [Compound 77]
N-[3-(3,5-Bis(trifluoromethyl)benzyloxy)-2-phenylpropyl]-5-aminopentanoicamide hydrochloride [Compound 78]
tert-Butyl {4-[3-(3,5-bis(trifluoromethyl)benzyloxy)-2-phenylpropylcarbamoyl]piperidin-1-yl}acetate [Compound 79]
{4-[3-(3,5-Bis(trifluoromethyl)benzyloxy)-2-phenylpropylcarbamoyl]piperidin-1-yl}acetic acid hydrochloride [Compound 80]
Ethyl N-[3-(3,5-bis(trifluoromethyl)benzyloxy)-2-phenylpropyl]malonamate [Compound 81]
N-[3-(3,5-Bis(trifluoromethyl)benzyloxy)-2-phenylpropyl] malonamic acid [Compound 82]
N-[3-(3,5-Bis(trifluoromethyl)benzyloxy)-2-phenylpropyl] pyrazine-2-carboxamide [Compound 83]
Phenyl [3-(3,5-bis(trifluoromethyl)benzyloxy)-2-phenylpropyl]carbamate [Compound 84]
tert-Butyl 4-{3-[3-(3,5-bis(trifluoromethyl)benzyloxy)-2-phenylpropyl]ureido}piperidine-1-carboxylate [Compound 85]
1-[3-(3,5-Bis(trifluoromethyl)benzyloxy)-2-phenylpropyl]-3-piperidin-4-ylurea hydrochloride [Compound 86]
tert-Butyl {4-[3-(3,5-bis(trifluoromethyl)benzyloxy)-2-phenylpropylcarbamoyl]cyclohexyl}carbamate [Compound 87]
4-Aminocyclohexanecarboxylic acid [3-(3,5-bis(trifluoromethyl)benzyloxy)-2-phenylpropyl]amide hydrochloride [Compound 88]
Ethyl 1-{[3-(3,5-bis(trifluoromethyl)benzyloxy)-2-phenylpropylcarbamoyl]methyl}piperidine-4-carboxyate [Compound 89]
1-{[3-(3,5-Bis(trifluoromethyl)benzyloxy)-2-phenylpropylcarbamoyl]methyl}piperidine-4-carboxylic acid [Compound 90]
N-[3-(3,5-Bis(trifluoromethyl)benzyloxy)-2-phenylpropyl]-2-[1,4']bipiperidinyl-1'-ylacetamide dihydrochloride [Compound 91]
tert-Butyl 4-{[3-(3,5-bis(trifluoromethyl)benzyloxy)-2-phenylpropyl]methylcarbamoyl}piperidine-1-carboxylate [Compound 92]
N-[3-(3,5-Bis(trifluoromethyl)benzyloxy)-2-phenylpropyl]-N-methylpiperidine-4-carboxamide hydrochloride [Compound 93]
tert-Butyl 4-{[3-(3,5-bis(trifluoromethyl)benzyloxy)-2-(4-fluorophenyl)propyl]methylcarbamoyl}piperidine-1-carboxylat [Compound 94]
N-[3-(3,5-Bis(trifluoromethyl)benzyloxy)-2-(4-fluorophenyl)propyl]-N-methylpiperidine-4-carboxamide hydrochloride [Compound 95]
N-[3-(3,5-Bis(trifluoromethyl)benzyloxy)-2-phenylpropyl]-N-methyl-1-methylpiperidine-4-carboxamide hydrochloride [Compound 96]
N-[3-(3,5-Bis(trifluoromethyl)benzyloxy)-2-(4-fluorophenyl)propyl]-N-methylpiperidine-4-carboxamide hydrochloride [Compound 97]
N-[3-(3,5-Bis(trifluoromethyl)benzyloxy)-2-(4-fluorophenyl)propyl]-N-methylisonicotinamide [Compound 98]
N-[3-(3,5-Bis(trifluoromethyl)benzyloxy)-2-phenylpropyl]-N-methyl-1-oxyisonicotinamide [Compound 99]
N-[3-(3,5-Bis(trifluoromethyl)benzyloxy)-2-(4-fluorophenyl)propyl]-2-hydroxy-N-methylisonicotinamide [Compound 100]
tert-Butyl N-(2-{[3-(3,5-bis(trifluoromethyl)benzyloxy)-2-phenylpropyl]methylcarbamoyl}ethyl)carbamate [Compound 101]
N-[3-(3,5-Bis(trifluoromethyl)benzyloxy)-2-phenylpropyl]-N-methyl-3-aminopropionamide hydrochloride [Compound 102]
tert-Butyl (2-{[3-(3,5-bis(trifluoromethyl)benzyloxy)-2-(4-fluorophenyl)propyl]methylcarbamoyl}ethyl)carbamate [Compound 103]
3-Amino-N-[3-(3,5-bis(trifluoromethyl)benzyloxy)-2-(4-fluorophenyl)propyl]-N-methylpropionamide hydrochloride [Compound 104]
tert-Butyl (4-{[3-(3,5-bis(trifluoromethyl)benzyloxy)-2-phenylpropyl]methylcarbamoyl}butyl)carbamate [Compound 105]
5-Aminopentanoic acid [3-(3,5-bis(trifluoromethyl)benzyloxy)-2-phenylpropyl]methylamide hydrochloride [Compound 106]
1-Methylpiperidine-4-carboxylic acid [2-(3,5-bis(trifluoromethyl)benzyloxymethyl)-3,3-diphenylpropyl]methylamide hydrochloride [Compound 107]
tert-Butyl 4-[3-(3,5-dimethylbenzyloxy)-2-phenylpropylcarbamoyl]piperidine-1-carboxylate [Compound 108]
Piperidine-4-carboxylic acid [3-(3,5-dimethylbenzyloxy)-2-phenylpropyl]amide hydrochloride [Compound 109]

1-Methylpiperidine-4-carboxylic acid [3-(3,5-dimethylbenzyloxy)-2-phenylpropyl]amide [Compound 110]
tert-Butyl {2-[3-(3,5-dimethylbenzyloxy)-2-phenylpropylcarbamoyl]ethyl}carbamate [Compound 111]
3-Amino-N-[3-(3,5-dimethylbenzyloxy)-2-phenylpropyl] propionamide hydrochloride [Compound 112]
tert-Butyl 4-[3-(4-fluorobenzyloxy)-2-phenylpropylcarbamoyl]piperidine-1-carboxylate [Compound 113]
Piperidine-4-carboxylic acid [3-(4-fluorobenzyloxy)-2-phenylpropyl]amide hydrochloride [Compound 114]
1-Methylpiperidine-4-carboxylic acid [3-(4-fluorobenzyloxy)-2-phenylpropyl]amide hydrochloride [Compound 115]
N-[3-(4-Fluorobenzyloxy)-2-phenylpropyl]isonicotinamide [Compound 116]
N-[3-(4-Fluorobenzyloxy)-2-phenylpropyl]-1-oxyisonicotinamide [Compound 117]
tert-Butyl {2-[3-(4-fluorobenzyloxy)-2-phenylpropylcarbamoyl]ethyl}carbamte [Compound 118]
3-Amino-N-[3-(4-fluorobenzyloxy)-2-phenylpropyl]propionamide hydrochloride [Compound 119]
N-[3-(3,4-Dichlorobenzyloxy)-2-phenylpropyl]-1-oxyisonicotinamide [Compound 120]
tert-Butyl {4-[3-(3,4-dichlorobenzyloxy)-2-phenylpropylcarbamoyl]ph enyl}carbamate [Compound 121]
4-Amino-N-[3-(3,4-dichlorobenzyloxy)-2-phenylpropyl] benzamide hydrochloride [Compound 122]
N-[3-(3,5-Difluorobenzyloxy)-2-phenylpropyl]-1-oxyisonicotinamide [Compound 123]
1-Oxy-N-[2-phenyl-3-(3-trifluoromethylbenzyloxy)propyl] isonicotinamide [Compound 124]
N-(3-Benzyloxy-2-phenylpropyl)-1-oxyisonicotinamide [Compound 1 25]

Preferred embodiments of the present invention are as follows.

(1) A benzyloxypropylamine derivative represented by the above formula (I) and a pharmaceutically acceptable salt and hydrate thereof.

(2) The benzyloxypropylamine derivative according to the above (1), wherein $R_1$ is 3,5-bistrifluoromethyl group.

(3) The benzyloxypropylamine derivative according to the above (2), wherein $R_2$ is phenyl.

(4) The benzyloxypropylamine derivative according to the above (2), wherein $R_2$ is fluorophenyl.

(5) The benzyloxypropylamine derivative according to the above (3) or (4), wherein $R_3$ is hydrogen.

(6) The benzyloxypropylamine derivative according to the above (3) or (4), wherein $R_3$ is methyl.

(7) N-[3-(3,5-bis(trifluoromethyl)benzyloxy)-2-(4-fluorophenyl)propyl]-1-oxyisonicotinic acid amide and a pharmaceutically acceptable salt and hydrate thereof.

(8) A pharmaceutical agent which contains the benzyloxypropylamine derivative mentioned in the above (1) to (7) as an effective ingredient.

(9) The pharmaceutical agent according to the above (8), wherein it is an anti-inflammatory agent, an agent for allergic diseases, an analgesic, an antiemetic, an agent for irritable bowel syndrome, an agent for skin diseases, an agent for vasospastic diseases, an agent for cerebral ischemic diseases, an antidepressant, an anti-anxiety agent, an agent for autoimmune diseases, a muscle relaxant or an antispasmodic.

(10) The pharmaceutical agent according to the above (9), wherein it is an antiemetic.

Hereinafter, a general process for the production of the compound will be shown. The compound of the present invention represented by the above formula (I) may be generally produced by the following manner. Incidentally, in the following structural formulae, both $R_{1a}$ and $R_{1b}$ in the above formula (I) will be simply expressed as $R_1$.

The compound of the formula (I) is able to be produced by amidation of the compound of the formula (II). For example, the compound of the formula (I) is able to be produced from the compound of the formula (II) and an appropriate carboxylic acid compound by means of a common amidation process such as a mixed anhydride method, an active ester method or a method using a condensing agent such as DCC (1,3-dicyclohexyl carbodiimide) or WSC (water-soluble carbodiimide)-HCl in the presence of an appropriate base such as triethylamine and N-methylmorpholine. The reaction is able to be conducted in an appropriate solvent such as DMF (dimethylformamide), methylene chloride ($CH_2Cl_2$), chloroform ($CHCl_3$), THF (tetrahydrofuran), acetonitrile, water, acetone or a mixture thereof at appropriate temperature between under cooling with ice and boiling point of the solvent. In some cases, the resulting amide derivative itself is the final amide compound and, in other cases, it may be also subjected to an appropriate chemical conversion such as deprotection to give the final amide compound.

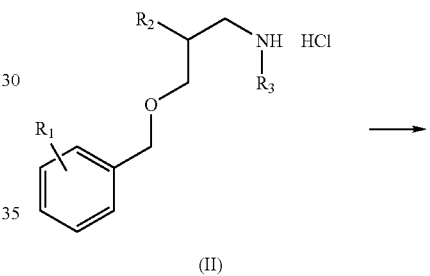

(II)

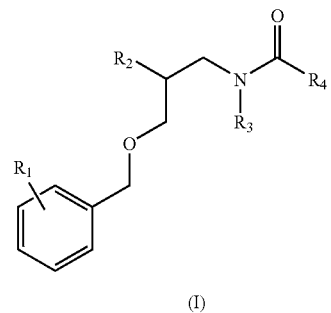

(I)

The compound of the formula (II) is able to be synthesized by subjecting the compound of the formula (III) to the reaction of removal of Boc. As to a reagent for removal of Boc, a solution of hydrogen chloride in an appropriate solvent such as dioxane, ethyl acetate, ether, methylene chloride or acetic acid, trifluoroacetic acid, formic acid, a solution of hydrogen bromide in acetic acid, etc. may be used. The reaction is able to be carried out using each of those reagents either solely or in an appropriate solvent such as dioxane, ethyl acetate, ether, methylene chloride or acetic acid at appropriate temperature between −20° C. and boiling point of the solvent.

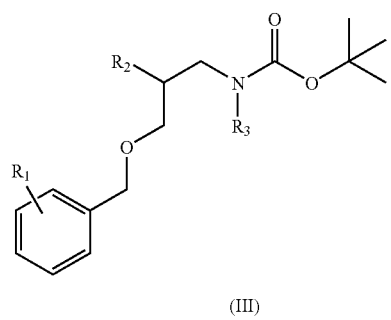

(III)

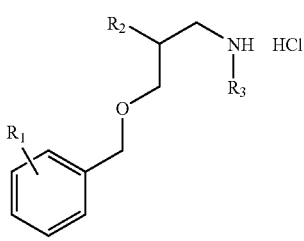

(II)

The compound of the formula (III) is able to be prepared by heating a compound of the formula (IV) with DPPA (diphenylphosphoryl acid azide) in tert-butanol in the presence of an appropriate base such as triethylamine or N-methylmorpholine. The substituent $R_3$ in the compound of the formula (III) obtained this far in the process is hydrogen and, when it is treated with a base such as sodium hydroxide, potassium hydroxide or sodium amide preferably in a polar aprotic solvent such as DMF or THF followed by being made to react with an alkylating agent such as alkyl halide or alkyl sulfate, a compound of the formula (III) where $R_3$ is an alkyl group is able to be prepared. This alkylating reaction is able to be conducted at appropriate temperature between under cooling with ice and boiling point of the solvent.

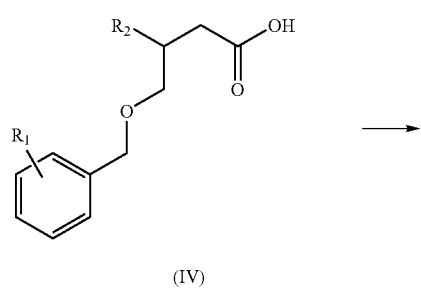

(IV)

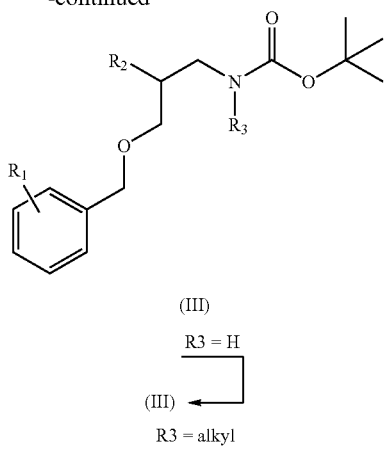

(III)
R3 = H (III) ←
R3 = alkyl

The compound of the formula (IV) is able to be produced by a hydrolyzing reaction of the compound of the formula (V). The hydrolyzing reaction is able to be carried out preferably by mixing with an aqueous solution of an appropriate base such as sodium hydroxide, potassium hydroxide, lithium hydroxide or potassium carbonate in a water-miscible solvent such as methanol, ethanol, acetone, dioxane or THF at appropriate temperature between under cooling with ice and boiling point of the solvent.

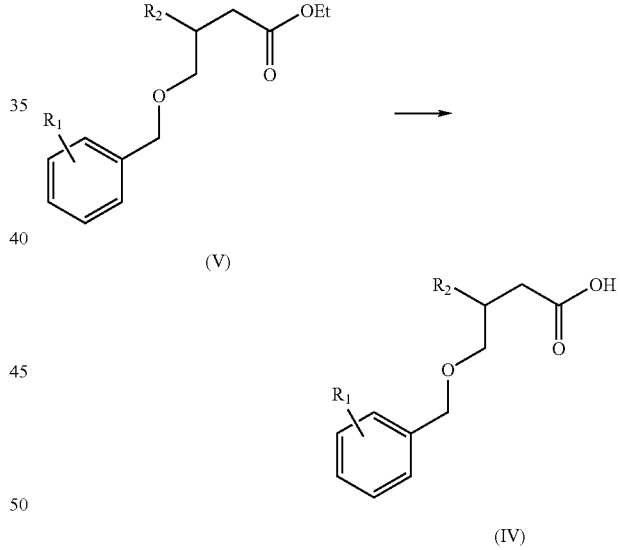

(V)

(IV)

The compound of the formula (V) is able to be produced by a reducing reaction of the compound of the formula (VI). The reducing reaction is able to be carried out by a catalytic reduction using noble metal catalyst or by using a combination of a transition metal salt with sodium borohydride. In the case of a catalytic reduction, it is able to be carried out using a noble metal catalyst such as palladium on carbon, palladium hydroxide on carbon, platinum oxide or Raney nickel in appropriate solvent such as ethanol, methanol, water, acetic acid, formic acid, ethyl acetate, THF, DMF or a mixture thereof in a hydrogen atmosphere of ordinary pressure, medium pressure or high pressure at appropriate temperature between room temperature and boiling point of the solvent. When sodium borohydride is used, the reaction is able to be carried out using a transition metal salt such as nickel chloride, cobalt chloride or iron chloride in a protic solvent such as ethanol, methanol or water either solely or as a mixture thereof with an aprotic solvent such as THF, DMF or dioxane at appropriate temperature between room temperature and boiling point of the solvent.

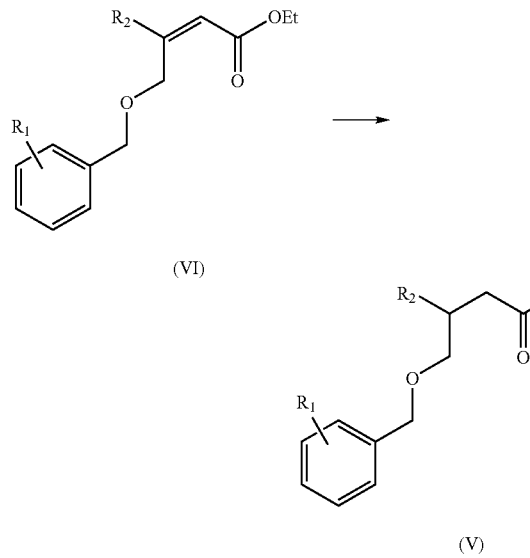

The compound of the formula (VI) is able to be produced by the so-called Wittig reaction of the compound of the formula (VII). For example, it is able to be produced by treating ethyl (diethoxyphosphoryl)acetate with a base such as sodium hydroxide, potassium hydroxide, sodium ethoxide, sodium methoxide, potassium tert-butoxide or sodium amide in an appropriate solvent such as THF or DMF followed by subjecting to a reaction with the compound of the formula (VII) at appropriate temperature between room temperature and boiling point of the solvent.

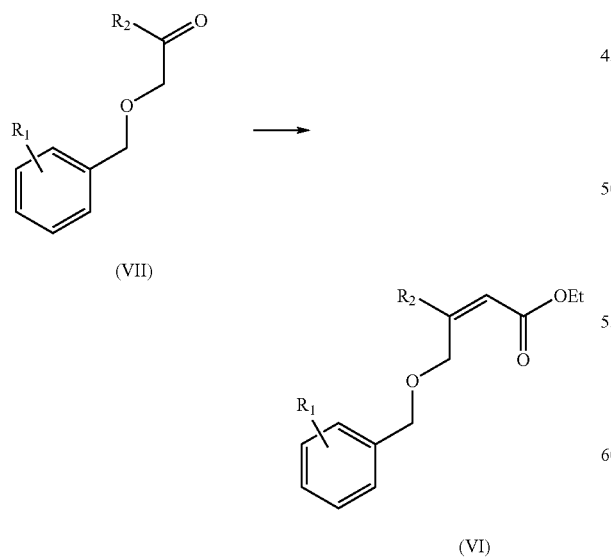

The compound of the formula (VII) is able to be produced by hydrolysis of the compound of the formula (VIII). This reaction is able to be carried out by treating with an acid such as hydrochloric acid, sulfuric acid, nitric acid, p-toluenesulfonic acid, methanesulfonic acid, trifluoroacetic acid, trifluoromethanesulfonic acid, acetic acid or formic acid in a solvent such as ethanol, methanol, dioxan, THF, acetic acid or a mixture thereof at appropriate temperature between room temperature and boiling point of the solvent.

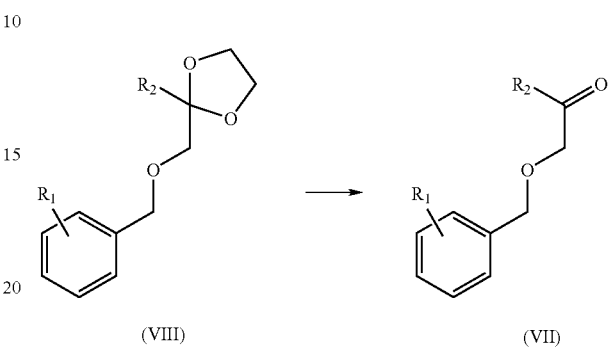

The compound of the formula (VIII) is produced by etherification of the compound of the formula (IX). It is conducted in such a manner that the compound of the formula (IX) is treated with a base such as sodium hydroxide, potassium hydroxide, sodium amide, sodium ethoxide or sodium methoxide in an aprotic solvent such as THF, DMF, toluene, benzene, acetone, dioxane or ether either solely or as a mixture thereof at appropriate temperature between −20° C. and boiling point of the solvent followed by being made to react with a benzyl etherifying agent. As to a benzylating agent, there may be used benzyl chloride, benzyl bromide, benzyl iodide, benzyl alcohol methanesulfonate, benzyl alcohol p-toluenesulfonate or benzyl alcohol trifluoromethanesulfonate having or not having an appropriate substituent on the benzene ring. The reaction may be conducted at appropriate temperature between −20° C. and boiling point of the solvent.

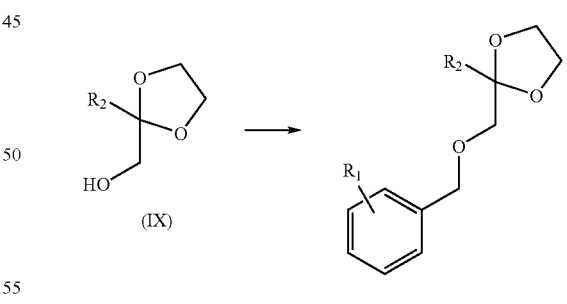

The compound of the formula (IX) is able to be synthesized by a dehydration of the compound of the formula (X) with ethylene glycol. The reaction is able to be conducted by subjecting the compound of the formula (X) to the reaction of in a solvent such as benzene, toluene, xylene, chloroform or carbon tetrachloride using a catalyst such as p-toluenesulfonic acid, methanesulfonic acid, sulfuric acid or benzenesulfonic acid.

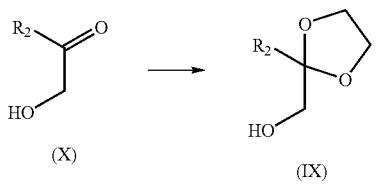

The compounds represented by the above-given formula (I) include the pharmaceutically acceptable salts of thereof such as acid addition salts with hydrochloric acid, sulfuric acid, nitric acid, hydrobromic acid, phosphoric acid, perchloric acid, thiocyanic acid, boric acid, formic acid, acetic acid, haloacetic acid, propionic acid, glycolic acid, citric acid, tartaric acid, succinic acid, gluconic acid, lactic acid, malonic acid, fumaric acid, anthranilic acid, benzoic acid, cinnamic acid, p-toluenesulfonic acid, naphthalenesulfonic acid or sulfanilic acid; salts with alkali metal such as sodium or potassium, salts with alkaline-earth metal such as calcium or magnesium, or salts with other metals such as aluminum; or salts with bases such as ammonia or organic amines. Those salts may be manufactured by known methods from the compounds of the present invention in a free state or may be mutually converted among the salts. When the steric isomers such as cis-trans isomer, optical isomer and conformational isomer, or hydrate and metal complexes of the substances of the present invention exist, the present invention includes any and all of them.

The compound of the present invention can be made into pharmaceutical preparations by a combination with a suitable pharmaceutical carriers or diluents according to any conventional methods, for example, preparations for oral administrations (e.g. tablets, capsules, powders, liquids, etc.) and for parenteral administrations (e.g. for subcutaneous, intravenous, intramuscular, intrarectal and intranasal administrations). At preparing, the compound of the present invention may also be used in the form of the pharmaceutically acceptable salt, and can be used either solely or jointly together with other pharmaceutically effective ingredients.

Furthermore, depending upon the type of the disease and patient, it is possible to prepare other preparations than those which were mentioned already, for example, suitable preparations for the therapy, such as injections, suppositories, inhalations, aerosols, syrups, collyriums, medicines for external use (e.g. ointments), etc.

The preferred dose of the compound of the present invention may vary depending upon the object to be administered the patient, form of the preparation, method for the administration, term for the administration, etc. and, in order to achieve a desired effect, 0.5-1000 mg per day, preferably 1-500 mg per day may be usually given to common adults by oral route either once daily or several times a day. In the case of a parenteral administration such as by injection, a level of from $\frac{1}{3}$ to $\frac{1}{10}$ of the above-given dose by oral route is preferred.

EXAMPLES

The starting material is able to be purchased from Aldrich Chemical Co., Inc. or from Tokyo Kasei K. K. Melting point was measured by placing a sample in a glass capillary followed by using a melting point measuring device of a type Yamato MP-21 manufactured by Yamato (correction of a thermometer was not conducted). Oprical rotation was measured by a polarimeter of a type JASCO OD-140. $^1$H-NMR was measured by a nuclear magnetic resonance device of a type Brucker ARX500 and chemical shift values were expressed in terms of ppm using TMS ($\delta$=0 ppm) (which was added as an internal standard) as a basis. Silica gel column chromatography was conducted using silica gel BW-127ZH (Fuji Silicia Kagaku K. K.) for chromatography. In a thin-layer chromatography, Silica gel F254 (Merck, No. 5715) was used and detection was conducted using an UV lamp and a 5% ethanolic solution of phosphomolybdic acid as a coloring reagent. With regard to reagents and solvents, those which are available in the market were used as they were.

Example 1

Production of 2-hydroxy-1-phenylethanone

85% Ethanolic solution (1200 mL) of 2-bromo-1-phenylethanone (99.52 g, 500 mmol) and sodium formate (215.0 g, 3160 mol) was heated to reflux for 5 hours. After the solvent was evaporated in vacuo, water (1000 mL) was added to the residue and extraction with ethyl acetate was conducted. The organic layers were combined and dried over anhydrous sodium sulfate and the solvent was evaporated therefrom in vacuo. Petroleum ether was added to the residual oily product to crystallize whereupon 2-hydroxy-1-phenylethanone (59.67 g, 88%) was produced. Mp. 86-89° C. $^1$H-NMR (DMSO-$d_6$) $\delta$: 4.81 (d, J=5.8 Hz, 2H), 5.07 (t, J=5.8 Hz, 1H), 7.50-7.55 (m, 2H), 7.63-7.67 (m, 1H), 7.92-7.95 (m, 2H)

Example 2

Production of 1-(4-fluorophenyl)-2-hydroxyethanone 1-(4-Fluorophenyl)-2-hydroxyethanone (24.38 g, 75%) was produced from 2-bromo-1-(4-fluorophenyl)ethanone (45.58 g, 210 mmol), sodium formate (90.45 g, 1330 mmol) and 85% ethanol (500 mL) in the same manner as in the case of synthesis of 2-hydroxy-1-phenylethanone. Mp. 115-117° C.
$^1$H-NMR (DMSO-$d_6$) $\delta$: 4.78 (d, J=5.9 Hz, 2H), 5.11 (t, J=5.9 Hz, 1H), 7.33-7.38 (m, 2H), 8.00-8.04 (m, 2H).

Example 3

Production of (2-phenyl-[1,3]dioxolan-2-yl)methanol

2-Hydroxy-1-phenylethanone (49.39 g, 297 mmol), ethylene glycol (84 mL, 1500 mmol), p-toluenesulfonic acid monohydrate (1.0 g) and benzene (500 mL) were added to a one-liter eggplant type flask equipped with a Dean-Stark dehydrating device and heated to reflux for 24 hours. The solvent was evaporated in vacuo, water and ethyl acetate were added to the resulting residue and the organic layer was separated. An aqueous layer was further extracted with ethyl acetate twice and the organic layers were combined and washed with a saturated saline solution. It was dried over anhydrous sodium sulfate, the solvent was evaporated therefrom in vacuo and the resulting crude product was purified by a silica gel column chromatography (toluene:ethyl acetate=4: 1) to give (2-phenyl-[1,3]dioxolan-2-yl)methanol (52.30 g, 98%) as an oily product. $^1$H-NMR (DMSO-$d_6$) $\delta$: 3.51 (d, J=6.4 Hz, 2H), 3.74-3.78 (m, 2H), 4.01-4.05 (m, 2H), 4.09 (t, J=6.4 Hz, 1H), 7.28-7.36 (m, 3H), 7.40-7.43 (m, 2H).

Example 4

Production of [2-(4-fluorophenyl)-[1,3]dioxolan-2-yl]methanol

The same reaction as in the synthesis of 3a was conducted from 1-(4-fluorophenyl)-2-hydroxyethanone (23.89 g, 155 mmol), ethylene glycol (42 mL, 780 mmol), p-toluenesulfonic acid monohydrate (0.5 g) and benzene (300 mL) and the resulting crude product was purified by a silica gel column chromatography (toluene:ethyl acetate=4:1) to give [2-(4-fluorophenyl)-[1,3]dioxolan-2-yl]methanol (22.05 g, 72%) as an oily product. $^1$H-NMR (DMSO-$d_6$) δ: 3.51 (d, J=6.3 Hz, 2H), 3.75-3.81 (m, 2H), 3.99-4.07 (m, 2H), 4.94 (t, J=6.3 Hz, 1H), 7.13-7.19 (m, 2H), 7.42-7.47 (m, 2H).

Example 5

Production of 2-(3,5-bis(trifluoromethyl)benzyloxy methyl)-2-phenyl-[1,3]dioxolane (2-Phenyl-[1,3]dioxolan-2-yl)methanol (14.82 g, 82 mmol) was dissolved in DMF (200 mL) and cooled with ice and sodium hydride (60% oily) (3.60 g, 90 mmol) was added thereto by dividing into two. The mixture was stirred for 1 hour under cooling with ice and for 2 hours at room temperature and then a solution of 3,5-bis(trifluoromethyl)benzyl bromide (16.5 mL, 90 mmol) in DMF (50 mL) was dropped thereinto during 30 minutes under cooling with ice. After the mixture was stirred for 2 hours under cooling with ice and for 20 hours at room temperature, the reaction mixture was added to water followed by extracting with ethyl acetate. The organic layers were combined, washed with a saturated saline solution and dried over anhydrous sodium sulfate. The residual oily product obtained by evaporation of the solvent in vacuo was purified by a silica gel column chromatography (n-hexane:ethyl acetate=19:1) to give 2-(3,5-bis(trifluoromethyl)benzyloxymethyl)-2-phenyl-[1,3]-dioxolane (34.00 g, 100%) as an oily product. $^1$H-NMR (DMSO-$d_6$) δ: 3.67 (s, 2H), 3.79-3.84 (m, 2H), 4.02-4.08 (m, 2H), 4.74 (s, 2H), 7.31-7.39 (m, 3H), 7.46-7.49 (m, 2H), 7.89 (s, 2H), 7.96 (s, 1H).

Example 6

Production of 2-(3,5-bis(trifluoromethyl)benzyloxymethyl)-2-(4-fluorophenyl)[1,3]dioxolane 2-(3,5-Bis(trifluoromethyl)benzyloxymethyl)-2-(4-fluorophenyl) [1,3], dioxolane (46.60 g, 100%) was produced as an oily product from [2-(4-Fluorophenyl)[1,3]dioxolane-2-yl]methanol (21.80 g, 110 mmol), sodium hydride (60% oily) (4.80 g, 120 mmol), 3,5-bis(trifluoromethyl)benzyl bromide (22.0 mL, 120 mmol) and DMF (250 mL) in the same manner as in the case of synthesis of 2-(3,5-bis(trifluoromethyl)benzyloxymethyl)-2-phenyl-[1,3]dioxolane. $^1$H-NMR (DMSO-$d_6$) δ: 3.75 (s, 2H), 3.80-3.87 (m, 2H), 4.00-4.07 (m, 2H), 4.74 (s, 2H), 7.14-7.19 (m, 2H), 7.47-7.53 (m, 2H), 7.86 (s, 2H), 7.97 (s, 1H).

Example 7

Production of 2-(3,5-bis(trifluoromethyl)benzyloxy)-1-phenylethanone 2-(3,5-Bis(trifluoromethyl)benzyloxymethyl)-2-phenyl-[1,3]dioxolane (50.72 g, 140 mmol) was dissolved in THF (300 mL), 60 mol/L hydrochloric acid (50 mL) was added thereto and the mixture was heated to reflux for 20 hours. After the solvent was evaporated in vacuo, water was added to the residue followed by extracting with chloroform. The organic layers were combined, washed with water and a saturated saline solution and dried over anhydrous sodium sulfate and the solvent was evaporated in vacuo to give 2-(3,5-bis(trifluoromethyl)-benzyloxy)-1-phenylethanone (48.90 g, 96%) as an oily product. $^1$H-NMR (DMSO-$d_6$) δ: 4.82 (s, 2H), 5.07 (s, 2H), 7.53-7.57 (m, 2H), 7.66-7.69 (m, 1H), 7.94-7.96 (m, 2H), 8.03 (s, 1H), 8.11 (s, 2H).

Example 8

Production of 2-(3,5-bis(trifluoromethyl)benzyloxy)-1-(4-fluorophenyl)ethanone 2-(3,5-Bis(trifluoromethyl)benzyloxy)-1-(4-fluorophenyl)ethanone (40.50 g, 97%) was produced as crystals from 2-(3,5-bis(trifluoromethyl)benzyloxymethyl)-2-(4-fluorophenyl) [1,3]dioxolane (46.60 g, 110 mmol), 6 mol/L HCl (50 mL) and THF (300 mL) in the same manner as in the case of synthesis of 2-(3,5-bis(trifluoromethyl)benzyloxy)-1-phenylethanone. Mp. 56-57° C. $^1$H-NMR (DMSO-$d_6$) δ: 4.81 (s, 2H), 5.05 (s, 2H), 7.34-7.39 (m, 2H), 8.00-8.05 (m, 3H), 8.09 (s, 2H).

Example 9

Production of ethyl 4-(3,5-bis(trifluoromethyl)benzyloxy)-3-phenyl-2-butenoate Ethyl diethoxyphosphorylacetate (30 mL, 150 mmol) was dropped into a suspension of sodium hydride (60% oily) (6.00 g, 150 mmol) in THF (300 mL) at room temperature during 30 minutes. After the dropping, the mixture was stirred at room temperature for 1 hour more, a solution of 2-(3,5-bis(trifluoromethyl)-benzyloxy)-1-phenylethanone (48.90 g, 135 mmol) in THF (100 mL) was dropped thereinto at room temperature during 30 minutes and the mixture was stirred for 1 hour more. The reaction mixture was added to water (1000 mL) followed by extracting with ethyl acetate. The organic layers were combined, washed with water and a saturated saline solution and dried over anhydrous sodium sulfate and the solvent was evaporated in vacuo. The residual oily product was purified by a silica gel column chromatography (n-hexane:ethyl acetate=9:1) to give ethyl 4-(3,5-bis(trifluoromethyl)-benzyloxy)-3-phenyl-2-butenoate (40.00 g, 69%) as an oily product. $^1$H-NMR (DMSO-$d_6$) δ: 1.23 (t, J=7.1 Hz, 3H), 4.15 (q, J=7.1 Hz, 2H), 4.63 (s, 2H), 5.08 (s, 2H), 6.24 (s, 1H), 7.39-7.43 (m, 3H), 7.57-7.61 (m, 2H), 7.79 (s, 2H), 7.96 (s, 1H).

Example 10

Production of ethyl 4-(3,5-bis(trifluoromethyl)benzyloxy)-3-(4-fluoro phenyl)-2-butenylate Ethyl 4-(3,5-bis(trifluoromethyl)benzyloxy)-3-(4-fluorophenyl)-2-butenylate (34.40 g, 73%) was produced as an oily product from 2-(3,5-bis(trifluoromethyl)benzyloxy)-1-(4-fluorophenyl)ethanone (39.93 g, 105 mmol), sodium hydride (60% oily) (4.60 g, 115 mmol), diethoxyphosphorylacetate (23 mL, 115 mmol) and THF (400 mL) in the same manner as in the case of synthesis of ethyl 4-(3,5-bis(trifluoromethyl)benzyloxy)-3-phenyl-2-butenoate. $^1$H-NMR (DMSO-$d_6$) δ: 1.04 (t, J=7.1 Hz, 3H), 3.95 (q, J=7.1 Hz, 2H), 4.42 (d, J=1.5 Hz), 5.05 (s, 2H), 6.15 (t, J=1.5 Hz, 1H), 7.15-7.21 (m, 2H), 7.29-7.34 (m, 2H), 7.92 (s, 2H), 8.01 (s, 1H).

Example 11

Production of ethyl 4-(3,5-bis(trifluoromethyl)benzyloxy)-3-phenylbutanoate

A mixture of ethyl 4-(3,5-bis(trifluoromethyl)benzyloxy)-3-phenyl-2-butenoate (40.00 g, 92.5 mmol), 5% Pd-carbon (1.00 g) and ethanol (250 mL) was stirred for 20 hours at room temperature in a hydrogen atmosphere. After filtering the catalyst, the solvent was evaporated in vacuo to give ethyl 4-(3,5-bis(trifluoromethyl)benzyloxy)-3-phenylbutanoate (40.18 g, 100%) as an oily product. $^1$H-NMR (DMSO-$d_6$) δ: 1.04 (t, J=7.1 Hz, 3H), 2.60 (dd, J=8.0, 15.5 Hz, 1H), 2.81 (dd, J=6.8, 15.5 Hz, 1H), 3.38-3.45 (m, 1H), 3.65 (d, J=6.9 Hz, 2H), 3.94 (q, J=7.1 Hz, 2H), 4.65 and 4.66 (ABq, J=14.1 Hz, 2H), 7.20-7.24 (m, 1H), 7.28-7.32 (m, 4H), 7.90 (s, 2H), 7.99 (s, 1H).

Example 12

Production of ethyl 4-(3,5-bis(trifluoromethyl)benzyloxy)-3-(4-fluoro phenyl)butylate Ethyl 4-(3,5-bis(trifluoromethyl)benzyloxy)-3-(4-fluorophenyl)butylate (33.93 g, 100%) was produced as an oily product from ethyl 4-(3,5-bis(trifluoromethyl)benzyloxy)-3-(4-fluorophenyl)-2-butenylate (34.00 g, 75 mmol), 5% palladium on carbon catalyst (0.50 g) and EtOH (200 mL) in the same manner as in the case of synthesis of ethyl 4-(3,5-bis(trifluoromethyl)benzyloxy)-3-phenylbutanoate. $^1$H-NMR (DMSO-$d_6$) δ: 1.06 (t, J=7.2 Hz, 3H), 2.62 (dd, J=8.2, 15.7 Hz, 1H), 2.82 (dd, J=6.8, 15.7 Hz, 1H), 3.40-3.48 (m, 1H), 3.60-3.70 (m, 2H), 3.95 (q, J=7.2 Hz, 2H), 4.63 and 4.69 (ABq, J=13.4 Hz, 2H), 7.07-7.13 (m, 2H), 7.30-7.36 (m, 2H), 7.87 (s, 2H), 7.98 (s, 1H).

Example 13

Production of 4-(3,5-bis(trifluoromethyl)benzyloxy)-3-phenylbutanoic acid

Ethyl 4-(3,5-bis(trifluoromethyl)benzyloxy)-3-phenylbutanoate (26.06 g, 60 mmol) was dissolved in ethanol (300 mL), a 2 mol/L aqueous solution of sodium hydroxide was added thereto and the mixture was stirred for 20 hours at room temperature. The solvent was evaporated in vacuo and the resulting residue was dissolved in water and acidified with 6 mol/L hydrochloric acid. The oily product separated out therefrom was extracted with chloroform and the organic layers were combined and washed with water and a saturated saline solution. After it was dried over anhydrous sodium sulfate, the solvent was evaporated in vacuo to give 4-(3,5-bis(trifluoromethyl)benzyloxy)-3-phenylbutanoic acid (26.60 g, 90%) as an oily product. $^1$H-NMR (DMSO-$d_6$) δ: 2.56 (dd, J=8.4, 16.0 Hz, 1H), 2.73 (dd, J=6.4, 16.0 Hz, 1H), 3.35-3.40 (m, 1H), 3.63-3.66 (m, 2H), 4.64 and 4.66 (ABq, J=13.4 Hz, 2H), 7.19-7.25 (m, 1H), 7.27-7.31 (m, 4H), 7.88 (s, 2H), 7.98 (s, 1H), 12.09 (brs, 1H).

Example 14

Production of 4-(3,5-bis(trifluoromethyl)benzyloxy)-3-(4-fluorophenyl)butylic acid 4-(3,5-Bis(trifluoromethyl)benzyloxy)-3-(4-fluorophenyl)butylic acid (29.10 g, 91%) was produced as an oily product from ethyl 4-(3,5-bis(trifluoromethyl)benzyloxy)-3-(4-fluorophenyl)butylate (34.00 g, 75 mmol), 2 mol/L NaOH (75 mL, 150 mmol of NaOH) and EtOH (350 mL) in the same manner as in the case of synthesis of 4-(3,5-bis(trifluoromethyl)benzyloxy)-3-phenylbutylic acid. $^1$H-NMR (DMSO-$d_6$) δ: 2.58 (dd, J=8.5, 16.0 Hz, 1H), 2.75 (dd, J=6.4, 16.0 Hz, 1H), 3.37-3.42 (m, 1H), 3.58-3.68 (m, 2H), 4.63 and 4.68 (ABq, J=13.5 Hz, 2H), 7.07-7.13 (m, 2H), 7.30-7.36 (m, 2H), 7.84 (s, 2H), 7.97 (s, 1H), 12.12 (brs, 1H).

Example 15

Production of tert-butyl[3-(3,5-bis(trifluoromethyl)benzyloxy)-2-phenylpropyl]carbonate 4-(3,5-Bis(trifluoromethyl)benzyloxy-3-phenylbutanoic acid (24.38 g, 60 mmol), triethylamine (9.8 mL, 70 mmol) and DPPA (15 mL, 70 mmol) were dissolved in toluene (300 mL) and heated to reflux for 1 hour. After the reaction mixture was allowed to cool, tert-BuOH (50 mL) was added thereto followed by heating to reflux for 20 hours more. The solvent was evaporated in vacuo, water was added to the residue and the mixture was extracted with ethyl acetate. The organic layers were combined, washed with water and a saturated saline solution and dried over anhydrous sodium sulfate. The solvent was evaporated in vacuo and the resulting residue was purified by a silica gel column chromatography (toluene:ethyl acetate=19:1) to give tert-butyl [3-(3,5-bis(trifluoromethyl)benzyloxy)-2-phenylpropyl]carbonate (18.36 g, 64%) as crystals.

Example 16

Production of tert-butyl[3-(3,5-bis(trifluoromethyl)benzyloxy)-2-(4-fluorophenyl)propyl]carbamate tert-Butyl [3-(3,5-bis(trifluoromethyl)benzyloxy)-2-(4-fluorophenyl)propyl]carbamate (37.92 g, 66%) was produced as crystals from 4-(3,5-bis(trifluoromethyl)benzyloxy)-3-(4-fluorophenyl)butylic acid (49.22 g, 116 mmol), triethylamine (17.5 mL, 125 mmol), DPPA (27 mL, 127 mmol), t-BuOH (50 mL) and toluene (400 mL) in the same manner as in the case of synthesis of tert-butyl [3-(3,5-bis(trifluoromethyl)benzyloxy)-2-phenylpropyl]carbamate. Mp. 70-71° C. $^1$H-NMR (DMSO-$d_6$) δ: 1.32 (s, 9H), 3.10-3.19 (m, 2H), 3.25-3.33 (m, 1H), 3.62-3.71 (m, 2H), 4.62 and 4.64 (ABq, J=13.5 Hz, 2H), 6.83 (t, J=5.7 Hz, 1H), 7.06-7.12 (m, 2H), 7.24-7.29 (m, 2H), 7.85 (s, 2H), 7.97 (s, 1H).

Example 17

Production of 3-(3,5-bis(trifluoromethyl)benzyloxy)-2-phenylpropylamine hydrochloride tert-Butyl [3-(3,5-bis(trifluoromethyl)benzyloxy)-2-phenylpropyl]carbonate (9.55 g, 20 mmol) was dissolved in $CH_2Cl_2$ (100 mL) and 4 mol/L hydrogen chloride/dioxane (100 mL) was added thereto at room temperature. After the mixture was stirred for 1 hour, the solvent was evaporated in vacuo. The resulting residual oily product was crystallized from petroleum ether to give 3-(3,5-bis(trifluoromethyl)benzyloxy)-2-phenylpropylamine hydrochloride (8.24 g, 100%). Mp. 114-115° C. $^1$H-NMR (DMSO-$d_6$) δ: 3.08 (dd, J=7.6, 12.9 Hz, 1H), 3.26 (dd, J=7.1, 12.9 Hz, 1H), 3.35-3.42 (m, 1H), 3.72 (dd, J=6.1, 9.6 Hz, 1H), 3.82 (dd, J=6.6, 9.6 Hz, 1H), 4.68 and 4.70 (ABq, J=13.7 Hz, 2H), 7.26-7.38 (m, 5H), 7.93 (s, 2H), 7.99 (s, 1H), 8.18 (brs, 3H).

Example 18

Production of 3-(3,5-bis(trifluoromethyl)benzyloxy)-2-(4-fluorophenyl)propylamine hydrochloride 3-(3,5-Bis(trifluoromethyl)benzyloxy)-2-(4-fluorophenyl)propylamine hydrochloride (21.16 g, 98%) was produced as crystals from tert-butyl [3-(3,5-bis(trifluoromethyl)benzyloxy)-2-(4-fluorophenyl)propyl]carbamate (24.77 g, 50 mmol), 4 mol/L hydrogen chloride/dioxane (150 mL) and $CH_2Cl_2$ (150 mL) in the same manner as in the case of synthesis of the compound produced in Example 17. Mp. 142-143° C. $^1$H-NMR (DMSO-$d_6$) δ: 3.07 (dd, J=8.0, 12.9 Hz, 1H), 3.24 (dd, J=6.7, 12.9 Hz, 1H), 3.36-3.43 (m, 1H), 3.70 (dd, J=6.3, 9.6 Hz, 1H), 3.79 (dd, J=6.5, 9.6 Hz, 1H), 4.68 (s, 2H), 7.16-7.22 (m, 2H), 7.36-7.42 (m, 2H), 7.89 (s, 2H), 7.99 (s, 1H), 8.13 (brs, 3H).

Example 19

Production of tert-butyl [3-(3,5-bis(trifluoromethyl)benzyloxy)-2-phenylpropyl]methylcarbamate The compound produced in Example 15 (9.54 g, 20 mmol) was dissolved in DMF (60 mL) and 60% oily sodium hydride (1.20 g, 30 mmol) was added thereto at 0° C. by dividing into four. After the mixture was stirred for 4 hours at room temperature, it was returned to 0° C. and a solution of methyl iodide (1.9 mL, 30 mmol) in DMF (10 mL) was dropped thereinto. After the reaction mixture was stirred at room temperature for 20 hours more, it was added to water followed by extracting with ethyl acetate. After the organic layer was washed with water and a saturated saline solution, the residue obtained by evaporation of the solvent therefrom in vacuo was purified by a silica gel column chromatography (hexane:ethyl acetate=85:15) to give tert-butyl [3-(3,5-bis(trifluoromethyl)benzyloxy)-2-phenyl-propyl]methylcarbamate (8.08 g, 82%) as an oily product. $^1$H-NMR (CDCl$_3$) δ: 1.38 (s, 9H), 2.66-2.78 (m, 3H), 3.21-3.50 (m, 2H), 3.60-3.90 (m, 3H), 4.50-4.63 (m, 2H), 7.15-7.36 (m, 5H), 7.68 (s, 2H), 7.77 (s, 1H).

Example 20

Production of tert-butyl[3-(3,5-bis(trifluoromethyl)benzyloxy)-2-(4-fluorophenyl)propyl]methyl carbamate In the same manner as Example 19, tert-butyl [3-(3,5-bis(trifluoromethyl)benzyloxy)-2-(4-fluorophenyl)propyl]methylcarbamate (6.94 g, 85%) was prepared as an oily product from the compound produced in Example 16 (7.93 g, 16 mmol), 60% oily sodium hydride (0.96 g, 24 mmol), methyl iodide (1.5 mL, 24 mmol) and DMF (50 mL). $^1$H-NMR (CDCl$_3$) δ: 1.38 (s, 9H), 2.69-2.80 (m, 3H), 3.22-3.80 (m, 5H), 4.51-4.62 (m, 2H), 6.95-7.02 (m, 2H), 7.12-7.25 (m, 2H), 7.67 (s, 2H), 7.78 (s, 1H).

Example 21

Production of [3-(3,5-bis(trifluoromethyl)benzyloxy)-2-phenylpropyl]methylamine hydrochloride In the same manner as Example 17, [3-(3,5-bis(trifluoromethyl)benzyloxy)-2-phenylpropyl]methylamine hydrochloride (6.84 g, 100%) was prepared as crystals from the compound produced in Example 19 (7.86 g, 16 mmol), 4 mol/L hydrogen chloride/dioxane (32 mL) and dioxane (32 mL). $^1$H-NMR (DMSO-$d_6$) δ: 2.64 (s, 3H), 3.14-3.24 (m, 1H), 3.48-3.70 (m, 2H), 3.84 (dd, J=6.2, 9.5 Hz, 1H), 3.93 (dd, J=4.6, 9.5 Hz, 1H), 4.68 (d, J=12.6 Hz, 1H), 4.76 (d, J=12.6 Hz, 1H), 7.21-7.40 (m, 5H), 7.77 (s, 2H), 7.78 (s, 1H), 9.55 (brs, 2H).

Example 22

Production of [3-(3,5-bis(trifluoromethyl)benzyloxy)-2-(4-fluorophenyl)propyl]methylamine hydrochloride In the same manner as Example 17, [3-(3,5-bis(trifluoromethyl)benzyloxy)-2-(4-fluorophenyl)propyl]methylamine hydrochloride (6.06 g, 100%) was produced as crystals from the compound produced in Example 20 (6.93 g, 13.6 mmol), 4 mol/L hydrogen chloride/dioxane (20 mL) and dioxane (20 mL). $^1$H-NMR (DMSO-$d_6$) δ: 3.16-3.27 (m, 1H), 3.31-3.40 (m, 1H), 3.44-3.53 (m, 1H), 3.57 (s, 3H), 3.64-3.72 (m, 1H), 3.73-3.80 (m, 1H), 4.68 (s, 2H), 7.14-7.21 (m, 2H), 7.34-7.41 (m, 2H), 7.89 (s, 2H), 8.00 (s, 1H), 8.58 (brs, 1H), 9.03 (brs, 1H).

Example 23

Production of 3-(4-fluorobenzyloxy)-2-phenylpropylamine hydrochloride

In the same manner as Example 17, title compound was produced. $^1$H-NMR (DMSO-$d_6$) δ: 3.02-3.13 (m, 1H), 3.20-3.30 (m, 2H), 3.54-3.36 (m, 1H), 3.62-3.70 (m, 1H), 4.45 and 4.46 (ABq, J=14.5 Hz, 2H), 7.10-7.17 (m, 2H), 7.22-7.36 (m, 7H), 7.96 (brs, 3H).

Example 24

Production of 3-(3,5-dimethylbenzyloxy)-2-phenylpropylamine hydrochloride

In the same manner as Example 17, title compound was produced. $^1$H-NMR (DMSO-$d_6$) δ: 2.23 (s, 6H), 3.04-3.14 (m, 1H), 3.19-3.29 (m, 2H), 3.53-3.66 (m, 2H), 4.40 (s, 2H), 6.83 (s, 2H), 6.89 (s, 1H), 7.26-7.41 (m, 5H), 7.84 (brs, 3H).

Example 25

Production of 3-(3,4-dichlorobenzyloxy)-2-phenylpropylamine hydrochloride

In the same manner as Example 17, title compound was produced. $^1$H-NMR (DMSO-$d_6$) δ: 3.07 (dd, J=7.7, 12.8 Hz, 1H), 3.24 (dd, J=6.9, 12.8 Hz, 1H), 3.30-3.36 (m, 1H), 3.63 (dd, J=5.8, 9.6 Hz, 1H), 3.72 (dd, J=7.0, 9.6 Hz, 1H), 4.48 and 4.50 (ABq, J=12.7 Hz, 2H), 7.24-7.38 (m, 6H), 7.49 (d, J=1.9 Hz, 1H), 7.58 (d, J=8.2 Hz, 1H), 8.11 (brs, 3H).

Example 26

Production of 3-(3,5-diflorobenzyloxy)-2-phenylpropylamine hydrochloride

In the same manner as Example 17, title compound was produced. $^1$H-NMR (DMSO-$d_6$) δ: 3.08 (dd, J=7.6, 12.7 Hz, 1H), 3.26 (dd, J=6.9, 12.7 Hz, 1H), 3.30-3.36 (m, 1H), 3.64 (dd, J=5.8, 9.6 Hz, 1H), 3.73 (dd, J=6.8, 9.6 Hz, 1H), 4.50 and 4.52 (ABq, J=13.1 Hz, 2H), 6.93-6.99 (m, 2H), 7.08-7.38 (m, 1H), 7.27-7.38 (m, 5H), 8.08 (brs, 3H).

Example 27

Production of 3-(3-trifloromethylbenzyloxy)-2-phenylpropylamine hydrochloride

In the same manner as Example 17, title compound was produced. $^1$H-NMR (DMSO-$d_6$) δ: 3.08 (dd, J=7.8, 12.8 Hz, 1H), 3.25 (dd, J=6.8, 12.8 Hz, 1H), 3.31-3.38 (m, 1H), 3.67 (dd, J=5.9, 9.6 Hz, 1H), 3.75 (dd, J=7.0, 9.6 Hz, 1H), 4.57 and 4.59 (ABq, J=12.8 Hz, 2H), 7.26-7.38 (m, 5H), 7.55-7.66 (m, 4H), 8.11 (brs, 3H).

Example 28

Production of 3-benzyloxy-2-phenylpropylamine hydrochloride

In the same manner as Example 17, title compound was produced. $^1$H-NMR (DMSO-$d_6$) δ: 3.04-3.14 (m, 1H), 3.19-3.29 (m, 2H), 3.53-3.66 (m, 2H), 4.40 (s, 2H), 7.20-7.49 (m, 10H), 7.84 (brs, 3H).

Example 29

Production of N-[3-(3,5-bis(trifluoromethyl)benzyloxy)-2-phenylpropyl]-1-methylpiperidine-4-carboxamide [Compound 1]

4-Methylpiperidine-4-carboxylic acid (0.41 g, 2.9 mmol), the compound produced in Example 17 (0.99 g, 2.9 mmol) and triethylamine (0.40 mL, 2.9 mmol) were dissolved in CH$_2$Cl$_2$ (10 mL) and WSC.HCl (0.56 g, 2.9 mmol) was added thereto at room temperature. After the mixture was stirred for 20 hours at room temperature, water was added to the residue obtained by evaporation of the solvent in vacuo and the mixture was extracted with ethyl acetate. The organic layers were combined, washed with water and a saturated saline solution and dried over anhydrous sodium sulfate. The solvent was evaporated therefrom in vacuo to give Compound 1 (1.12 g, 93%) as an oily product.

Example 30

Production of N-[3-(3,5-bis(trifluoromethyl)-benzyloxy)-2-(4-fluorophenyl)propyl]-1-methylpiperidine-4-carboxamide hydrochloride [Compound 2]

A 4 mol/L hydrogen chloride/dioxane (1.0 mL; 4 mmol hydrogen chloride) was added to an oily product which was produced from N-methylpiperidine-4-carboxylic acid (0.34 g, 2.4 mmol), the compound produced in Example 18 (0.86 g, 2.0 mmol), triethylamine (0.28 mL, 2.0 mmol), WSC.HCl (0.46 g, 2.4 mmol) and CH$_2$Cl$_2$ (10 mL) by the same manner as in Example 29 and, after that, the solvent and an excessive hydrogen chloride were evaporated therefrom in vacuo. The residual oily product was solidified with petroleum ether to give Compound 2 (1.11 g, 100%) as a hygroscopic non-crystalline solid.

Example 31

Production of N-[3-(3,5-bis(trifluoromethyl)benzyloxy)-2-phenylpropyl]-1-isopropylpiperidine-4-carboxamide [Compound 3]

In the same manner as Example 30, Compound 3 (0.51 g, 40%) was produced as a hygroscopic non-crystalline solid from 1-isopropylpiperidine-4-carboxylic acid (0.50 g, 2.9 mmol), the compound produced in Example 17, triethylamine (0.40 mL, 2.9 mmol) WSC.HCl (0.56 g, 2.9 mmol) and methylene (10 mL).

Example 32

Production of N-[3-(3,5-bis(trifluoromethyl)benzyloxy)-2-phenylpropyl]piperidine-4-carboxamide hydrochloride [Compound 4]

A residual oily product produced from N-Boc piperidine-4-carboxylic acid (0.66 g, 2.9 mmol), 3-(3,5-bis(trifluoromethyl)benzyloxy)-2-phenylpropylamine hydrochloride (0.99 g, 2.4 mmol), triethylamine (0.40 mL, 2.9 mmol), WSC.HCl (0.56 g, 2.9 mmol) and CH$_2$Cl$_2$ (10 mL) by the same manner as in Example 30 was purified by a silica gel column chromatography (CH$_2$Cl$_2$: MeOH=19:1) to give the Compound 71 (1.26 g, 89%) as an oily product. The Compound 71 (1.24 g, 2.1 mmol) was dissolved in dioxane (4.2 mL) and a 4 mol/L hydrogen chloride/dioxane (4.2 mL) was added thereto at room temperature. After the mixture was stirred for 20 hours, the solvent was evaporated in vacuo. Ether was added to the resulting residue to give Compound 4 (1.03 g, 93%).

Example 33

Production of N-[3-(3,5-bis(trifluoromethyl)benzyloxy)-2-(4-fluorophenyl)propyl]piperidine-4-carboxamide hydrochloride [Compound 5]

N-Boc-piperidine-4-carboxylic acid (0.55 g, 2.4 mmol), the compound produced in Example 18 (0.86 g, 2.0 mmol), triethylamine (0.28 mL, 2.0 mmol), WSC.HCl (0.46 g, 2.4 mmol), and CH$_2$Cl$_2$ (10 mL) were reacted in the same manner as Example 30 to give the residue. The residue was purified on a silica gel column chromatograph (CH$_2$Cl$_2$: MeOH=19:1) to give Compound 72 as an oily product (1.14 g, 94%). Compound 5 (1.00 g, 97%) was produced as an oily product from Compound 72 (1.14 g, 1.9 mmol), 4 mol/L hydrogen chloride/dioxane (2.9 mL) and dioxane (2.9 mL) in the same manner in the case of synthesis of Compound 4.

Example 34

Production of N-[3-(3,5-bis(trifluoromethyl)benzyloxy)-2-phenylpropyl]isonicotinamide [Compound 6]

In the same manner as Example 30, an oily residue was produced from isonicotinic acid (0.81 g, 6.6 mmol), the compound produced in Example 17 (2.48 g, 6 mmol), triethylamine (0.9 mL, 6.6 mmol), WSC.HCl (1.26 g, 6.6 mmol) and CH$_2$Cl$_2$ (50 mL). The residue was purified on a silica gel column chromatograph (CHCl$_3$: MeOH=19:1) and crystallized with petroleum ether to give Compound 6 (2.22 g, 77%).

Example 35

Production of N-[3-(3,5-bis(trifluoromethyl)benzyloxy)-2-(4-fluorophenyl)propyl]isonicotinamide [Compound 7]

In the same manner as Example 30, an oily residue was produced from isonicotinic acid (0.30 g, 2.4 mmol), the compound produced in Example 18 (0.86 g, 2 mmol), triethylamine (0.28 mL, 2.4 mmol), WSC.HCl (0.20 g, 2 mmol) and CH$_2$Cl$_2$ (10 mL). The residue was purified on a silica gel column chromatograph (CH$_2$Cl$_2$: MeOH=19:1) and crystallized with petroleum ether to give Compound 7 (0.84 g, 84%).

Example 36

Production of N-[3-(3,5-bis(trifluoromethyl)benzyloxy)-2-phenylpropyl]nicotinamide [Compound 8]

In the same manner as Example 30, an oily residue was produced from nicotinic acid (0.74 g, 6.0 mmol), the compound produced in Example 17 (2.07 g, 5.0 mmol), triethylamine (0.84 mL, 6.0 mmol), WSC.HCl (1.15 g, 6.0 mmol) and CH$_2$Cl$_2$ (50 mL). The residue was purified on a silica gel column chromatograph (CHCl$_3$: MeOH=19:1) and crystallized with petroleum ether to give Compound 8 (2.14 g, 89%).

Example 37

Production of N-[3-(3,5-bis(trifluoromethyl)benzyloxy)-2-(4-fluorophenyl)propyl]nicotinamide [Compound 9]

In the same manner as Example 30, an oily residue was produced from nicotinic acid (0.81 g, 6.6 mmol), the compound produced in Example 18 (2.60 g, 6.0 mmol), triethylamine (0.9 mL, 6.6 mmol), WSC.HCl (1.26 g, 6.6 mmol) and CH$_2$Cl$_2$ (50 mL). The residue was purified on a silica gel column chromatograph (CHCl$_3$: MeOH=19:1) and crystallized with petroleum ether to give Compound 9 (2.61 g, 87%).

Example 38

Production of N-[3-(3,5-bis(trifluoromethyl)benzyloxy)-2-(4-fluorophenyl)propyl]pyridine-2-carboxamide [Compound 10]

In the same manner as Example 30, an oily residue was produced from pyridine-2-carboxylic acid (1.35 g, 11 mmol), the compound produced in Example 18 (4.32 g, 10 mmol), triethylamine (1.5 mL, 11 mmol), WSC.HCl (2.11 g, 11 mmol) and CH$_2$Cl$_2$ (50 mL). The residue was purified on a silica gel column chromatograph (CHCl$_3$: MeOH=19:1) and crystallized with petroleum ether to give Compound 10 (2.14 g, 43%).

Example 39

Production of N-[3-(3,5-bis(trifluoromethyl)benzyloxy)-2-phenylpropyl]-2-chloroisonicotinamide [Compound 11]

In the same manner as Example 30, an oily residue was produced from 2-chloroisonicotinic acid (1.10 g, 5.0 mmol), the compound produced in Example 17 (2.07 g, 5.0 mmol), triethylamine (0.7 mL, 5.0 mmol), WSC.HCl (1.34 g, 7.0 mmol) and CH$_2$Cl$_2$ (15 mL). The residue was purified on a silica gel column chromatograph (CH$_2$Cl$_2$: MeOH=19:1) and crystallized with petroleum ether to give Compound 10 (0.87 g, 24%).

Example 40

Production of N-[3-(3,5-bis(trifluoromethyl)benzyloxy)-2-(4-fluorophenyl)propyl]-2-hydroxyisonicotinamide [Compound 12]

In the same manner as Example 30, an oily residue was produced from 2-hydroxyisonicotinic acid (0.33 g, 2.4 mmol), the compound produced in Example 18 (0.86 g, 2.0 mmol), triethylamine (0.28 mL, 2.0 mmol), WSC.HCl (0.46 g, 2.4 mmol) and CH$_2$Cl$_2$ (10 mL). The residue was purified on a silica gel column chromatograph (CH$_2$Cl$_2$: MeOH=19:1) and crystallized with petroleum ether to give Compound 12 (0.37 g, 36%).

Example 41

Production of N-[3-(3,5-bis(trifluoromethyl)benzyloxy)-2-phenylpropyl]-6-methylnicotinamide [Compound 13]

In the same manner as Example 30, an oily residue was produced from 2-methylnicotinic acid (0.33 g, 2.4 mmol), the compound produced in Example 17 (0.83 g, 2.0 mmol), triethylamine (0.28 mL, 2.0 mmol), WSC.HCl (0.46 g, 2.4 mmol) and CH$_2$Cl$_2$ (10 mL). The residue was purified on a silica gel column chromatograph (CH$_2$Cl$_2$: MeOH=19:1) and crystallized with petroleum ether to give Compound 13 (0.99 g, 83%).

Example 42

Production of N-[3-(3,5-bis(trifluoromethyl)benzyloxy)-2-phenylpropyl]-2-chloro-6-methylnicotinamide [Compound 14]

In the same manner as Example 30, an oily residue was produced from 2-chloro-6-methylnicotinic acid (0.41 g, 2.4 mmol), the compound produced in Example 17 (0.83 g, 2.0 mmol), triethylamine (0.28 mL, 2.0 mmol), WSC.HCl (0.46 g, 2.4 mmol) and CH$_2$Cl$_2$ (10 mL). The residue was purified on a silica gel column chromatograph (CH$_2$Cl$_2$: MeOH=19:1) and crystallized with petroleum ether to give Compound 14 (0.56 g, 53%).

Example 43

Production of N-[3-(3,5-bis(trifluoromethyl)benzyloxy)-2-phenylpropyl]-2,6-dichloronicotinamide [Compound 15]

In the same manner as Example 30, an oily residue was produced from 2,6-dichloronicotinic acid (0.41 g, 2.4 mmol), the compound produced in Example 17 (0.83 g, 2.0 mmol), triethylamine (0.28 mL, 2.0 mmol), WSC.HCl (0.46 g, 2.4 mmol) and CH$_2$Cl$_2$ (10 mL). The residue was purified on a silica gel column chromatograph (CH$_2$Cl$_2$: MeOH=19:1) and crystallized with petroleum ether to give Compound 15 (0.63 g, 57%).

Example 44

Production of N-[3-(3,5-bis(trifluoromethyl)benzyloxy)-2-phenylpropyl]-2,6-dichloro-5-fluoronicotinamide [Compound 16]

In the same manner as Example 30, an oily residue was produced from 2,6-dichloro-5-fluoronicotinic acid (0.50 g, 2.4 mmol), the compound produced in Example 17 (0.83 g, 2.0 mmol), triethylamine (0.28 mL, 2.0 mmol), WSC.HCl (0.46 g, 2.4 mmol) and $CH_2Cl_2$ (10 mL). The residue was purified on a silica gel column chromatograph ($CH_2Cl_2$: MeOH=19:1) and crystallized with petroleum ether to give Compound 16 (0.49 g, 43%).

Example 45

Production of N-[3-(3,5-bis(trifluoromethyl)benzyloxy)-2-phenylpropyl]-2,6-dimethoxynicotinamide [Compound 17]

In the same manner as Example 30, an oily residue was produced from 2,6-dimethoxynicotinic acid (0.44 g, 2.4 mmol), the compound produced in Example 17 (0.83 g, 2.0 mmol), triethylamine (0.28 mL, 2.0 mmol), WSC.HCl (0.46 g, 2.4 mmol) and $CH_2Cl_2$ (10 mL). The residue was purified on a silica gel column chromatograph ($CH_2Cl_2$: MeOH=19:1) and crystallized with petroleum ether to give Compound 17 (0.40 g, 37%).

Example 46

Production of N-[3-(3,5-bis(trifluoromethyl)benzyloxy)-2-phenylpropyl]quinoline-4-carboxamide [Compound 18]

In the same manner as Example 30, an oily residue was produced from quinoline-4-carboxylic acid (0.50 g, 2.9 mmol), the compound produced in Example 17 (1.12 g, 2.7 mmol), triethylamine (0.40 mL, 2.9 mmol), WSC.HCl (0.56 g, 2.9 mmol) and $CH_2Cl_2$ (25 mL). The residue was purified on a silica gel column chromatograph ($CHCl_3$: MeOH=19:1) and crystallized with petroleum ether to give Compound 18 (0.55 g, 38%).

Example 47

Production of N-[3-(3,5-bis(trifluoromethyl)benzyloxy)-2-(4-fluorophenyl)propyl]quinoline-4-carboxamide [Compound 19]

In the same manner as Example 30, an oily residue was produced from quinoline-4-carboxylic acid (0.50 g, 2.9 mmol), the compound produced in Example 18 (1.17 g, 2.7 mmol), triethylamine (0.40 mL, 2.9 mmol), WSC.HCl (0.56 g, 2.9 mmol) and $CH_2Cl_2$ (25 mL). The residue was purified on a silica gel column chromatograph ($CHCl_3$: MeOH=19:1) and crystallized with petroleum ether to give Compound 19 (0.55 g, 37%).

Example 48

Production of N-[3-(3,5-bis(trifluoromethyl)benzyloxy)-2-phenylpropyl]-1-oxyisonicotinamide [Compound 20]

In the same manner as Example 30, an oily residue was produced from 1-oxyisonicotinic acid (0.33 g, 2.4 mmol), the compound produced in Example 17 (0.83 g, 2.0 mmol), triethylamine (0.28 mL, 2.0 mmol), WSC.HCl (0.46 g, 2.4 mmol) and $CH_2Cl_2$ (15 mL). The residue was purified on a silica gel column chromatograph ($CH_2Cl_2$: MeOH=19:1) and crystallized with petroleum ether to give Compound 20 (0.97 g, 97%).

Example 49

Production of N-[3-(3,5-bis(trifluoromethyl)benzyloxy)-2-(4-fluorophenyl)propyl]-1-oxyisonicotinamide [Compound 21]

In the same manner as Example 30, an oily residue was produced from 1-oxyisonicotinic acid (0.33 g, 2.4 mmol), the compound produced in Example 18 (0.86 g, 2.0 mmol), triethylamine (0.28 mL, 2.0 mmol), WSC.HCl (0.46 g, 2.4 mmol) and $CH_2Cl_2$ (10 mL). The residue was purified on a silica gel column chromatograph ($CH_2Cl_2$: MeOH=19:1) and crystallized with petroleum ether to give Compound 21 (0.74 g, 72%).

Example 50

Production of N-[3-(3,5-bis(trifluoromethyl)benzyloxy)-2-phenylpropyl]-1-oxynicotinamide [Compound 22]

In the same manner as Example 30, an oily residue was produced from 1-oxynicotinic acid (0.36 g, 2.6 mmol), the compound produced in Example 17 (1.00 g, 2.4 mmol), triethylamine (0.36 mL, 2.6 mmol), WSC.HCl (0.50 g, 2.6 mmol) and $CH_2Cl_2$ (20 mL). The residue was purified on a silica gel column chromatograph ($CHCl_3$: MeOH=19:1) and crystallized with petroleum ether to give Compound 22 (0.66 g, 55%).

Example 51

Production of N-[3-(3,5-bis(trifluoromethyl)benzyloxy)-2-(4-fluorophenyl)propyl]-1-oxynicotinamide [Compound 23]

In the same manner as Example 30, an oily residue was produced from 1-oxynicotinic acid (0.31 g, 2.2 mmol), the compound produced in Example 18 (0.86 g, 2.0 mmol), triethylamine (0.30 mL, 2.2 mmol), WSC.HCl (0.42 g, 2.2 mmol) and $CH_2Cl_2$ (20 mL). The residue was purified on a silica gel column chromatograph ($CHCl_3$: MeOH=19:1) and crystallized with petroleum ether to give Compound 23 (0.64 g, 62%).

Example 52

Production of N-[3-(3,5-bis(trifluoromethyl)benzyloxy)-2-phenylpropyl]-1-oxypyridine-2-carboxamide [Compound 24]

In the same manner as Example 30, an oily residue was produced from 1-oxypyridine-2-carboxylic acid (0.38 g, 2.7 mmol), the compound produced in Example 17 (1.03 g, 2.5 mmol), triethylamine (0.38 mL, 2.7 mmol), WSC.HCl (0.52 g, 2.7 mmol) and $CH_2Cl_2$ (25 mL). The residue was purified on a silica gel column chromatograph ($CHCl_3$: acetone=19:1) and crystallized with petroleum ether to give Compound 24 (0.45 g, 36%).

Example 53

Production of: N-[3-(3,5-bis(trifluoromethyl)benzyloxy)-2-(4-fluorophenyl)propyl]-1-oxypyridine-2-carboxamide [Compound 25]

In the same manner as Example 30, an oily residue was produced from 1-oxypyridine-2-carboxylic acid (0.38 g, 2.7 mmol), the compound produced in Example 18 (1.08 g, 2.5 mmol), triethylamine (0.38 mL, 2.7 mmol), WSC.HCl (0.52 g, 2.7 mmol) and $CH_2Cl_2$ (25 mL). The residue was purified on a silica gel column chromatograph ($CHCl_3$: acetone=19:1) and crystallized with petroleum ether to give Compound 25 (0.21 g, 16%).

Example 54

Production of 4-[3-(3,5-bis(trifluoromethyl)benzyloxy)-2-phenylpropylcarbamoyl]-1-methylpyridinium iodide [Compound 26]

Compound 6 (0.97 g, 2.0 mmol) was dissolved in $CH_2Cl_2$ (20 mL), and MeI (0.63 mL, 10.0 mmol) was added thereto. The reaction mixture was refluxed for 20 hours. The solvent was evaporated therefrom in vacuo. The resulting oily residue was crystallized with ether and petroleum ether to give compound 26 (1.18 g, 94%) as pale yellow crystals.

Example 55

Production of 4-[3-(3,5-bis(trifluoromethyl)benzyloxy)-2-(4-fluorophenyl)propylcarbamoyl]-1-methylpyridinium iodide [Compound 27]

In the same manner as in the case of synthesis of Compound 26, Compound 27 (1.44 g, 97%) was produced as pale yellow crystals from Compound 7 (1.17 g, 2.3 mmol), MeI (0.75 mL, 12.0 mmol) and $CH_2Cl_2$ (25 mL).

Example 56

Production of 3-[3-(3,5-bis(trifluoromethyl)benzyloxy)-2-phenylpropylcarbamoyl]-1-methylpyridinium iodide [Compound 28]

In the same manner as in the case of synthesis of Compound 26, Compound 28 (1.29 g, 94%) was produced as pale yellow crystals from Compound 8 (1.06 g, 2.2 mmol), MeI (0.70 mL, 11.0 mmol) and $CH_2Cl_2$ (20 mL).

Example 57

Production of 3-[3-(3,5-bis(trifluoromethyl)benzyloxy)-2-(4-fluorophenyl)propylcarbamoyl]-1-methylpyridinium iodide [Compound 29]

In the same manner as in the case of synthesis of Compound 26, Compound 28 (1.25 g, 97%) was produced as pale yellow crystals from Compound 9 (1.00 g, 2.0 mmol), MeI (0.62 mL, 10.0 mmol) and $CH_2Cl_2$ (20 mL).

Example 58

Production of 1-benzyl-4-[3-(3,4-bis(trifluoromethyl)-benzyloxy)-2-p henylpropylcarbamoyl]pyridinium chloride [Compound 30]

The same reaction as for the production of Compound 26 was conducted using Compound 7 (0.75 g, 1.6 mmol), benzyl chloride (1.42 mL, 12.0 mmol) and $CH_2Cl_2$ (25 mL) and, after that, the solvent was evaporated therefrom in vacuo. Ether and petroleum ether were added to the residual oily product and decantation was conducted for three times so as to remove an excessive benzyl chloride. The residual oily product was solidified with petroleum ether to give Compound 30 (0.76 g, 78%) as a hygroscopic amorphous solid.

Example 59

Production of 1-benzyl-4-[3-(3,5-bis(trifluoromethyl)benzyloxy)-2-(4-fluorophenyl)propylcarbamoyl]pyridinium chloride [Compound 31]

In the same manner as in the case of synthesis of Compound 30, Compound 31 (0.98 g, 87%) was produced as a hygroscopic amorphous solid from Compound 8 (0.90 g, 1.8 mmol), benzyl chloride (2.10 mL, 18.0 mmol) and $CH_2Cl_2$ (25 mL).

Example 60

Production of 1-benzyl-3-[3-(3,5-bis(trifluoromethyl)benzyloxy)-2-ph enylpropylcarbamoyl]pyridinium chloride [Compound 32]

In the same manner as in the case of synthesis of Compound 30, Compound 32 (1.19 g, 89%) was produced as a hygroscopic amorphous solid from Compound 9 (1.06 g, 2.2 mmol), benzyl chloride (2.2 mL, 19.0 mmol) and $CH_2Cl_2$ (25 mL).

Example 61

Production of N-[3-(3,5-bis(trifluoromethyl)benzyloxy)-2-phenylpropyl]-2-pyridin-4-ylacetamide [Compound 33]

In the same manner as in the case of synthesis of Compound 30, Compound 33 (3.90 g, 87%) was produced as crystals from pyridin-4-ylacetic acid hydrochloride (1.65 g, 9.5 mmol), the compound produced in Example 17 (3.72 g, 9.0 mmol), triethylamine (2.8 mL, 20 mmol), WSC.HCl (1.92 g, 10 mmol) and $CH_2Cl_2$ (50 mL).

Example 62

Production of N-[3-(3,5-bis(trifluoromethyl)benzyloxy)-2-(4-fluorophenyl)propyl]-2-pyridin-4-ylacetamide [Compound 34]

In the same manner as in the case of synthesis of Compound 30, Compound 34 (4.41 g, 86%) was produced as crystals from pyridin-4-ylacetic acid hydrochloride (2.08 g, 12 mmol), the compound produced in Example 18 (4.32 g, 10.0 mmol), triethylamine (3.4 mL, 24 mmol), WSC.HCl (2.30 g, 12 mmol) and $CH_2Cl_2$ (50 mL).

Example 63

Production of N-[3-(3,5-bis(trifluoromethyl)benzyloxy)-2-phenylpropyl]-2-pyridin-3-ylacetamide [Compound 35]

In the same manner as in the case of synthesis of Compound 30, Compound 35 (4.82 g, 97%) was produced as crystals from pyridin-3-ylacetic acid hydrochloride (2.08 g, 12 mmol), the compound produced in Example 17 (4.14 g, 10.0 mmol), triethylamine (3.4 mL, 24 mmol), WSC.HCl (2.30 g, 12 mmol) and $CH_2Cl_2$ (50 mL).

Example 64

Production of N-[3-(3,5-bis(trifluoromethyl)benzyloxy)-2-(4-fluorophenyl)propyl]-2-pyridin-3-ylacetamide [Compound 36]

In the same manner as in the case of synthesis of Compound 30, Compound 36 (4.55 g, 88%) was produced as crystals from pyridin-3-ylacetic acid hydrochloride (2.08 g, 12 mmol), the compound produced in Example 18 (4.32 g, 10.0 mmol), triethylamine (3.4 mL, 24 mmol), WSC.HCl (2.30 g, 12 mmol) and $CH_2Cl_2$ (50 mL).

Example 65

Production of N-[3-(3,5-bis(trifluoromethyl)benzyloxy)-2-phenylpropyl]-2-pyridin-2-ylacetamide [Compound 37]

In the same manner as in the case of synthesis of Compound 30, Compound 37 (4.68 g, 94%) was produced as crystals from pyridin-2-ylacetic acid hydrochloride (2.08 g, 12 mmol), the compound produced in Example 17 (4.14 g, 10.0 mmol), triethylamine (3.4 mL, 24 mmol), WSC.HCl (2.30 g, 12 mmol) and $CH_2Cl_2$ (50 mL).

Example 66

Production of N-[3-(3,5-bis(trifluoromethyl)benzyloxy)-2-(4-fluorophenyl)propyl]-2-pyridin-2-ylacetamide [Compound 38]

In the same manner as in the case of synthesis of Compound 30, Compound 38 (2.90 g, 85%) was produced as crystals from pyridin-2-ylacetic acid hydrochloride (1.22 g, 7.0 mmol), the compound produced in Example 18 (2.85 g, 6.6 mmol), triethylamine (2.0 mL, 14 mmol), WSC.HCl (1.34 g, 7.0 mmol) and $CH_2Cl_2$ (50 mL).

Example 67

Production of N-[3-(3,5-bis(trifluoromethyl)benzyloxy)-2-phenylpropyl]-2-(1-oxypyridin-4-yl)acetamide [Compound 39]

Compound 33 (2.85 g, 5.7 mmol) was dissolved in chloroform (50 mL), m-chloroperbenzoic acid (MCPBA) (1.21 g, 7.0 mmol) was added thereto and the mixture was stirred for 20 hours. After the solvent was evaporated in vacuo, 5% aqueous solution of sodium hydrogen carbonate and a saturated saline solution were added to the residual oily product and the mixture was extracted with ether. The organic layers were combined and dried over anhydrous sodium sulfate, the solvent was evaporated in vacuo and the resulting residual oily product was crystallized from petroleum ether to give Compound 39 (2.70 g, 92%).

Example 68

Production of N-[3-(3,5-bis(trifluoromethyl)benzyloxy)-2-(4-fluorophenyl)propyl]-2-(1-oxypyridin-4-yl)acetamide [Compound 40]

In the same manner as in the case of synthesis of Compound 39, Compound 40 (1.10 g, 82%) was produced as crystals from Compound 34 (1.34 g, 2.6 mmol), MCPBA (0.52 g, 3.0 mmol) and chloroform (25 mL).

Example 69

Production of N-[3-(3,5-bis(trifluoromethyl)benzyloxy)-2-phenylpropyl]-2-(1-oxypyridin-3-yl)acetamide [Compound 41]

In the same manner as in the case of synthesis of Compound 39, Compound 41 (3.76 g, 100%) was produced as crystals from Compound 35 (3.58 g, 7.2 mmol), MCPBA (1.72 g, 10 mmol) and chloroform (50 mL).

Example 70

Production of N-[3-(3,5-bis(trifluoromethyl)benzyloxy)-2-(4-fluorophenyl)propyl]-2-(1-oxypyridin-3-yl)acetamide [Compound 42]

In the same manner as in the case of synthesis of Compound 39, Compound 42 (2.94 g, 96%) was produced as crystals from Compound 36 (3.00 g, 5.8 mmol), MCPBA (1.38 g, 8.0 mmol) and chloroform (50 mL).

Example 71

Production of N-[3-(3,5-bis(trifluoromethyl)benzyloxy)-2-phenylpropyl]-2-(1-oxypyridin-2-yl)acetamide [Compound 43]

In the same manner as in the case of synthesis of Compound 39, Compound 43 (3.27 g, 94%) was produced as crystals from Compound 37 (3.36 g, 6.8 mmol), MCPBA (1.64 g, 9.5 mmol) and chloroform (50 mL).

Example 72

Production of N-[3-(3,5-bis(trifluoromethyl)benzyloxy)-2-(4-fluorophenyl)propyl]-2-(1-oxypyridin-2-yl)acetamide [Compound 44]

In the same manner as in the case of synthesis of Compound 39, Compound 44 (1.53 g, 93%) was produced as crystals from Compound 38 (1.59 g, 3.1 mmol), MCPBA (0.74 g, 4.3 mmol) and chloroform (30 mL).

Example 73

Production of: N-[3-(3,5-bis(trifluoromethyl)benzyloxy)-2-phenylpropyl]-3-pyridin-4-ylacrylamide [Compound 45]

In the same manner as in the case of synthesis of Compound 30, Compound 45 (6.68 g, 88%) was produced as crystals from 3-pyridin-4-ylacryllic acid (2.54 g, 17 mmol), the compound produced in Example 17 (6.21 g, 15 mmol), triethylamine (2.4 mL, 17 mmol), WSC.HCl (3.26 g, 17 mmol) and $CH_2Cl_2$ (75 mL).

Example 74

Production of N-[3-(3,5-bis(trifluoromethyl)benzyloxy)-2-phenylpropyl]-3-pyridin-3-ylacrylamide [Compound 46]

In the same manner as in the case of synthesis of Compound 30, Compound 46 (7.29 g, 96%) was produced as crystals from 3-pyridin-3-ylacryllic acid (2.54 g, 17 mmol), the compound produced in Example 17 (6.21 g, 15 mmol), triethylamine (2.4 mL, 17 mmol), WSC.HCl (3.26 g, 17 mmol) and CH$_2$Cl$_2$ (75 mL).

Example 75

Production of N-[3-(3,5-bis(trifluoromethyl)benzyloxy)-2-(4-fluorophenyl)propyl]-3-pyridin-3-ylacrylamide [Compound 47]

In the same manner as in the case of synthesis of Compound 30, Compound 47 (7.66 g, 97%) was produced as crystals from 3-pyridin-3-ylacryllic acid (2.54 g, 17 mmol), the compound produced in Example 18 (6.48 g, 15 mmol), triethylamine (2.4 mL, 17 mmol), WSC.HCl (3.26 g, 17 mmol) and CH$_2$Cl$_2$ (75 mL).

Example 76

Production of N-[3-(3,4-bis(trifluoromethyl)benzyloxy)-2-phenylpropyl]-3-pyridin-4-ylpropionamide [Compound 48]

Compound 45 (4.00 g, 7.8 mmol) was dissolved in ethanol (100 mL), a 5% Pd-carbon catalyst (0.5 g) was added thereto and the mixture was stirred for 20 hours in a hydrogen atmosphere. After the catalyst was filtered off, the filtrate was evaporated in vacuo and the crystals separated out therefrom were filtered after addition of petroleum ether to give the Compound 48 (2.61 g, 66%).

Example 77

Production of N-[3-(3,5-bis(trifluoromethyl)benzyloxy)-2-phenylpropyl]-3-pyridin-3-ylpropionamide [Compound 49]

In the same manner as in the case of synthesis of Compound 48, Compound 49 (3.61 g, 90%) was produced as crystals from Compound 46 (4.00 g, 7.8 mmol), 5% Pd-carbon catalyst (0.5 g) and ethanol (100 mL).

Example 78

Production of N-[3-(3,5-bis(trifluoromethyl)benzyloxy)-2-(4-fluorophenyl)propyl]-3-pyridin-3-ylpropionamide [Compound 50]

In the same manner as in the case of synthesis of Compound 48, Compound 50 (3.58 g, 89%) was produced as crystals from Compound 47 (4.00 g, 7.6 mmol), 5% Pd-carbon catalyst (0.5 g) and ethanol (100 mL).

Example 79

Production of N-[3-(3,5-bis(trifluoromethyl)benzyloxy)-2-phenylpropyl]-3-(1-oxypyridin-4-yl)propionamide [Compound 51]

In the same manner as in the case of synthesis of Compound 39, Compound 51 (1.29 g, 79%) was produced as crystals from Compound 48 (1.60 g, 3.1 mmol), MCPBA (0.74 g, 4.3 mmol) and chloroform (30 mL).

Example 80

Production of N-[3-(3,5-bis(trifluoromethyl)benzyloxy)-2-phenylpropyl]-3-(1-oxypyridin-3-yl)propionamide [Compound 52]

In the same manner as in the case of synthesis of Compound 39, Compound 52 (2.25 g, 91%) was produced as crystals from Compound 49 (2.41 g, 4.7 mmol), MCPBA (1.14 g, 6.6 mmol) and chloroform (50 mL).

Example 81

Production of N-[3-(3,5-bis(trifluoromethyl)benzyloxy)-2-phenylpropyl]-3-(1-oxypyridin-4-yl)acrylamide [Compound 53]

In the same manner as in the case of synthesis of Compound 39, Compound 53 (1.63 g, 91%) was produced as crystals from Compound 45 (1.75 g, 3.4 mmol), MCPBA (0.85 g, 4.9 mmol) and chloroform (40 mL).

Example 82

Production of N-[3-(3,5-bis(trifluoromethyl)benzyloxy)-2-phenylpropyl]-3-(1-oxypyridin-3-yl)acrylamide [Compound 54]

In the same manner as in the case of synthesis of Compound 39, Compound 54 (1.70 g, 95%) was produced as crystals from Compound 46 (1.75 g, 3.4 mmol), MCPBA (0.85 g, 4.9 mmol) and chloroform (40 mL).

Example 83

Production of N-[3-(3,5-bis(trifluoromethyl)benzyloxy)-2-(4-fluorophenyl)propyl]-3-(1-oxypyridin-3-yl)acrylamide [Compound 55]

In the same manner as in the case of synthesis of Compound 39, Compound 55 (1.81 g, 95%) was produced as crystals from Compound 47 (1.85 g, 3.5 mmol), MCPBA (0.85 g, 4.9 mmol) and chloroform (40 mL).

Example 84

Production of N-[3-(3,5-bis(trifluoromethyl)benzyloxy)-2-phenylpropyl]-4-hydroxybenzamide [Compound 56]

In the same manner as in the case of synthesis of Compound 30, a residue was given from 4-hydroxybenzoic acid (0.33 g, 2.4 mmol), the compound produced in Example 17 (0.83 g, 2.0 mmol), triethylamine (0.28 mL, 2.0 mmol), WSC.HCl (0.46 g, 2.4 mmol) and CH$_2$Cl$_2$ (10 mL). The oily residue was crystallized from petroleum ether to give the Compound 56 (0.61 g, 61%).

Example 85

Production of N-[3-(3,4-bis(trifluoromethyl)benzyloxy)-2-phenylpropyl]-4-fluorobenzamide [Compound 57]

A solution of 4-fluorobenzoyl chloride (1.2 mL, 10 mmol) in CH$_2$Cl$_2$ (20 mL) was dropped into a solution of the compound produced in Example 17 (3.31 g, 8.0 mmol) and triethylamine (2.8 mL, 20 mmol) in CH$_2$Cl$_2$ (50 mL) during 30 minutes under cooling with ice. After the solvent was evaporated therefrom in vacuo, water was added to the residue and the mixture was extracted with ethyl acetate. The organic layers were combined, washed with water and a saturated saline solution and dried over anhydrous sodium sulfate. The residual oily product produced by evaporation of the solvent therefrom in vacuo was crystallized from petroleum ether to give the Compound 57 (3.76 g, 94%).

Example 86

Production of N-[3-(3,5-Bis(trifluoromethyl)benzyloxy)-2-phenylpropyl]-4-dimethylaminobenzamide [Compound 58]

In the same manner as in the case of synthesis of Compound 30, a residue was given from 4-dimethylaminobenzoic acid (0.43 g, 2.5 mmol), the compound produced in Example 17 (1.03 g, 2.5 mmol), triethylamine (0.36 mL, 2.6 mmol), WSC.HCl (0.50 g, 2.6 mmol) and CH$_2$Cl$_2$ (25 mL). The oily residue was crystallized from petroleum ether to give the Compound 58 (1.08 g, 82%).

Example 87

Production of N-[3-(3,4-bis(trifluoromethyl)benzyloxy)-2-phenylpropyl]-4-diethylaminobenzamide hydrochloride [Compound 59]

An oily product was produced from 4-diethylaminobenzoic acid (0.50 g, 2.6 mmol), the compound produced in Example 17 (1.03 g, 2.5 mmol), triethylamine (0.36 mL, 2.6 mmol), WSC.HCl (0.50 g, 2.6 mmol) and CH$_2$Cl$_2$ (25 mL) according to the same manner as in Example 30. To this was added 4 mol/L hydrogen chloride/dioxane (5 mL; 20 mmol of HCl), the solvent and an excessive hydrogen chloride were evaporated therefrom in vacuo and the resulting residue was crystallized from petroleum ether to give the Compound 59 (0.96 g, 65%).

Example 88

Production of N-[2-(3,4-bis(trifluoromethyl)benzyloxy)-2-phenylpropyl]terephthalic acid [Compound 60]

Compound 60 (0.89 g, 83%) was produced as an oily product from monomethyl terephthalate (0.43 g, 2.4 mmol), the compound produced in Example 17 (0.83 g, 2.0 mmol), triethylamine (0.28 mL, 2.0 mmol), WSC.HCl (0.46 g, 2.4 mmol) and CH$_2$Cl$_2$ (10 mL) according to the same manner as in Example 30. Compound 66 (0.81 g, 1.5 mmol) and sodium hydroxide (0.12 g, 3.0 mmol) were added to a mixed solvent of ethanol (8.0 mL) and water (8.0 mL) followed by stirring for 20 hours at room temperature. After evaporation of the solvents therefrom in vacuo, 2 mol/L hydrochloric acid was added to the resulting oily residue and the oily product separated out therefrom was extracted with ethyl acetate. The organic layers were combined and dried over anhydrous sodium sulfate and the solvent was evaporated therefrom in vacuo. The resulting residual oily product was crystallized from petroleum ether to give Compound 60 (0.71 g, 90%).

Example 89

Production of 4-amino-N-[3-(3,5-bis(trifluoromethyl)benzyloxy)-2-ph enylpropyl]benzamide hydrochloride [Compound 61]

Compound 67 (1.10 g, 923%) was produced as an oily product from 4-tert-butoxycarbonylaminobenzoic acid (0.57 g, 2.4 mmol), the compound produced in Example 17 (0.83 g, 2.0 mmol), triethylamine (0.28 mL, 2.0 mmol), WSC.HCl (0.46 g, 2.4 mmol) and CH$_2$Cl$_2$ (10 mL) according to the same manner as in Example 30. After that, Compound 67 (0.95 g, 1.6 mmol) was dissolved in dioxane (2.4 mL), 4 mol/L hydrogen chloride/dioxane (2.4 mL) was added thereto and the mixture was stirred for 20 hours at room temperature. The crystals produced after evaporation of the solvent therefrom in vacuo were filtered from petroleum ether to give Compound 61 (0.55 g, 65%).

Example 90

Production of 4-Amino-N-[3-(3,5-bis(trifluoromethyl)benzyloxy)-2-(4-fluorophenyl)propyl]benzamide hydrochloride [Compound 62]

Compound 68 (1.20 g, 98%) was produced as an oily product from 4-tert-butoxycarbonylaminobenzoic acid (0.57 g, 2.4 mmol), the compound produced in Example 18 (0.86 g, 2.0 mmol), triethylamine (0.28 mL, 2.0 mmol), WSC.HCl (0.46 g, 2.4 mmol) and CH$_2$Cl$_2$ (10 mL) according to the same manner as in Example 30. In the same manner as in the case of synthesis of Compound 61, Compound 62 (1.06 g, 96%) was produced from Compound 68 (1.20 g, 2.0 mmol), 4 mol/L hydrogen chloride/dioxane (3.0 mL) and dioxane (3.0 mL).

Example 91

Production of 4-Aminomethyl-N-[3-(3,5-bis(trifluoromethyl)benzyloxy)-2-phenylpropyl]benzamide hydrochloride [Compound 63]

Compound 69 (1.05 g, 86%) was produced as an oily product from 4-tert-butoxycarbonylaminomethylbenzoic acid (0.60 g, 2.4 mmol), the compound produced in Example 17 (0.83 g, 2.0 mmol), triethylamine (0.28 mL, 2.0 mmol), WSC.HCl (0.46 g, 2.4 mmol) and CH$_2$Cl$_2$ (10 mL) according to the same manner as in Example 30. In the same manner as in the case of synthesis of Compound 61, Compound 63 (0.55 g, 59%) was produced from Compound 69 (1.04 g, 1.7 mmol), 4 mol/L hydrogen chloride/dioxane (2.6 mL) and dioxane (2.6 mL).

Example 92

Production of N-[3-(3,5-bis(trifluoromethyl)benzyloxy)-2-phenylpropyl]-4-pyrrolidin-1-ylmethylbenzamide hydrochloride [Compound 64]

Compound 70 (2.25 g, 71%) was produced as an oily product from 4-chloromethylbenzoic acid (1.23 g, 7.2 mmol), the compound produced in Example 17 (2.48 g, 6.0 mmol), triethylamine (0.83 mL, 6.0 mmol), WSC.HCl (1.38 g, 7.2 mmol) and CH$_2$Cl$_2$ (20 mL) according to the same manner as Example 30. Compound 70 (1.06 g, 2.0 mmol), pyrrolidine (0.25 mL, 3.0 mmol), potassium carbonate (0.55 g, 4.0 mmol) and potassium iodide (0.1 g) were added to DMF (15 mL) and the mixture was stirred for 20 hours at room temperature. Water was added to the reaction mixture followed by extracting with ethyl acetate. The organic layers were combined, washed with water and a saturated saline solution and dried over anhydrous sodium sulfate. The residual oily product produced by evaporation of the solvent therefrom in vacuo was crystallized from petroleum ether to give Compound 64 (1.12 g, 93%).

Example 93

Production of N-[3-(3,5-bis(trifluoromethyl)benzyloxy)-2-phenylpropyl]-4-piperidin-1-ylmethylbenzamide hydrochloride [Compound 65]

Compound 65 (0.97 g, 79%) was produced from Compound 70 (1.06 g, 2.0 mmol), piperidine (0.25 mL, 3.0 mmol), potassium carbonate (0.55 g, 4.0 mmol), potassium iodide (0.1 g) and DMF (15 mL) according to the same manner as in the case of synthesis of Compound 64.

Example 94

Production of N-{2-[3-(3,5-bis(trifluoromethyl)benzyloxy)-2-phenylpropylcarbamoyl]ethyl}carbamate [Compound 73]

Compound 73 (1.32 g, 100%) was produced from N-Boc-β-Alanine (0.55 g, 2.9 mmol), the compound produced in Example 17 (0.99 g, 2.4 mmol), triethylamine (0.40 mL, 2.9 mmol), WSC.HCl (0.56 g, 2.9 mmol) and $CH_2Cl_2$ (10 mL) in the same manner as Example 29.

Example 95

Production of 3-amino-N-[3-(3,5-bis(trifluoromethyl)benzyloxy)-2-ph enylpropyl]propionamide hydrochloride [Compound 74]

Compound 73 (1.32 g, 2.4 mmol) produced in Example 95 was dissolved in dioxane (4 mL) and 4 mol/L hydrogen chloride/dioxane (4 mL) was added thereto at room temperature. After the mixture was stirred for 20 hours, the solvent was evaporated therefrom in vacuo. Ether was added to the resulting residue to crystallize whereupon Compound 74 (1.10 g, 95%) was produced.

Example 96

Production of tert-butyl N-{2-[3-(3,5-bis(trifluoromethyl)benzyloxy)-2-(4-fluorophenyl)propylcarbamoyl]ethyl}carbamate [Compound 75]

Compound 75 (1.06 g, 94%) was produced from N-Boc-β-Alanine (0.45 g, 2.4 mmol), the compound produced in Example 18 (0.86 g, 2.0 mmol), triethylamine (0.28 mL, 2.4 mmol), WSC.HCl (0.46 g, 2.4 mmol) and $CH_2Cl_2$ (10 mL) in the same manner as Example 29.

Example 97

Production of 3-Amino-N-[3-(3,5-bis(trifluoromethyl)benzyloxy)-2-(4-fluorophenyl)propyl]propionamide hydrochloride [Compound 76]

In the same manner as in the case of synthesis of Compound 95, Compound 76 (0.43 g, 57%) was produced from Compound 75 (0.85 g, 1.5 mmol), 4 mol/L hydrogen chloride/dioxane (2.3 mL) and dioxane (2.3 mL).

Example 98

Production of tert-butyl {4-[3-(3,5-bis(trifluoromethyl)benzyloxy)-2-phenylpropylcarbamoyl]butyl}carbamate [Compound 77]

Compound 77 (1.41 g, 100%) was produced from N-Boc-5-aminopentanoic acid (0.63 g, 2.9 mmol), the compound produced in Example 17 (0.99 g, 2.4 mmol), triethylamine (0.40 mL, 2.9 mmol), WSC.HCl (0.56 g, 2.9 mmol) and $CH_2Cl_2$ (10 mL) in the same manner as Example 29.

Example 99

Production of N-[3-(3,5-bis(trifluoromethyl)benzyloxy)-2-phenylpropyl]-5-aminopentanoicamide hydrochloride [Compound 78]

In the same manner as in the case of synthesis of Compound 95, Compound 78 (1.15 g, 93%) was produced from Compound 77 (1.38 g, 2.4 mmol), 4 mol/L hydrogen chloride/dioxane (4.8 mL) and dioxane (4.8 mL).

Example 100

Production of tert-butyl {4-[3-(3,5-bis(trifluoromethyl)benzyloxy)-2-phenylpropylcarbamoyl]piperidine-1-yl}acetate [Compound 79]

A mixture of Compound 4 produced in Example 32 (1.26 g, 2.4 mmol), tert-butyl bromoacetate (0.38 mL, 2.6 mmol), potassium carbonate (1.00 g, 7.2 mmol) and DMF (10 mL) was stirred for 20 hours at room temperature. Water was added to the reaction mixture followed by extracting with ethyl acetate. The organic layers were combined, washed with water and a saturated saline solution and dried over anhydrous sodium sulfate. The solvent was evaporated therefrom in vacuo to give Compound 79 (1.34 g, 93%).

Example 101

Production of {4-[3-(3,5-bis(trifluoromethyl)benzyloxy)-2-phenylpropylcarbamoyl]piperidin-1-yl}acetic acid hydrochloride [Compound 80]

In the same manner as in the case of synthesis of Compound 95, Compound 80 (1.18 g, 92%) was produced from Compound 79 (1.33 g, 2.2 mmol) and 4 mol/L hydrogen chloride/dioxane (4.4 mL).

Example 102

Production of Ethyl N-[3-(3,5-bis(trifluoromethyl)benzyloxy)-2-phenylpropyl]malonamate [Compound 81]

Compound 81 (1.99 g, 90%) was produced from the compound produced in Example 17 (1.86 g, 4.5 mmol), ethyl malonate (0.71 g, 5.4 mmol), triethylamine (0.66 mL, 4.5 mmol), WSC.HCl (1.03 g, 5.4 mmol) and CH$_2$Cl$_2$ (10 mL) in the same manner as Example 29.

Example 103

Production of N-[3-(3,5-bis(trifluoromethyl)benzyloxy)-2-phenylpropyl]malonamate [Compound 82]

A mixture of Compound 81 (0.59 g, 1.2 mmol), sodium hydroxide (0.10 g, 2.4 mmol) and water (6 mL) was stirred for 20 hours at room temperature. After the solvent was evaporated therefrom in vacuo, a 2 mol/L hydrochloric acid was added to the resulting residual oily product and the oily product separated out therefrom was extracted with ethyl acetate. The organic layers were combined and dried over anhydrous sodium sulfate and the solvent was evaporated therefrom in vacuo. The resulting residual oily product was crystallized from petroleum ether to give the Compound 82 (0.50 g, 90%).

Example 104

Production of N-[3-(3,5-bis(trifluoromethyl)benzyloxy)-2-phenylpropyl]pyrazine-2-carboxamide [Compound 83]

Compound 83 (1.06 g, 45%) was produced from the compound produced in Example 17 (2.00 g, 4.8 mmol), pirazinecarboxylic acid (0.60 g, 4.8 mmol), triethylamine (0.68 mL, 4.8 mmol), WSC.HCl (0.92 g, 4.8 mmol) and CH$_2$Cl$_2$ (10 mL) in the same manner as Example 29.

Example 105

Production of Phenyl [3-(3,5-bis(trifluoromethyl) benzyloxy)-2-phenylpropyl]carbamate [Compound 84]

Compound 84 (1.42 g, 95%) was produced from the compound produced in Example 17 (1.24 g, 3 mmol), phenyloxycarbonylchloride (0.42 g, 3.3 mmol), triethylamine (0.92 mL, 6.6 mmol) and CH$_2$Cl$_2$ (15 mL) in the same manner as Example 29.

Example 106

Production of tert-butyl 4-{3-[3-(3,5-bis(trifluoromethyl)benzyloxy)-2-phenylpropyl]ureido}piperidine-1-carboxylate [Compound 85]

Compound 84 produced in Example 77 (0.85 g, 1.7 mmol), tert-butyl 4-aminopiperidin-1-carboxylate (0.34 g, 1.7 mmol) and triethylamine (0.28 mL, 2.0 mmol) were dissolved in isopropyl alcohol and heated to reflux for 20 hours. After the solvent was evaporated therefrom in vacuo, the residue was purified by a column chromatography (toluene:acetone=4:1) to give Compound 85 (0.74 g, 72%).

Example 107

Production of 1-[3-(3,5-bis(trifluoromethyl)benzyloxy)-2-phenylpropyl]-3-piperidin-4-ylurea hydrochloride [Compound 86]

Compound 86 (0.43 g, 66%) was produced from Compound 85 (0.72 g, 1.2 mmol), 4 mol/L hydrogen chloride/ dioxane (1.8 mL) and dioxane (1.8 mL), in the same manner as Example 96.

Example 108

Production of tert-butyl {4-[3-(3,5-bis(trifluoromethyl)benzyloxy)-2-phenylpropylcarbamoyl] cyclohexyl}carbamate [Compound 87]

Compound 87 (1.05 g, 87%) was produced from the compound produced in Example 17 (0.83 g, 2.0 mmol), 4-tert-butyloxycarbonylaminocyclohexanecarboxylic acid (0.58 g, 2.4 mmol), triethylamine (0.28 mL, 2.0 mmol), WSC.HCl (0.46 g, 2.4 mmol) and CH$_2$Cl$_2$ (15 mL) in the same manner as Example 29.

Example 109

Production of 4-Aminocyclohexanecarboxylic acid [3-(3,5-bis(trifluoromethyl)benzyloxy)-2-phenylpropyl]amide hydrochloride [Compound 88]

Compound 88 (0.90 g, 98%) was produced from Compound 87 (1.02 g, 1.7 mmol), 4 mol/L hydrogen chloride/ dioxane (2.6 mL) and dioxane (2.6 mL), in the same manner as Example 95.

Example 110

Production of Ethyl 1-{[3-(3,5-bis(trifluoromethyl) benzyloxy)-2-phenylpropylcarbamoyl] methyl}piperidine-4-carboxyate [Compound 89]

Compound 89 (0.91 g, 79%) was produced from the compound produced in Example 17 (0.83 g, 2.0 mmol), 1-carboxymethylpiperidine-4-carboxylate (0.60 g, 2.4 mmol), triethylamine (0.61 mL, 4.4 mmol), WSC.HCl (0.46 g, 2.4 mmol) and CH$_2$Cl$_2$ (15 mL) in the same manner as Example 29.

Example 111

Production of 1-{[3-(3,5-bis(trifluoromethyl)benzyloxy)-2-phenylpropylcarbamoyl]methyl}piperidine-4-carboxylic acid [Compound 90]

Compound 90 (0.47 g, 54%) was produced from Compound 89 (0.92 g, 1.6 mmol), sodium hydroxide (0.13 g, 3.2 mmol), ethanol (6 mL) and water (6 mL) in the same manner as Example 104.

Example 112

Production of N-[3-(3,5-bis(trifluoromethyl)benzyloxy)-2-phenylpropyl]-2-[1,4']bipiperidinyl-1'-ylacetamide dihydrochloride [Compound 91]

Compound 91 (1.45 g, 92%) was produced as a hygroscopic amorphous solid from [1,4']bipiperadin-1'-ylacetic acid dihydrochloride (0.87 g, 2.9 mmol), the compound produced in Example 17 (0.99 g, 2.4 mmol), triethylamine (1.1 mL, 8.2 mmol), WSC.HCl (0.56 g, 2.9 mmol), 4 mol/L hydrogen chloride/dioxane (1.0 mL, hydrogen chloride 4 mmol) and CH$_2$Cl$_2$ (15 mL) in the same manner as Example 30.

Example 113

Production of N-[3-(3,5-bis(trifluoromethyl)benzyloxy)-2-phenylpropyl]-N-methylpiperidine-4-carboxamide hydrochloride [Compound 93]

In the same manner as Example 29, tert-butyl 4-{[3-(3,5-bis(trifluoromethyl)benzyloxy)-2-phenylpropyl]

methylcarbamoyl}piperidine-1-carboxylate [Compound 92] was produced from N-tert-butyloxycarbonylisonipecotinic acid (0.66 g, 2.9 mmol), the compound produced in Example 21 (1.03 g, 2.4 mmol), triethylamine (0.40 mL, 2.9 mmol), WSC.HCl (0.56 g, 2.9 mmol) and $CH_2Cl_2$ (10 mL). Compound 93 (0.61 g, 67%) was produced from Compound 92 (1.02 g, 1.7 mmol), 4 mol/L hydrogen chloride/dioxane (3.4 mL) and dioxane (3.4 mL) in the same manner as Example 95.

Example 114

Production of N-[3-(3,5-bis(trifluoromethyl)benzyloxy)-2-(4-fluorophenyl)propyl]-N-methylpiperidine-4-carboxamide hydrochloride [Compound 95]

In the same manner as Example 29, tert-butyl 4-{[3-(3,5-bis(trifluoromethyl)benzyloxy)-2-(4-fluorophenyl)propyl]methylcarbamoyl}piperidine-1-carboxylate [Compound 94] was produced from the compound produced in Example 22 (0.89 g, 2.0 mmol), N-tert-butyloxycarbonylisonipecotinic acid (0.55 g, 2.4 mmol), triethylamine (0.28 mL, 2.4 mmol), WSC.HCl (0.46 g, 2.4 mmol) and $CH_2Cl_2$ (10 mL). Compound 95 (0.94 g, 99%) was produced from Compound 94 (1.06 g, 1.7 mmol), 4 mol/L hydrogen chloride/dioxane (3.4 mL) and dioxane (3.4 mL) in the same manner as Example 95.

Example 115

Production of N-[3-(3,5-bis(trifluoromethyl)benzyloxy)-2-phenylpropyl]-N-methyl-1-methylpiperidine-4-carboxamide hydrochloride [Compound 96]

Compound 96 (0.58 g, 44%) was produced as a hygroscopic amorphous solid from N-methylpiperidine-4-carboxylic acid (0.41 g, 2.9 mmol), the compound produced in Example 21 (1.03 g, 2.4 mmol), triethylamine (0.40 mL, 2.9 mmol), WSC.HCl (0.56 g, 2.9 mmol), 4 mol/L hydrogen chloride/dioxane (1.0 mL, hydrogen chloride 4 mmol) and $CH_2Cl_2$ (10 mL) in the same manner as Example 30.

Example 116

Production of N-[3-(3,5-bis(trifluoromethyl)benzyloxy)-2-(4-fluorophenyl)propyl]-N-methylpiperidine-4-carboxamide hydrochloride [Compound 97]

Compound 97 (1.10 g, 96%) was produced as a hygroscopic amorphous solid from N-methylpiperidine-4-carboxylic acid (0.34 g, 2.4 mmol), the compound produced in Example 22 (0.89 g, 2.0 mmol), triethylamine (0.28 mL, 2.4 mmol), WSC.HCl (0.46 g, 2.4 mmol), 4 mol/L hydrogen chloride/dioxane (1.0 mL, hydrogen chloride 4 mmol) and $CH_2Cl_2$ (10 mL) in the same manner as Example 30.

Example 117

Production of N-[3-(3,5-bis(trifluoromethyl)benzyloxy)-2-(4-fluorophenyl)propyl]-N-methylisonicotinamide [Compound 98]

Compound 98 (0.87 g, 85%) was produced from isonicotinic acid (0.30 g, 2.4 mmol), the compound produced in Example 22 (0.89 g, 2.0 mmol), triethylamine (0.28 mL, 2.4 mmol), WSC.HCl (0.46 g, 2.4 mmol) and $CH_2Cl_2$ (10 mL) in the same manner as Example 29.

Example 118

Production of N-[3-(3,5-bis(trifluoromethyl)benzyloxy)-2-phenylpropyl]-N-methyl-1-oxyisonicotinamide [Compound 99]

Compound 99 (0.66 g, 64%) was produced from 1-oxyisonicotinic acid (0.33 g, 2.4 mmol), the compound produced in Example 21 (0.86 g, 2.0 mmol), triethylamine (0.28 mL, 2.4 mmol), WSC.HCl (0.46 g, 2.4 mmol) and $CH_2Cl_2$ (10 mL) in the same manner as Example 29.

Example 119

Production of N-[3-(3,5-bis(trifluoromethyl)benzyloxy)-2-(4-fluorophenyl)propyl]-2-hydroxy-N-methylisonicotinamide [Compound 100]

Compound 100 (0.34 g, 32%) was produced from 2-hydroxyisonicotinic acid (0.33 g, 2.4 mmol), the compound produced in Example 22 (0.89 g, 2.0 mmol), triethylamine (0.28 mL, 2.4 mmol), WSC.HCl (0.46 g, 2.4 mmol) and $CH_2Cl_2$ (10 mL) in the same manner as Example 29.

Example 120

Production of N-[3-(3,5-bis(trifluoromethyl)benzyloxy)-2-phenylpropyl]-N-methyl-3-aminopropionamide hydrochloride [Compound 102]

tert-Butyl N-(2-{[3-(3,5-bis(trifluoromethyl)benzyloxy)-2-phenylpropyl]methylcarbamoyl}ethyl)carbamate (1.06 g, 1.9 mmol) [Compound 101] was produced from 3-N-tert-butyloxycarbonylaminopropionic acid (0.55 g, 2.9 mmol), the compound produced in Example 21 (1.03 g, 2.4 mmol), triethylamine (0.40 mL, 2.9 mmol), WSC.HCl (0.56 g, 2.9 mmol) and $CH_2Cl_2$ (10 mL) in the same manner as Example 29. In the same manner as Example 95, Compound 102 (0.95 g, 99%) was produced from Compound 101 (1.06 g, 1.9 mmol), 4 mol/L hydrogen chloride/dioxane (3.8 mL) and dioxane (3.8 mL).

Example 121

Production of 3-Amino-N-[3-(3,5-bis(trifluoromethyl)benzyloxy)-2-(4-fluorophenyl)propyl]-N-methylpropionamide hydrochloride [Compound 104]

N-(2-{[3-(3,5-bis(trifluoromethyl)benzyloxy)-2-(4-fluorophenyl)propyl]methylcarbamoyl}ethyl)carbamic acid tert-butyl ester (1.08 g, 93%) [Compound 103] was produced from 3-N-tert-butyloxycarbonylaminopropionic acid (0.45 g, 2.4 mmol), the compound produced in Example 22 (0.89 g, 2.0 mmol), triethylamine (0.28 mL, 2.4 mmol), WSC.HCl (0.46 g, 2.4 mmol) and $CH_2Cl_2$ (10 mL) in the same manner as Example 29. In the same manner as Example 95, Compound 104 (0.94 g, 99%) was produced from Compound 103 (1.08 g, 1.9 mmol), 4 mol/L hydrogen chloride/dioxane (2.9 mL) and dioxane (2.9 mL).

Example 122

Production of 5-Aminopentanoic acid [3-(3,5-bis(trifluoromethyl)benzyloxy)-2-phenylpropyl]methylamide hydrochloride [Compound 106]

tert-Butyl (4-{[3-(3,5-bis(trifluoromethyl)benzyloxy)-2-phenylpropyl]methylcarbamoyl}butyl)carbamate (1.34 g, 95%) [Compound 105] was produced from 5-N-tert-butyloxycarbonylaminopentanoic acid (0.63 g, 2.9 mmol), the compound produced in Example 21 (1.03 g, 2.4 mmol), triethylamine (0.40 mL, 2.9 mmol), WSC.HCl (0.56 g, 2.9 mmol) and $CH_2Cl_2$ (10 mL) in the same manner as Example 29. In the same manner as Example 95, Compound 106 (1.06 g, 99%) was produced from Compound 105 (1.34 g, 1.9 mmol), 4 mol/L hydrogen chloride/dioxane (5.0 mL) and dioxane (5.0 mL).

Example 123

Production of 1-Methylpiperidine-4-carboxylic acid [2-(3,5-bis(trifluoromethyl)benzyloxymethyl)-3,3-diphenylpropyl]methylamide hydrochloride [Compound 107]

Compound 107 (1.30 g, 100%) was produced as a hygroscopic amorphous solid from [2-(3,5-bis(trifluoromethyl)benzyloxymethyl)-3,3-diphenylpropyl]methylamine hydrochloride (1.04 g, 2.0 mmol), N-methyl isonipecotinic acid (0.34 g, 2.4 mmol), triethylamine (0.28 mL, 2.4 mmol), WSC.HCl (0.46 g, 2.4 mmol), 4 mol/L hydrogen chloride/dioxane (1.0 mL, hydrogen chloride 4 mmol) and $CH_2Cl_2$ (10 mL) in the same manner as Example 30.

Example 124

Production of Piperidine-4-carboxylic acid [3-(3,5-dimethylbenzyloxy)-2-phenylpropyl]amide hydrochloride [Compound 109]

tert-Butyl 4-[3-(3,5-dimethylbenzyloxy)-2-phenylpropylcarbamoyl]piperidine-1-carboxylate was produced (1.44 g, 100%) [Compound 108] was produced from the compound produced in Example 24 (0.92 g, 3.0 mmol), N-tert-butyloxycarbonylisonipecotinic acid (0.83 g, 3.6 mmol), triethylamine (0.42 mL, 3.0 mmol), WSC.HCl (0.69 g, 3.6 mmol) and $CH_2Cl_2$ (10 mL) in the same manner as Example 29. In the same manner as Example 95, Compound 109 (1.14 g, 91%) was produced from Compound 108 (1.44 g, 3.0 mmol), 4 mol/L hydrogen chloride/dioxane (4.5 mL) and dioxane (4.5 mL).

Example 125

Production of 1-Methylpiperidine-4-carboxylic acid [3-(3,5-dimethylbenzyloxy)-2-phenylpropyl]amide [Compound 110]

Compound 110 (1.02 g, 86%) was produced from the compound produced in Example 24 (0.92 g, 3.0 mmol), N-methyl isonipecotinic acid (0.52 g, 3.6 mmol), triethylamine (0.42 mL, 3.0 mmol), WSC.HCl (0.69 g, 3.6 mmol) and $CH_2Cl_2$ (10 mL) in the same manner as Example 29.

Example 126

Production of 3-Amino-N-[3-(3,5-dimethylbenzyloxy)-2-phenylpropyl]propionamide hydrochloride [Compound 112]

tert-Butyl {2-[3-(3,5-dimethylbenzyloxy)-2-phenylpropylcarbamoyl]ethyl}carbamate (1.17 g, 89%) [Compound 111] was produced from the compound produced in Example 24 (0.92 g, 3.0 mmol), 3-N-tert-butyloxycarbonylpropionic acid (0.68 g, 3.6 mmol), triethylamine (0.42 mL, 3.0 mmol), WSC.HCl (0.69 g, 3.6 mmol) and $CH_2Cl_2$ (10 mL) in the same manner as Example 29. In the same manner as Example 95, Compound 112 (0.94 g, 100%) was produced from Compound III (1.10 g, 2.5 mmol), 4 mol/L hydrogen chloride/dioxane (4.5 mL) and dioxane (4.5 mL).

Example 127

Production of Piperidine-4-carboxylic acid [3-(4-fluorobenzyloxy)-2-phenylpropyl]amide hydrochloride [Compound 114]

tert-Butyl 4-[3-(4-fluorobenzyloxy)-2-phenylpropylcarbamoyl]piperidine-1-carboxylate (1.21 g, 86%) [Compound 113] was produced from the compound produced in Example 23 (0.89 g, 3.0 mmol), N-tert-butyloxycarbonylisonipecotinic acid (0.83 g, 3.6 mmol), triethylamine (0.42 mL, 3.0 mmol), WSC.HCl (0.69 g, 3.6 mmol) and $CH_2Cl_2$ (10 mL) in the same manner as Example 29. In the same manner as Example 95, Compound 114 (0.92 g, 87%) was produced from Compound III (1.10 g, 2.5 mmol), 4 mol/L hydrogen chloride/dioxane (4.5 mL) and dioxane (4.5 mL).

Example 128

Production of 1-Methylpiperidine-4-carboxylic acid [3-(4-fluorobenzyloxy)-2-phenylpropyl]amide hydrochloride [Compound 115]

Compound 115 (0.82 g, 65%) was produced as a hygroscopic amorphous solid from the compound produced in Example 23 (0.89 g, 3.0 mmol), N-methylisonipecotinic acid (0.52 g, 3.6 mmol), triethylamine (0.42 mL, 3.0 mmol), WSC.HCl (0.69 g, 3.6 mmol), 4 mol/L hydrogen chloride/dioxane (1.0 mL, hydrogen chloride 4 mmol) and $CH_2Cl_2$ (10 mL) in the same manner as Example 30.

Example 129

Production of N-[3-(4-Fluorobenzyloxy)-2-phenylpropyl]isonicotinamide [Compound 116]

Compound 116 (0.96 g, 88%) was produced from the compound produced in Example 23 (0.89 g, 3.0 mmol), isonicotinic acid (0.44 g, 3.6 mmol), triethylamine (0.42 mL, 3.0 mmol), WSC.HCl (0.69 g, 3.6 mmol) and $CH_2Cl_2$ (10 mL) in the same manner as Example 29.

Example 130

Production of N-[3-(4-Fluorobenzyloxy)-2-phenylpropyl]-1-oxyisonicotinamide [Compound 117]

Compound 117 (1.06 g, 93%) was produced from the compound produced in Example 23 (0.89 g, 3.0 mmol), 1-oxyisonicotinic acid (0.50 g, 3.6 mmol), triethylamine (0.42 mL, 3.0 mmol), WSC.HCl (0.69 g, 3.6 mmol) and $CH_2Cl_2$ (10 mL) in the same manner as Example 29.

Example 131

Production of 3-Amino-N-[3-(4-fluorobenzyloxy)-2-phenylpropyl]propionamide hydrochloride [Compound 119]

tert-Butyl {2-[3-(4-fluorobenzyloxy)-2-phenylpropylcarbamoyl]ethyl}carbamte (1.33 g, 100%) [Compound 118]

was produced from the compound produced in Example 23 (0.89 g, 3.0 mmol), 3-N-tert-butyloxycarbonylpropionic acid (0.68 g, 3.6 mmol), triethylamine (0.42 mL, 3.0 mmol), WSC.HCl (0.69 g, 3.6 mmol) and CH$_2$Cl$_2$ (10 mL) in the same manner as Example 29. In the same manner as Example 95, Compound 119 (1.10 g, 100%) was produced from Compound 118 (1.29 g, 3.0 mmol), 4 mol/L hydrogen chloride/dioxane (4.5 mL) and dioxane (4.5 mL).

Example 132

Production of N-[3-(3,4-Dichlorobenzyloxy)-2-phenylpropyl]-1-oxyisonicotinamide [Compound 120]

Compound 120 (0.52 g, 48%) was produced from the compound produced in Example 25 (0.87 g, 2.5 mmol), 1-oxyisonicotinic acid (0.42 g, 3.0 mmol), triethylamine (0.35 mL, 2.5 mmol), WSC.HCl (0.57 g, 3.0 mmol) and CH$_2$Cl$_2$ (10 mL) in the same manner as Example 29.

Example 133

Production of 4-Amino-N-[3-(3,4-dichlorobenzyloxy)-2-phenylpropyl]benzamide hydrochloride [Compound 122]

tert-Butyl {4-[3-(3,4-dichlorobenzyloxy)-2-phenylpropylcarbamoyl]phenyl}carbamate (1.31 g, 99%) [Compound 121] was produced from the compound produced in Example 25 (0.87 g, 2.5 mmol), tert-butyloxycarbonylaminobenzoic acid (0.71 g, 3.0 mmol), triethylamine (0.35 mL, 2.5 mmol), WSC.HCl (0.57 g, 3.0 mmol) and CH$_2$Cl$_2$ (10 mL) in the same manner as Example 29. In the same manner as Example 95, Compound 122 (1.16 g, 100%) was produced from Compound 121 (1.32 g, 3.0 mmol), 4 mol/L hydrogen chloride/dioxane (4.0 mL) and dioxane (4.0 mL).

Example 134

Production of N-[3-(3,5-Difluorobenzyloxy)-2-phenylpropyl]-1-oxyisonicotinamide [Compound 123]

Compound 123 (0.46 g, 46%) was produced from the compound produced in Example 26 (0.78 g, 2.5 mmol), 1-oxyisonicotinic acid (0.36 g, 2.6 mmol), triethylamine (0.36 mL, 2.6 mmol), WSC.HCl (0.50 g, 2.6 mmol) and CH$_2$Cl$_2$ (10 mL) in the same manner as Example 29.

Example 135

Production of 1-Oxy-N-[2-phenyl-3-(3-trifluoromethylbenzyloxy)pro pyl]isonicotinamide [Compound 124]

Compound 124 (0.49 g, 46%) was produced from the compound produced in Example 27 (0.86 g, 2.5 mmol), 1-oxyisonicotinic acid (0.36 g, 2.6 mmol), triethylamine (0.36 mL, 2.6 mmol), WSC.HCl (0.50 g, 2.6 mmol) and CH$_2$Cl$_2$ (10 mL) in the same manner as Example 29.

Example 136

Production of N-(3-benzyloxy-2-phenylpropyl)-1-oxyisonicotinamide [Compound 125]

Compound 125 (0.65 g, 72%) was produced from the compound produced in Example 28 (0.69 g, 2.5 mmol), 1-oxyisonicotinic acid (0.36 g, 2.6 mmol), triethylamine (0.36 mL, 2.6 mmol), WSC.HCl (0.50 g, 2.6 mmol) and CH$_2$Cl$_2$ (10 mL) in the same manner as Example 29.

$^1$H-NMR spectral data of the compounds of the present invention produced in the above Examples are shown in Tables 1 to 15. Unless otherwise mentioned in the data, measurement of the spectrum was carried out using a deuterated DMSO (DMSO-d$_6$) as a solvent.

TABLE 1

| Compound No. | $^1$H NMR spectrum |
|---|---|
| Compound 1 | 1.46-1.49 (m, 4H), 1.80-1.82 (m, 2H), 1.93-1.96 (m, 1H), 2.13 (s, 3H), 2.70-2.80 (m, 2H), 3.11-3.14 (m, 1H), 3.26-3.28 (m, 1H), 3.38-3.41 (m, 1H), 3.66-3.68 (m, 2H), 4.63 (s, 2H), 7.22-7.30 (m, 5H), 7.72 (t, J = 5.3 Hz, 1H), 7.87 (s, 2H), 7.98 (s, 1H). |
| Compound 2 | 1.70-1.84 (m, 4H), 2.23-2.25 (m, 1H), 2.65-2.69 (m, 3H), 2.81-2.87 (m, 2H), 3.14-3.18 (m, 2H), 3.32-3.45 (m, 3H), 3.66-3.69 (m, 2H), 4.61-4.67 (m, 2H), 7.08-7.11 (m, 2H), 7.26-7.28 (m, 2H), 7.84 (s, 2H), 7.99 (s, 2H), 10.08 (brs, 1H). |
| Compound 3 | 1.20-1.27 (m, 6H), 1.30-1.90 (m, 4H), 2.07-2.10 (m, 1H), 2.81-3.18 (m, 4H), 3.32-3.46 (m, 3H), 3.69-3.72 (m, 2H), 7.21-7.31 (m, 5H), 7.88-7.99 (m, 4H), 10.05 (brs, 1H). |
| Compound 4 | 1.63-1.70 (m, 4H), 2.30-2.34 (m, 1H), 2.78-2.81 (m, 2H), 3.14-3.21 (m, 3H), 3.32-3.34 (m, 1H), 3.41-3.44 (m, 1H), 3.66-3.71 (m, 2H), 4.64 (s, 2H), 7.22-7.31 (m, 5H), 7.88 (s, 2H), 7.94 (t, J = 5.7 Hz, 1H), 7.99 (s, 1H), 8.75 (brs, 1H). |
| Compound 5 | 1.59-1.69 (m, 4H), 2.29-2.34 (m, 1H), 2.77-2.81 (m, 2H), 3.14-3.20 (m, 3H), 3.33-3.42 (m, 2H), 3.62-3.69 (m, 2H), 4.59-4.65 (m, 2H), 7.08-7.12 (m, 2H), 7.24-7.28 (m, 2H), 7.84 (s, 2H), 7.94 (brs, 1H), 7.99 (s, 1H), 8.51-8.55 (m, 1H), 8.90-8.92 (m, 1H). |
| Compound 6 | 3.29-3.37 (m, 1H), 3.50-3.57 (m, 1H), 3.63-3.70 (m, 1H), 3.76 (dd, J = 7.0, 9.5 Hz, 1H), 3.79 (dd, J = 5.9, 9.5 Hz, 1H), 4.64 and 4.68 (ABq, J = 14.3 Hz, 2H), 7.21-7.33 (m, 5H), 7.63 (d, J = 6.0 Hz, 2H), 7.88 (s, 2H), 7.98 (s, 1H), 8.67 (d, J = 6.0 Hz, 2H), 8.78 (t, J = 5.6 Hz, 1H). |
| Compound 7 | 3.33-3.35 (m, 1H), 3.52-3.56 (m, 1H), 3.62-3.65 (m, 1H), 3.72 (dd, J = 7.1, 9.5 Hz, 1H), 3.78 (dd, J = 5.7, 9.5 Hz, 1H), 4.65 and 4.67 (ABq, J = 13.7 Hz, 2H), 7.10-7.13 (m, 2H), |

TABLE 1-continued

| Compound No. | ¹H NMR spectrum |
| --- | --- |
| Compound 8 | 7.32-73.35 (m, 2H), 7.63 (d, J = 6.0 Hz, 2H), 7.85 (s, 2H), 7.98 (s, 1H), 8.67 (d, J = 6.0 Hz, 2H), 8.77 (t, J = 5.6 Hz, 1H). 3.10-3.37 (m, 1H), 3.33-3.58 (m, 1H), 3.65-3.72 (m, 1H), 3.77 (dd, J = 7.0, 9.5 Hz, 1H), 3.82 (dd, J = 5.8, 9.5 Hz, 1H), 4.65 and 4.68 (ABq, J = 14.3 Hz, 2H), 7.21-7.34 (m, 5H), 7.46 (dd, J = 4.8, 8.0 Hz, 1H), 7.88 (s, 2H), 7.97 (s, 1H), 8.07 (dt, J = 8.0, 1.9 Hz, 1H), 8.65-8.70 (m, 2H), 8.89 (d, J = 1.9 Hz, 1H). |

TABLE 2

| Compound No. | ¹H NMR spectrum |
| --- | --- |
| Compound 9 | 3.30-3.36 (m, 1H), 3.48-3.55 (m, 1H), 3.60-3.66 (m, 1H), 3.73 (dd, J = 7.1, 9.5 Hz, 1H), 3.76 (dd, J = 5.7, 9.5 Hz, 1H), 4.63 and 4.66 (ABq, J = 13.4 Hz, 2H), 7.10 (t, J = 8.8 Hz, 2H), 7.33 (dd, J = 5.7, 8.8 Hz, 2H), 7.45 (dd, J = 4.3, 8.1 Hz, 1H), 7.83 (s, 2H), 7.96 (s, 1H), 8.05 (dt, J = 8.1, 2.0 Hz, 1H), 8.63-8.69 (m, 2H), 8.86 (d, J = 2.0 Hz, 1H). |
| Compound 10 | 3.36-3.42 (m, 1H), 3.55-3.62 (m, 1H), 3.66-3.72 (m, 2H), 3.75 (dd, J = 6.0, 9.6 Hz, 1H), 4.63 and 4.65 (ABq, J = 13.8 Hz, 2H), 7.09 (t, J = 8.8 Hz, 2H), 7.33 (dd, J = 5.7, 8.8 Hz, 2H), 7.52-7.57 (m, 1H), 7.84 (s, 2H), 7.91-8.00 (m, 3H), 8.52 (d, J = 4.6 Hz, 1H), 8.73 (t, J = 6.0 Hz, 1H). |
| Compound 11 | 3.29-3.32 (m, 1H), 3.51-3.55 (m, 1H), 3.64-3.68 (m, 1H), 3.74-3.78 (m, 2H), 4.66 (s, 2H), 7.23-7.30 (m, 5H), 7.65 (d, J = 5.8 Hz, 1H), 7.71 (s, 1H), 7.87 (s, 2H), 7.97 (s, 1H), 8.51 (d, J = 5.8 Hz, 1H), 8.87 (t, J = 5.5 Hz, 1H). |
| Compound 12 | 3.29-3.32 (m, 1H), 3.45-3.48 (m, 1H), 3.55-3.58 (m, 1H), 3.68-3.76 (m, 2H), 4.65 and 4.6 (ABq, J = 13.5 Hz, 2H), 6.34 (d, J = 7.0 Hz, 1H), 6.57 (s, 1H), 7.09-7.13 (m, 2H), 7.30-7.33 (m, 2H), 7.40 (d, J = 7.0 Hz, 1H), 7.84 (s, 2H), 7.98 (s, 1H), 8.58 (t, J = 5.7 Hz, 1H), 11.76 (brs, 1H). |
| Compound 13 | 2.30 (s, 3H), 2.29-2.31 (m, 1H), 3.57-3.61 (m, 2H), 3.74-3.78 (m, 2H), 4.67 (s, 2H), 7.19-7.32 (m, 6H), 7.49 (d, J = 7.4 Hz, 1H), 7.90 (s, 2H), 7.99 (s, 1H), 8.40-8.44 (m, 2H). |
| Compound 14 | 2.45 (s, 3H), 3.26-3.29 (m, 1H), 3.48-3.51 (m, 1H), 3.60-3.63 (m, 1H), 3.74-3.81 (m, 2H), 4.66 (s, 2H), 7.22-7.32 (m, 6H), 7.57 (d, J = 7.7 Hz, 1H), 7.89 (s, 2H), 7.99 (s, 1H), 8.54 (t, J = 5.7 Hz, 1H). |
| Compound 15 | 3.26-3.33 (m, 1H), 3.50-3.53 (m, 1H), 3.62-3.66 (m, 1H), 3.73-3.79 (m, 2H), 4.67 (s, 2H), 7.24-7.32 (m, 5H), 7.61 (d, J = 8.0 Hz, 1H), 7.78 (d, J = 8.0 Hz, 1H), 7.89 (s, 2H), 7.99 (s, 1H), 8.66 (t, J = 5.8 Hz, 1H). |
| Compound16 | 3.26-3.28 (m, 1H), 3.51-3.53 (m, 1H), 3.65-3.68 (m, 1H), 3.76-3.80 (m, 2H), 4.67 (s, 2H), 7.23-7.33 (m, 5H), 7.90 (s, 2H), 7.99-8.03 (m, 2H), 8.69-8.71 (m, 1H). |
| Compound 17 | 3.27-3.29 (m, 1H), 3.51-3.54 (m, 1H), 3.73-3.81 (m, 6H), 3.88 (s, 3H), 4.68 (s, 2H), 6.46 (d, J = 8.3 Hz, 1H), 7.26-7.37 (m, 5H), 7.87-7.90 (m, 3H), 7.98 (s, 1H), 8.12 (d, J = 8.3 Hz, 1H). |

TABLE 3

| Compound No. | ¹H NMR spectrum |
| --- | --- |
| Compound 18 | 3.35-3.43 (m, 1H), 3.67-3.86 (m, 4H), 4.69-and 4.71 (ABq, J = 13.9 Hz, 2H), 7.27-7.40 (m, 6H), 7.48-7.53 (m, 1H), 7.70 (d, J = 8.3 Hz, 1H), 7.73-7.78 (m, 1H), 7.92 (s, 2H), 7.99 (s, 1H), 8.03 (d, J = 8.3 Hz, 1H), 8.75 (t, J = 5.6 Hz, 1H), 8.85 (d, J = 4.3 Hz, 1H). |
| Compound 19 | 3.35-3.41 (m, 1H), 3.64-3.83 (m, 4H), 4.69 and 4.71 (ABq, J = 13.9 Hz, 2H), 7.11-7.18 (m, 2H), 7.34 (d, J = 4.3 Hz, 1H), 7.37-7.41 (m, 2H), 7.48-7.52 (m, 1H), 7.70 (d, J = 8.3 Hz, 1H), 7.74-7.78 (m, 1H), 7.87 (s, 2H), 7.97 (s, 1H), 8.02 (d, J = 8.3 Hz, 1H), 8.74 (t, J = 5.7 Hz, 1H), 8.90 (d, J = 4.3 Hz, 1H). |
| Compound 20 | 3.30-3.33 (m, 1H), 3.51-3.54 (m, 1H), 3.63-3.66 (m, 1H), 3.74 (dd, J = 7.0, 9.5 Hz, 1H), 3.79 (dd, J = 5.9, 9.5 Hz, 1H), 4.65 and 4.66 (ABq, J = 13.5 Hz, 2H), 7.22-7.31 (m, 5H), 7.73 (d, J = 7.1 Hz, 2H), 7.87 (s, 2H), 7.98 (s, 1H), 8.27 (d, J = 7.1 Hz, 2H), 8.73 (t, J = 5.6 Hz, 1H). |
| Compound 21 | 3.30-3.36 (m, 1H), 3.47-3.55 (m, 1H), 3.61-3.68 (m, 1H), 3.73 (dd, J = 7.0, 9.5 Hz, 1H), 3.77 (dd, J = 5.7, 9.5 Hz, 1H), 4.64 and 4.68 (ABq, J = 13.5 Hz, 2H), 7.11 (t, J = 8.6 Hz, 2H), |

TABLE 3-continued

| Compound No. | ¹H NMR spectrum |
|---|---|
| | 7.33 (dd, J = 5.6, 8.6 Hz, 2H), 7.73 (d, J = 7.1 Hz, 2H), 7.84 (s, 2H), 7.98 (s, 1H), 8.27 (d, J = 7.1 Hz, 2H), 8.70 (t, J = 5.5 Hz, 1H). |
| Compound 22 | 3.29-3.34 (m, 1H), 3.49-3.55 (m, 1H), 3.62-3.68 (m, 1H), 3.74 (dd, J = 6.8, 9.5 Hz, 1H), 3.78 (dd, J = 5.9, 9.5 Hz, 1H), 4.65 and 4.67 (Abq, J = 13.7 Hz, 2H), 7.22-7.33 (m, 5H), 7.47 (dd, J = 6.5, 7.8 Hz, 1H), 7.60 (dt, J = 7.8, 1.2 Hz, 1H), 7.88 (s, 2H), 7.98 (s, 1H), 8.32 (dt, J = 6.5, 1.2 Hz, 1H), 8.45 (t, J = 1.2 Hz, 1H), 8.67 (t, J = 5.6 Hz, 1H). |
| Compound 23 | 3.30-3.37 (m, 1H), 3.49-3.55 (m, 1H), 3.62-3.67 (m, 1H), 3.74 (dd, J = 6.8, 9.5 Hz, 1H), 3.78 (dd, J = 5.9, 9.5 Hz, 1H), 4.65 and 4.67 (ABq, J = 13.7 Hz, 2H), 7.21-7.33 (m, 5H), 7.48 (dd, J = 6.5, 7.8 Hz, 1H), 7.61 (d, J = 7.8 Hz, 1H), 7.88 (s, 2H), 7.98 (s, 1H), 8.32 (dt, J = 6.5, 1.2 Hz, 1H), 8.45 (t, J = 1.2 Hz, 1H), 8.77 (t, J = 5.6 Hz, 1H). |
| Compound 24 | 3.27-3.34 (m, 1H), 3.63-3.70 (m, 1H), 3.73-3.86 (m, 2H), 4.69 (s, 2H), 7.22-7.36 (m, 5H), 7.54-7.62 (m, 2H), 7.92 (s, 2H), 7.98 (s, 1H), 8.20 (dd, J = 2.8, 7.3 Hz, 1H), 8.35 (dd, J = 1.5, 7.3 Hz, 1H), 11.26 (t, J = 5.5 Hz, 1H). |

TABLE 4

| Compound No. | ¹H NMR spectrum |
|---|---|
| Compound 25 | 3.28-3.36 (m, 1H), 3.59-3.67 (m, 1H), 3.70-3.85 (m, 3H), 4.65 and 4.67 (ABq, J = 13.8 Hz, 2H), 7.11 (t, J = 8.8 Hz, 2H), 7.36 (dd, J = 5.7, 8.8 Hz, 2H), 7.52-7.60 (m, 2H), 7.87 (s, 2H), 7.95 (s, 1H), 8.18-8.20 (m, 1H), 8.33-8.35 (m, 1H), 11.23 (t, J = 5.5 Hz, 1H). |
| Compound 26 | 3.20-3.40 (m, 1), 3.60-3.67 (m, 1H), 3.72-3.80 (m, 2H), 3.82 (dd, J = 6.1 9.6 Hz, 1H), 4.40 (s, 3H), 4.67 and 4.72 (Abq, J = 14.5 Hz, 2H), 7.21-7.30 (m, 5H), 7.90 (s, 2H), 7.99 (s, 1H), 8.30 (d, J = 6.6 Hz, 2H), 9.13 (d, J = 6.6 Hz, 2H), 9.62 (t, J = 5.6 Hz, 1H). |
| Compound 27 | 3.34-3.40 (m, 1H), 3.58-3.65 (m, 1H), 3.69-3.78 (m, 2H), 3.81 (dd, J = 6.0, 9.5 Hz, 1H), 4.38 (s, 3H), 4.67 and 4.69 (ABq, J = 13.5 Hz, 2H), 7.11 (t, J = 8.7 Hz, 2H), 7.35 (dd, J = 5.7, 8.7 Hz, 2H), 7.86 (s, 2H), 7.99 (s, 1H), 8.28 (d, J = 6.7 Hz, 2H), 9.11 (d, J = 6.7 Hz, 2H), 9.22 (t, J = 5.3 Hz, 1H). |
| Compound 28 | 3.30-3.38 (m, 1H), 3.60-3.67 (m, 1H), 3.72-3.80 (m, 2H), 3.82 (dd, J = 6.0, 9.5 Hz, 1H), 4.39 (s, 3H), 4.67 and 4.69 (ABq, J = 13.9 Hz, 2H), 7.22-7.36 (m, 5H), 7.88 (s, 2H), 7.99 (s, 1H), 8.21 (dd, J = 6.2, 8.0 Hz, 1H), 8.79 (d, J = 8.0 Hz, 1H), 9.08 (d, J = 6.2 Hz, 1H), 9.10 (t, J = 5.4 Hz, 1H), 9.33 (s, 1H). |
| Compound 29 | 3.30-3.38 (m, 1H), 3.58-3.66 (m, 1H), 3.70-3.87 (m, 2H), 3.80 (dd, J = 5.9, 9.5 Hz, 1H), 4.40 (s, 3H), 4.66 and 4.70 (ABq, J = 13.5 Hz), 7.09-7.15 (m, 2H), 7.33-7.38 (m, 2H), 7.84 (s, 2H), 7.97 (s, 1H), 8.23 (dd, J = 6.2, 8.0 Hz, 1H), 8.78 (d, J = 8.0 Hz, 1H), 9.09-9.12 (m, 2H), 9.31 (s, 1H). |
| Compound 30 | 3.30-3.41 (m, 1H), 3.60-3.65 (m, 1H), 3.68-3.83 (m, 3H), 4.67 (ABq, J = 13.5 Hz, 2H), 5.93 (s, 2H), 7.21-7.33 (m, 5H), 7.42-7.47 (m, 3H), 7.55-7.58 (m, 2H), 7.88 (s, 2H), 7.96 (s, 1H), 8.45 (d, J = 6.6 Hz, 2H), 9.40 (d, J = 6.6 Hz, 2H), 9.63 (t, J = 5.5 Hz, 1H). |
| Compound 31 | 3.40-3.45 (m, 1H), 3.57-3.65 (m, 1H), 3.66-3.72 (m, 1H), 3.75 (dd, J = 7.0, 9.6 Hz, 1H), 3.81 (dd, J = 5.7, 9.6 Hz, 1H), 4.68 (ABq, J = 14.3 Hz, 2H), 5.96 (s, 2H), 7.07-7.13 (m, 2H), 7.33-7.38 (m, 2H), 7.41-7.48 (m, 3H), 7.56-7.61 (m, 2H), 7.86 (s, 2H), 7.96 (s, 1H), 8.50 (d, J = 6.6 Hz, 2H), 9.44 (d, J = 6.6 Hz, 2H), 9.75 (t, J = 5.5 Hz, 1H). |

TABLE 5

| Compound No. | ¹H NMR spectrum |
|---|---|
| Compound 32 | 3.30-3.43 (m, 1H), 3.62-3.72 (m, 2H), 3.75-3.86 (m, 2H), 4.69 (ABq, J = 13.9 Hz, 2H), 5.93 (s, 2H), 7.21-7.34 (m, 5H), 7.43-7.47 (m, 3H), 7.60-7.63 (m, 2H), 7.88 (s, 2H), 7.97 (s, 1H), 8.25 (dd, J = 6.3, 8.0 Hz, 1H), 8.99 (d, J = 8.0 Hz, 1H), 9.33 (d, J = 6.3 Hz, 1H), 9.66 (t, J = 5.5 Hz, 1H), 9.81 (s, 1H). |
| Compound 33 | 3.12-3.18 (m, 1H), 3.36-3.39 (m, 1H), 3.40 (s, 2H), 3.44-3.52 (m, 1H), 3.68 (dd, J = 7.2, 9.7 Hz, 1H), 3.70 (dd, J = 6.1, 9.7 Hz, 1H), 4.61 and 4.64 (ABq, J = 13.4 Hz, 2H), 7.12 (d, J = 5.8 Hz, |

TABLE 5-continued

| Compound No. | $^1$H NMR spectrum |
|---|---|
| | 2H), 7.22-7.32 (m, 5H), 7.87 (s, 2H), 7.98 (s, 1H), 8.15 (t, J = 5.6 Hz, 1H), 8.41 (d, J = 5.8 Hz, 2H). |
| Compound 34 | 3.12-3.18 (m, 1H), 3.31-3.38 (m, 1H), 3.38 (s, 2H), 3.42-3.48 (m, 1H), 3.65 (dd, J = 7.1, 9.5 Hz, 1H), 3.68 (dd, J = 5.8, 9.5 Hz, 1H), 4.61 and 4.64 (ABq, J = 13.4 Hz, 2H), 7.08 (t, J = 8.6 Hz, 2H), 7.12 (d, J = 5.8 Hz, 2H), 7.52 (dd, J = 5.7, 8.6 Hz, 2H), 7.84 (s, 2H), 7.98 (s, 1H), 8.13 (t, J = 5.6 Hz, 1H), 8.42 (d, J = 5.8 Hz, 2H). |
| Compound 35 | 3.10-3.17 (m, 1H), 3.30-3.36 (m, 1H), 3.39 (s, 2H), 3.66 (dd, J = 7.1, 9.6 Hz, 1H), 3.70 (dd, J = 6.0, 9.6 Hz, 1H), 4.60 and 4.63 (ABq, J = 13.4 Hz, 2H), 7.20-7.31 (m, 6H), 7.51 (dt, J = 7.8, 1.8 Hz, 1H), 7.86 (s, 2H), 7.98 (s, 1H), 8.12 (t, J = 5.6 Hz, 1H), 8.39 (d, J = 1.8 Hz, 1H), 8.41 (dd, J = 1.5, 4.7 Hz, 1H). |
| Compound 36 | 3.12-3.18 (m, 1H), 3.30-3.37 (m, 1H), 3.38 (s, 2H), 3.42-3.49 (m, 1H), 3.64 (dd, J = 7.1, 9.4 Hz, 1H), 3.68 (dd, J = 5.8, 9.4, 1H), 4.60 and 4.64 (Abq, J = 13.4 Hz, 2H), 7.08 (t, J = 8.8 Hz, 2H), 7.22-7.29 (m, 3H), 7.50-7.53 (m, 1H), 7.84 (s, 2H), 7.99 (s, 1H), 8.15 (t, J = 5.6 Hz, 1H), 8.37 (s, 1H), 8.41 (d, J = 4.7 Hz, 1H). |
| Compound 37 | 3.11-3.18 (m, 1H), 3.30-3.38 (m, 1H), 3.44-3.51 (m, 1H), 3.55 (s, 2H), 3.68 (dd, J = 7.1, 9.5 Hz, 1H), 3.72 (dd, J = 5.8, 9.5 HZ, 1H), 4.62 and 4.64 (ABq, J = 13.4 Hz, 2H), 7.17-7.31 (m, 7H), 7.66 (dt, J = 7.6, 1.7 Hz, 1H), 7.86 (s, 2H), 7.98 (s, 1H), 8.10 (t, J = 5.6 Hz, 1H), 8.41 (d, J = 4.8 Hz, 1H). |

TABLE 6

| Compound No. | $^1$H NMR spectrum |
|---|---|
| Compound 38 | 3.12-3.19 (m, 1H), 3.29-3.36 (m, 1H), 3.43-3.49 (m, 1H), 3.55 (s, 2H), 3.65 (dd, J = 7.2, 9.5 Hz, 1H), 3.71 (dd, J = 5.6, 9.5 Hz, 1H), 4.61 and 4.64 (ABq, J = 13.4 Hz, 2H), 7.06-7.11 (m, 2H), 7.18-7.30 (m, 4H), 7.67 (dt, J = 1.8, 7.7 Hz, 1H), 7.83 (s, 2H), 7.99 (s, 1H), 8.13 (t, J = 5.7 Hz, 1H), 8.42 (dd, J = 1.8, 4.9 Hz, 1H). |
| Compound 39 | 3.10-3.17 (m, 1H), 3.33-3.39 (m, 1H), 3.38 (s, 2H), 3.43-3.50 (m, 1H), 3.67 (dd, J = 7.2, 9.5 Hz, 1H), 3.71 (dd, J = 6.1, 9.5 Hz, 1H), 4.61 and 4.64 (ABq, J = 13.4 Hz, 2H), 7.12 (d, J = 6.8 Hz, 2H), 7.21-7.31 (m, 4H), 7.87 (s, 2H), 7.99 (s, 1H), 8.08 (d, J = 6.8 Hz, 2H), 8.13 (t, J = 5.6 Hz, 1H). |
| Compound 40 | 3.10-3.17 (m, 1H), 3.30-3.38 (m, 1H), 3.36 (s, 2H), 3.42-3.49 (m, 1H), 3.64 (dd, J = 7.1, 9.5 Hz, 1H), 3.72 (dd, J = 5.8, 9.5 Hz, 1H), 4.61 and 4.64 (ABq, J = 13.4 Hz, 2H), 7.06-7.16 (m, 4H), 7.25 (dd, J = 5.6, 8.5 Hz, 1H), 7.83 (s, 2H), 7.98 (s, 1H), 8.08-8.12 (m, 2H), 8.42 (dd, = 1.0, 4.9 Hz, 1H). |
| Compound 41 | 3.11-3.17 (m, 1H), 3.31-3.39 (m, 1H), 3.36 (s, 2H), 3.45-3.52 (m, 1H), 3.65-3.73 (m, 2H), 4.62 and 4.64 (ABq, J = 13.4 Hz, 2H), 7.06 (d, J = 7.8 Hz, 1H), 7.20-7.32 (m, 6H), 7.87 (s, 2H), 7.99 (s, 1H), 8.06-8.11 (m, 2H), 8.17 (t, J = 5.6 Hz, 1H). |
| Compound 42 | 3.11-3.17 (m, 1H), 3.29-3.37 (m, 1H), 3.36 (s, 2H), 3.41-3.48 (m, 1H), 3.64 (dd, J = 7.2, 9.5 Hz, 1H), 3.69 (dd, J = 5.9, 9.5 Hz, 1H), 4.61 (ABq, J = 13.4 Hz, 2H), 7.04-7.11 (m, 3H), 7.23-7.31 (m, 3H), 7.84 (s, 2H), 7.99 (s, 1H), 8.06-8.10 (m, 2H), 8.15 (t, J = 5.7 Hz, 1H). |
| Compound 43 | 3.11-3.18 (m, 1H), 3.30-3.37 (m, 1H), 3.44-3.51 (m, 1H), 3.64 (s, 2H), 3.72 (dd, J = 7.1, 9.5 Hz, 1H), 3.75 (dd, J = 5.8, 9.5 Hz, 1H), 4.62 and 4.65 (ABq, J = 13.2 Hz, 2H), 7.10-7.38 (m, 8H), 7.88 (s, 2H), 7.97 (s, 1H), 8.23 (d, J = 6.3 Hz, 1H), 8.27 (t, J = 5.7 Hz, 1H). |
| Compound 44 | 3.12-3.19 (m, 1H), 3.29-3.36 (m, 1H), 3.43-3.49 (m, 1H), 3.64 (s, 2H), 3.68 (dd, J = 7.2, 9.5 Hz, 1H), 3.74 (dd, J = 5.7, 9.5 Hz, 1H), 4.63 and 4.65 (ABq, J = 13.4 Hz, 2H), 7.04-7.10 (m, 2H), 7.25-7.40 (m, 5H), 7.85 (s, 2H), 7.97 (s, 1H), 8.13 (d, J = 6.3 Hz, 1H), 8.17 (t, J = 5.7 Hz, 1H). |

TABLE 7

| Compound No. | $^1$H NMR spectrum |
| --- | --- |
| Compound 45 | 3.19-3.25 (m, 1H), 3.46-3.50 (m, 1H), 3.60-3.65 (m, 1H), 3.72 (dd, J = 6.9, 9.6 Hz, 1H), 3.75 (dd, J = 6.0, 9.6 Hz, 1H), 4.65 and 4.68 (ABq, J = 14.0 Hz, 2H), 6.80 (d, J = 15.9 Hz, 1H), 7.22-7.34 (m, 5H), 7.36 (d, J = 15.9 Hz, 1H), 7.47-7.49 (m, 2H), 7.88 (s, 2H), 7.97 (s, 1H), 8.25 (t, J = 5.7 Hz, 1H), 8.59 (dd, J = 1.4, 4.6 Hz, 2H). |
| Compound 46 | 3.21-3.28 (m, 1H), 3.47-3.53 (m, 1H), 3.61-3.68 (m, 1H), 3.72-3.80 (m, 2H), 4.67 and 4.69 (ABq, J = 14 Hz, 2H), 6.72 (d, J = 15.9 Hz, 1H), 7.22-7.36 (m, 5H), 7.42-7.48 (m, 2H), 7.89 (s, 2H), 7.94-8.00 (m, 2H), 8.23 (t, J = 5.5 Hz, 1H), 8.55 (d, J = 4.2 Hz, 1H), 8.74 (s, 1H). |
| Compound 47 | 3.12-3.28 (m, 1H), 3.43-3.50 (m, 1H), 3.58-3.65 (m, 1H), 3.70 (dd, J = 7.0, 9.5 Hz, 1H), 3.74 (dd, J = 5.8, 9.5 Hz, 1H), 4.66 and 4.68 (ABq, J = 13.5 Hz, 2H), 6.70 (d, J = 16 Hz, 1H), 7.10-7.16 (m, 2H), 7.34 (dd, J = 5.7, 8.6 Hz, 2H), 7.41-7.46 (m, 2H), 7.86 (s, 2H), 7.93-7.98 (m, 2H), 8.18 (t, J = 5.7 Hz, 1H), 8.55 (dd, J = 1.4, 4.6 Hz, 1H), 8.73 (d, J = 2 Hz, 1H). |
| Compound 48 | 2.37 (t, J = 7.5 Hz, 2H), 2.78 (t, J = 7.5 Hz, 2H), 3.06-3.13 (m, 1H), 3.26-3.34 (m, 1H), 3.60-3.68 (m, 2H), 4.60 and 4.63 (ABq, J = 13.4 Hz, 2H), 7.16 (d, J = 5.4 Hz, 2H), 7.20-7.32 (m, 5H), 7.87 (s, 2H), 7.89 (t, J = 5.6 Hz, 1H), 7.97 (s, 1H), 8.42 (d, J = 5.4 Hz, 2H). |
| Compound 49 | 2.35 (t, J = 7.5 Hz, 2H), 2.75 (t, J = 7.5 Hz, 2H), 3.03-3.10 (m, 1H), 3.23-3.30 (m, 1H), 3.40-3.46 (m, 1H), 3.59-3.66 (m, 2H), 4.59 and 4.62 (ABq, J = 13.3 Hz, 2H), 7.18-7.21 (m, 6H), 7.55 (d, J = 7.8 Hz, 1H), 7.84-7.89 (m, 3H), 7.98 (s, 1H), 8.36-8.41 (m, 2H). |
| Compound 50 | 2.36 (t, J = 7.5 Hz, 2H), 2.78 (t, J = 7.5 Hz, 2H), 3.04-3.10 (m, 1H), 3.22-3.29 (m, 1H), 3.38-3.46 (m, 1H), 3.60 (dd, J = 7.2, 9.4 Hz, 1H), 3.63 (dd, J = 5.6, 9.4 Hz, 1H), 4.59 and 4.63 (ABq, J = 13.3 Hz, 2H), 7.05-7.11 (m, 2H), 7.20-7.30 (m, 3H), 7.53-7.57 (m, 1H), 7.83 (s, 2H), 7.86 (t, J = 5.6 Hz, 1H), 7.97 (s, 1H), 8.36-8.42 (m, 2H). |
| Compound 51 | 2.34 (t, J = 7.3 Hz, 2H), 2.75 (t, J = 7.3 Hz, 2H), 3.04-3.12 (m, 1H), 3.24-3.32 (m, 1H), 3.40-3.46 (m, 1H), 3.62 (d, J = 6.4 Hz, 2H), 4.59 and 4.63 (ABq, J = 13.3 Hz, 2H), 7.17 (d, J = 6.9 Hz, 2H), 7.19-7.31 (m, 5H), 7.86 (s, 2H), 7.87 (t, J = 5.6 Hz, 1H), 7.98 (s, 1H), 8.08 (d, J = 6.9 Hz, 2H). |

TABLE 8

| Compound No. | $^1$H NMR spectrum |
| --- | --- |
| Compound 59 | 1.05 (t, J = 7.0 Hz, 6H), 3.32-3.39 (m, 1H), 3.42-3.56 (m, 5H), 3.60-3.69 (m, 1H), 4.75 (dd, J = 7.2, 9.5 Hz, 1H), 4.78 (dd, J = 5.6, 9.5 Hz, 1H), 4.64 and 4.67 (ABq, J = 13.6 Hz, 2H), 5.00-5.60 (brs, 2H), 7.20-7.34 (m, 5H), 7.66-7.96 (brs, 2H), 7.88 (s, 2H), 7.97 (s, 1H), 8.30-8.70 (brs, 1H), 12.50-13.50 (brs, 1H). |
| Compound 60 | 3.28-3.40 (m, 1H), 3.49-3.59 (m, 1H), 3.61-3.70 (m, 1H), 3.72-3.84 (m, 2H), 4.66 (ABq, J = 13.4 Hz, 2H), 7.20-7.35 (m, 5H), 7.82 (d, J = 8.4 Hz, 2H), 7.87 (s, 2H), 7.96 (d, J = 8.4 Hz, 2H), 7.97 (s, 1H), 8.65 (t, J = 5.6 Hz, 1H), 13.17 (brs, 1H). |
| Compound 61 | 3.27-3.34 (m, 1H), 3.43-3.51 (m, 1H), 3.55-3.64 (m, 1H), 3.68-3.80 (m, 2H), 4.64 and 4.66 (ABq, J = 13.4 Hz, 2H), 6.76-6.89 (m, 2H), 7.17-7.32 (m, 5H), 7.58-7.66 (m, 2H), 7.87 (s, 2H), 7.98 (s, 1H), 8.24 (brs, 1H). |
| Compound 62 | 3.30-3.35 (m, 1H), 3.46-3.52 (m, 1H), 3.56-3.62 (m, 1H), 3.70 (dd, J = 7.3, 9.5 Hz, 1H), 3.75 (dd, J = 5.5, 9.5 Hz, 1H), 4.64 and 4.66 (ABq, J = 13.5 Hz, 2H), 6.80-7.00 (m, 2H), 7.05-7.12 (m, 2H), 7.29-7.34 (m, 2H), 7.65-7.80 (m, 2H), 7.84 (s, 2H), 7.98 (s, 1H), 8.28 (brs, 1H). |
| Compound 63 | 3.31-3.40 (m, 1H), 3.50-3.57 (m, 1H), 3.60-3.68 (m, 1H), 3.72-3.80 (m, 2H), 4.01-4.09 (m, 2H), 4.65 and 4.67 (ABq, J = 13.6 Hz, 2H), 7.18-7.30 (m, 5H), 7.53 (d, J = 8.1 Hz, 2H), 7.78 (d, J = 8.1 Hz, 2H), 7.88 (s, 2H), 7.98 (s, 1H), 8.56 (t, J = 5.3 Hz, 1H). |
| Compound 64 | 1.80-2.06 (m, 4H), 2.96-3.09 (m, 2H), 3.30-3.41 (m, 3H), 3.50-3.59 (m, 1H), 3.61-3.69 (m, 1H), 3.71-3.81 (m, 2H), 4.36 (d, J = 5.3 Hz, 2H), 4.66 (ABq, J = 13.3 Hz, 2H), 7.18-7.30 (m, 5H), 7.67 (d, J = 7.4 Hz, 2H), 7.80 (d, J = 7.4 Hz, 2H), 7.88 (s, 2H), 7.98 (s, 1H), 8.60 (t, J = 5.3 Hz, 1H), 11.12 (brs, 1H). |

TABLE 8-continued

| Compound No. | $^1$H NMR spectrum |
| --- | --- |
| Compound 65 | 1.29-1.40 (m, 1H), 1.62-1.86 (m, 5H), 2.76-2.88 (m, 2H), 3.20-3.28 (m, 2H), 3.31-3.40 (m, 1H), 3.50-3.59 (m, 1H), 3.61-3.68 (m, 1H), 3.70-3.80 (m, 2H), 4.27 (d, J = 5.2 Hz, 2H), 4.66 (ABq, J = 13.5 Hz, 2H), 7.19-7.31 (m, 5H), 7.67 (d, J = 8.1 Hz, 2H), 7.81 (d, J = 8.1 Hz, 2H), 7.88 (s, 2H), 7.98 (s, 1H), 8.61 (t, J = 5.5 Hz, 1H), 10.77 (brs, 1H). |

TABLE 9

| Compound No. | $^1$H NMR spectrum |
| --- | --- |
| Compound 66 | 3.31-3.39 (m, 1H), 3.51-3.58 (m, 1H), 3.62-3.70 (m, 1H), 3.71-3.81 (m, 2H), 3.87 (s, 3H), 4.66 (s, 2H), 7.19-7.33 (m, 5H), 7.81-7.89 (m, 4H), 7.92-8.00 (m, 3H), 8.69 (t, J = 5.4 Hz, 1H). |
| Compound 67 | 1.48 (s, 9H), 3.26-3.35 (m, 1H), 3.43-3.52 (m, 1H), 3.56-3.63 (m, 1H), 3.70-3.80 (m, 2H), 4.64 (ABq, J = 13.5 Hz, 2H), 7.19-7.32 (m, 5H), 7.46 (d, J = 8.6 Hz, 2H), 7.66 (d, J = 8.6 Hz, 2H), 7.86 (s, 2H), 7.97 (s, 1H), 8.31 (t, J = 5.6 Hz, 1H), 9.57 (s, 1H). |
| Compound 68 | 1.48 (s, 9H), 3.26-3.35 (m, 1H), 3.42-3.53 (m, 1H), 3.55-3.63 (m, 1H), 3.66-3.78 (m, 2H), 4.64 and 4.66 (ABq, J = 13.5 Hz, 2H), 7.03-7.13 (m, 2H), 7.30-7.34 (m, 2H), 7.47 (d, J = 8.6 Hz, 2H), 7.65 (d, J = 8.6 Hz, 2H), 7.83 (s, 2H), 7.97 (s, 1H), 8.31 (t, J = 5.6 Hz, 1H), 9.58 (s, 1H). |
| Compound 69 | 1.39 (s, 9H), 3.25-3.38 (m, 1H), 3.45-3.54 (m, 1H), 3.58-3.67 (m, 1H), 3.70-3.80 (m, 2H), 4.14 (d, J = 6.0 Hz, 2H), 4.65 (ABq, J = 13.5 Hz, 2H), 7.18-7.22 (m, 7H), 7.42 (t, J = 6.0 Hz, 1H), 7.68 (d, J = 7.8 Hz, 2H), 7.87 (s, 2H), 7.97 (s, 1H), 8.42 (t, J = 5.7 Hz, 1H). |
| Compound 70 | 3.27-3.36 (m, 1H), 3.44-3.56 (m, 1H), 3.60-3.67 (m, 1H), 3.70-3.80 (m, 2H), 4.65 (ABq, J = 13.5 Hz, 2H), 4.78 (s, 2H), 7.19-7.31 (m, 5H), 7.47 (d, J = 8.1 Hz, 2H), 7.73 (d, J = 8.1 Hz, 2H), 7.87 (s, 2H), 7.97 (s, 1H), 8.50 (t, J = 5.4 Hz, 1H). |
| Compound 71 | (CDCl$_3$)1.44 (s, 9H), 1.46-1.56 (m, 2H), 1.60-1.68 (m, 2H), 2.02-2.09 (m, 1H), 2.58-2.72 (m, 2H), 3.16-3.23 (m, 1H), 3.46-3.54 (m, 1H), 3.71-3.80 (m, 3H), 3.96-4.11 (m, 2H), 4.60 (ABq, J = 13.5 Hz, 2H), 5.56 (t, J = 5.3 Hz, 1H), 7.17-7.38 (m, 5H), 7.70 (s, 2H), 7.79 (s, 1H). |
| Compound 72 | (CDCl$_3$)1.44 (s, 9H), 1.44-1.54 (m, 2H), 1.60-1.66 (m, 2H), 2.00-2.11 (m, 1H), 2.63-2.68 (m, 2H), 3.17-3.21 (m, 1H), 3.46-3.56 (m, 1H), 3.70-3.76 (m, 3H), 3.95-4.15 (m, 2H), 4.60 (ABq, J = 13.5 Hz, 2H), 5.62 (t, J = 5.4 Hz, 1H), 7.01-7.05 (m, 2H), 7.16-7.21 (m, 2H), 7.70 (s, 2H), 7.80 (s, 1H). |

TABLE 10

| Compound No. | $^1$H NMR spectrum |
| --- | --- |
| Compound 73 | 1.36 (s, 9H), 2.16 (t, J = 7.2 Hz, 2H), 3.00-3.16 (m, 3H), 3.23-3.31 (m, 1H), 3.38-3.48 (m, 1H), 3.63-3.73 (m, 2H), 4.63 and 4.64 (ABq, J = 13.5 Hz, 2H), 6.65 (brs, 1H), 7.18-7.31 (m, 5H), 7.86 (s, 3H), 7.98 (s, 1H). |
| Compound 74 | 2.41 (t, J = 7.1 Hz, 2H), 2.91-2.94 (m, 2H), 3.13-3.16 (m, 1H), 3.32-3.36 (m, 1H), 3.45-3.49 (m, 1H), 3.67-3.74 (m, 2H), 4.64 and 4.66 (ABq, J = 13.4 Hz, 2H), 7.22-7.32 (m, 5H), 7.82 (brs, 3H), 7.86 (s, 2H), 7.99 (s, 1H), 8.15 (t, J = 5.5 Hz, 1H). |
| Compound 75 | (CDCl$_3$) 1.42 (s, 9H), 2.25-2.33 (m, 2H), 3.13-3.33 (m, 1H), 3.32-3.38 (m, 2H), 3.47-3.56 (m, 1H), 3.68-3.80 (m, 3H), 4.60 (s, 2H), 5.03 (brs, 1H), 5.71 (brs, 1H), 7.00-7.07 (m, 2H), 7.15-7.22 (m, 2H), 7.69 (s, 2H), 7.79 (s, 1H). |
| Compound 76 | 2.42-2.45 (m, 2H), 2.85-2.95 (m, 2H), 3.14-3.18 (m, 1H), 3.30-3.35 (m, 1H), 3.43-3.47 (m, 1H), 3.66 (dd, J = 7.3, 9.6 Hz, 1H), 3.72 (dd, J = 5.6, 9.6 Hz, 1H), 4.64 and 4.66 (ABq, J = 13.4 Hz, 2H), 7.09-7.13 (m, 2H), 7.28-7.31 (m, 2H), 7.84 (s, 2H), 7.98 (brs, 4H), 8.21 (t, J = 5.7 Hz, 1H). |
| Compound 77 | 1.22-1.30 (m, 2H), 1.31-1.44 (m, 2H), 1.36 (s, 9H), 1.98 (t, J = 7.0 Hz, 2H), 2.80-2.90 (m, 2H), 3.10-3.18 (m, 1H), 3.23-3.34 8m, 1H), 3.39-3.49 (m, 1H), 3.66-3.75 (m, 2H), 4.63 and |

TABLE 10-continued

| Compound No. | ¹H NMR spectrum |
| --- | --- |
| | 4.64 (ABq, J = 14.0 Hz, 2H), 6.72 (t, J = 5.0 Hz, 1H), 7.20-7.32 (m, 5H), 7.77 (t, J = 5.4 Hz, 1H), 7.86 (s, 2H), 7.98 (s, 1H). |
| Compound 78 | 1.45-1.53 (m, 4H), 2.00-2.10 (m, 2H), 2.62-2.80 (m, 2H), 3.11-3.15 (m, 1H), 3.29-3.33 (m, 1H), 3.41-3.45 (m, 1H), 3.66-3.77 (m, 2H), 4.61-4.68 (m, 2H), 7.21-7.31 (m, 5H), 7.87 (s, 2H), 7.88-7.95 (m, 4H), 7.98 (s, 1H). |
| Compound 79 | (CDCl3) 1.45 (s, 9H), 1.60-1.74 (m, 4H), 1.93-2.02 (m, 1H), 2.09-2.18 (m, 1H), 2.87-2.92 (m, 2H), 3.07 (s, 2H), 3.16-3.24 (m, 1H), 3.46-3.55 (m, 2H), 3.70-3.80 (m, 3H), 4.59 and 4.60 (ABq, J = 14.0 Hz, 2H), 5.58 (t, J = 5.5 Hz, 1H), 7.19-7.38 (m, 5H), 7.70 (s, 2H), 7.78 (s, 1H). |
| Compound 80 | 1.78-1.84 (m, 4H), 2.22-2.34 (m, 1H), 2.95-3.17 (m, 3H), 3.30-3.46 (m, 4H), 4.08 (s, 2H), 4.64 and 4.65 (ABq, J = 13.4 Hz, 2H), 7.21-7.31 (m, 5H), 7.88 (s, 2H), 7.98 (s, 1H), 8.07 (t, J = 4.8 Hz, 1H), 10.10 (brs, 1H). |

TABLE 11

| Compound No. | ¹H NMR spectrum |
| --- | --- |
| Compound 81 | (CDCl3) 1.23 (t, J = 7.0 Hz, 3H), 3.17-3.22 (m, 1H), 3.23 (s, 2H), 3.57-3.65 (m, 1H), 3.69-3.79 (m, 3H), 4.10 (q, J = 7.0 Hz, 2H), 4.61 and 4.62 (ABq, J = 13.0 Hz, 2H), 7.16-7.36 (m, 5H), 7.72 (s, 2H), 7.78 (s, 1H). |
| Compound 82 | 3.09 (s, 2H), 3.11-3.14 (m, 1H), 3.28-3.32 (m, 1H), 3.46-3.50 (m, 1H), 3.69-3.74 (m, 2H), 4.64.63 and 4.64 (ABq, J = 13.5 Hz, 2H), 7.21-7.31 (m, 5H), 7.87 (s, 2H), 7.98 (s, 1H), 8.08 (t, J = 5.7 Hz, 1H), 12.46 (brs, 1H). |
| Compound 83 | 3.32-3.44 (m, 1H), 3.56-3.67 (m, 1H), 3.68-3.80 (m, 3H), 4.66 (s, 2H), 7.26-7.32 (m, 5H), 7.88 (s, 2H), 7.97 (s, 1H), 8.63 (dd, J = 1.4, 2.4 Hz, 1H), 8.83 (d, J = 2.4 Hz, 1H), 8.86 (t, J = 5.8 Hz, 1H), 9.13 (d, J = 1.4 Hz, 1H). |
| Compound 84 | (CDCl₃) 3.21-3.31 (m, 1H), 3.52-3.60 (m, 1H), 3.72-3.81 (m, 3H), 4.62 (s, 2H), 5.15 (t, J = 4.0 Hz, 1H), 7.01-7.40 (m, 10H), 7.71 (s, 2H), 7.78 (s, 1H). |
| Compound 85 | (CDCl₃) 1.10-1.21 (m, 2H), 1.44 (s, 9H), 1.78-1.88 (m, 2H), 2.71-2.85 (m, 2H), 3.13-3.20 (m, 1H), 3.35-3.44 (m, 1H), 3.60-3.78 (m, 4H), 4.05-4.12 (m, 1H), 4.28-4.33 (m, 1H), 4.60 (s, 2H), 7.12-7.38 (m, 7H), 7.69 (s, 2H), 7.78 (s, 1H). |
| Compound 86 | 1.48-1.53 (m, 2H), 1.82-1.86 (m, 2H), 2.90-2.94 (m, 2H), 3.06-3.09 (m, 1H), 3.15-3.26 (m, 3H), 3.43-3.47 (m, 1H), 3.61-3.70 (m, 3H), 4.64 and 4.66 (ABq, J = 13.5 Hz, 2H), 5.77 (brs, 1H), 6.26 (brs, 1H), 7.22-7.32 (m, 5H), 7.88 (s, 2H), 7.99 (s, 1H), 8.88 (brs, 2H). |
| Compound 87 | (CDCl₃) 1.44 (s, 9H), 1.45-1.66 (m, 8H), 1.97-2.06 (m, 1H), 3.16-3.26 (m, 1H), 3.47-3.58 (m, 1H), 3.62-3.71 (m, 1H), 3.72-3.81 (m, 3H), 4.56-4.68 (m, 3H), 5.58 (t, J = 4.0 Hz, 1H), 7.19-7.40 (m, 5H), 7.70 (s, 2H), 7.79 (s, 1H). |
| Compound 88 | 1.41-1.44 (m, 2H), 1.60-1.74 (m, 6H), 2.17-2.21 (m, 1H), 3.05-3.17 (m, 2H), 3.67-3.73 (m, 2H), 4.64 and 4.65 (ABq, J = 13.5 Hz, 2H), 7.21-7.31 (m, 5H), 7.83 (t, J = 5.6 Hz, 1H), 7.87 (s, 2H), 7.97-7.99 (m, 4H). |
| Compound 89 | (CDCl₃) 1.26 (t, J = 7.0 Hz, 3H), 1.36-1.56 (m, 2H), 1.66-1.75 (m, 2H), 1.98-2.09 (m, 2H), 2.14-2.20 (m, 1H), 2.44-2.60 (m, 2H), 2.87 (s, 2H), 3.18-3.28 (m, 2H), 3.47-3.60 (m, 2H), 3.70-3.76 (m, 2H), 3.80-3.88 (m, 1H), 4.13 (q, J = 7.0 Hz, 2H), 4.60 (s, 2H), 7.14-7.37 (m, 6H), 7.70 (s, 2H), 7.78 (s, 1H). |

TABLE 12

| Compound No. | ¹H NMR spectrum |
| --- | --- |
| Compound 90 | 1.40-1.44 (m, 2H), 1.60-1.63 (m, 2H), 1.90-1.93 (m, 2H), 2.07-2.09 (m, 2H), 2.43-2.50 (m, 1H), 2.75 (s, 2H), 3.23-3.25 (m, 1H), 3.33-3.35 (m, 3H), 3.66-3.69 (m, 2H), 4.65 (s, 2H), 7.21-7.31 (m, 5H), 7.54 (t, J = 5.9 Hz, 1H), 7.89 (s, 2H), 7.99 (s, 1H), 12.05 (brs, 1H). |
| Compound 91 | 1.41-1.44 (m, 1H), 1.65-2.26 (m, 8H), 2.71-2.74 (m, 1H), 2.88-3.77 (m, 16H), 4.65-4.68 (m, 2H), 7.24-7.72 (m, 5H), |

TABLE 12-continued

| Compound No. | $^1$H NMR spectrum |
|---|---|
| | 7.88 (s, 2H), 8.00 (s, 1H), 8.65 (brs, 1H), 10.15 (brs, 1H), 11.02 (brs, 1H). |
| Compound 92 | 1.10-1.58 (m, 13H), 2.05-2.48 (m, 1H), 2.58-2.92 (m, 5H), 3.12-3.54 (m, 2H), 3.60-3.94 (m, 4H), 4.05-4.11 (m, 1H), 4.60-4.71 (m, 2H), 7.15-7.37 (m, 6H), 7.87-8.07 (m, 3H). |
| Compound 93 | 1.52-1.69 (m, 4H), 2.52-2.59 (m, 1H), 2.78-2.91 (m, 6H), 3.15-3.22 (m, 2H), 3.52-3.79 (m, 4H), 4.64-4.71 (m, 2H), 7.22-7.37 (m, 5H), 7.88-7.90 (m, 2H), 7.99-8.01 (m, 1H), 8.46-8.65 (m, 1H), 8.85-9.10 (m, 1H). |
| Compound 94 | (CDCl$_3$) 1.45 (s, 9H), 1.46-1.70 (m, 4H), 2.44-2.53 (m, 1H), 2.58-2.75 (m, 2H), 2.84 and 2.86 (s x 2, 3H), 3.32-3.41 (m, 2H), 3.46-3.58 (m, 1H), 3.62-3.90 (m, 3H), 4.00-4.24 (m, 2H), 4.57 and 4.64 (s x 2, 2H), 6.96-7.08 (m, 2H), 7.14-7.28 (m, 2H), 7.65-7.82 (m, 3H). |
| Compound 95 | 1.50-1.65 (m, 4H), 2.55-2.86 (m, 6H), 3.13-3.20 (m, 2H), 3.56-3.75 (m, 5H), 4.61-4.70 (m, 2H), 7.07-7.16 (m, 2H), 7.29-7.32 (m, 2H), 7.40-7.43 (m, 2H), 7.86 (s, 2H), 7.99 (s, 1H), 8.57-8.63 (m, 1H), 9.03-9.20 (m, 1H). |
| Compound 96 | 1.35-1.49 (m, 5H), 1.81-1.84 (m, 1H), 2.02-2.35 (m, 4H), 2.56-2.82 (m, 5H), 3.23-3.42 (m, 2H), 3.59-3.79 (m, 3H), 4.63-4.70 (m, 2H), 7.20-7.32 (m, 5H), 7.89-8.02 (m, 3H). |
| Compound 97 | 1.53-1.82 (m, 4H), 2.55-2.90 (m, 6H), 3.32-3.38 (m, 3H), 3.57-3.75 (m, 7H), 4.62-4.71 (m, 2H), 7.08-7.17 (m, 2H), 7.29-7.43 (m, 2H), 7.85 (s, 2H), 7.99 (s, 1H), 10.38 (brs, 1H). |
| Compound 98 | 2.68 and 2.92 (s x 2, 3H), 3.52-3.59 (m, 3H), 3.76-3.79 (m, 2H), 4.56-4.69 (m, 2H), 7.01-7.17 (m, 5H), 7.40-7.43 (m, 1H), 7.77 and 7.89 (s x 2, 2H), 7.98 and 8.00 (s x 2, 1H), 8.50-8.60 (m, 2H). |

TABLE 13

| Compound No. | $^1$H NMR spectrum |
|---|---|
| Compound 99 | 2.76-2.93 (m, 3H), 3.31-3.36 (m, 1H), 3.39-3.87 (m, 4H), 4.62-4.69 (m, 2H), 7.00-7.44 (m, 7H), 7.85-7.99 (m, 2H), 8.08-8.46 (m, 3H). |
| Compound 100 | 2.71 and 2.87 (s x 2, 3H), 3.49-3.77 (m, 5H), 4.61-4.69 (m, 2H), 5.74-5.91 (m, 2H), 7.08-7.31 (m, 3H), 7.38-7.40 (m, 2H), 7.81 and 7.88 (s x 2, 2H), 7.98 and 7.99 (s x 2, 1H), 11.67 (brs, 1H). |
| Compound 101 | (CDCl$_3$) 1.41 and 1.43 (s x 2, 9H), 2.35-2.50 (m, 2H), 2.78 and 2.84, (s x 2, 3H), 3.15-3.90 (m, 7H), 4.53-4.64 (m, 2H), 5.18 (brs, 1H7.17-7.48 (m, 5H), 7.62-7.80 (m, 3H). |
| Compound 101 | 2.51-2.93 (m, 8H), 3.44-3.81 (m, 4H), 4.54-4.71 (m, 2H), 7.24-7.46 (m, 5H), 7.87-7.99 (m, 5H), 8.32-8.46 (m, 1H). |
| Compound 102 | (CDCl$_3$) 1.41 and 1.43 (s x 2, 9H), 2.35-2.50 (m, 2H), 2.78 and 2.84, s x 2, 3H), 3.15-3.90 (m, 7H), 4.53-4.64 (m, 2H), 5.18 (brs, 1H), 6.95-7.06 (m, 2H), 7.13-7.28 (m, 2H), 7.62-7.80 (m, 3H). |
| Compound 104 | 2.51-2.61 (m, 2H), 2.72-2.91 (m, 5H), 3.49-3.57 (m, 2H), 3.67-3.74 (m, 3H), 4.64-4.70 (m, 2H), 7.09-7.15 (m, 2H), 7.33-7.41 (m, 2H), 7.89-7.99 (m, 6H). |
| Compound 105 | 1.20-1.42 (m, 13H), 1.92-2.22 (m, 2H), 2.69 and 2.78 (s x 2, 3H), 2.80-2.91 (m, 2H), 3.17-3.56 (m, 3H), 3.65-3.80 (m, 2H), 4.05-4.10 (m, 1H), 4.59-4.70 (m, 2H), 6.62-6.76 (m, 1H), 7.17-7.48 (m, 5H), 7.86-8.04 (m, 3H). |
| Compound 106 | 1.40-1.51 (m, 4H), 2.00-2.23 (m, 2H), 2.66-2.87 (m, 5H), 3.32-3.49 (m, 2H), 3.67-3.77 (m, 3H), 4.64-4.70 (m, 2H), 7.23-7.32 (m, 5H), 7.87-8.01 (m, 6H). |
| Compound 107 | 1.64-1.91 (m, 4H), 2.69-3.01 (m, 11H), 3.16-3.57 (m, 5H), 3.88-3.98 (m, 1H), 4.26-4.66 (m, 2H), 7.08-7.20 (m, 4H), 7.26-7.35 (m, 4H), 4.46-4.52 (m, 2H), 7.90-8.02 (m, 3H), 9.74 (brs, 1H). |
| Compound 108 | (CDCl$_3$) 1.40-1.50 (m, 2H), 1.45 (s, 9H), 1.56-1.64 (m, 2H), 1.94-2.03 (m, 1H), 2.31 (s, 6H), 2.52-2.70 (m, 2H), 3.07-3.16 (m, 1H), 3.55-3.75 (m, 4H), 3.90-4.10 (m, 2H), 4.44 and 4.45 (ABq, J = 14.0 Hz, 2H), 6.03 (t, J = 4.5 Hz, 1H), 6.92 (s, 2H), 6.95 (s, 1H), 7.20-7.34 (m, 5H). |

TABLE 14

| Compound No. | $^1$H NMR spectrum |
| --- | --- |
| Compound 109 | 1.62-1.70 (m, 4H), 2.22 (s, 6H), 2.29-2.32 (m, 1H), 2.76-2.79 (m, 2H), 3.09-3.17 (m, 3H), 3.28-3.40 (m, 2H), 3.56-3.59 (m, 2H), 4.35 (s, 2H), 6.80 (s, 2H), 6.88 (s, 1H), 7.20-7.31 (m, 5H), 7.92 (t, J = 5.6 Hz, 1H), 8.73 (brs, 1H), 9.11 (brs, 1H). |
| Compound 110 | 1.46-1.48 (m, 4H), 1.77-1.94 (m, 3H), 2.12 (s, 3H), 2.22 (s, 6H), 2.69-2.71 (m, 2H), 3.07-3.09 (m, 1H), 3.25-3.39 (m, 2H), 3.55-3.59 (m, 2H), 4.32-4.37 (m, 2H), 6.80 (s, 2H), 6.87 (s, 1H), 7.21-7.30 (m, 5H). |
| Compound 111 | 1.36 (s, 9H), 2.11-2.20 (m, 2H), 2.21 (s, 6H), 3.00-3.11 (m, 3H), 3.21-3.30 (m, 1H), 3.39-3.47 (m, 1H), 3.54-3.63 (m, 2H), 4.35 (s, 2H), 6.65 (brs, 1H), 6.79 (s, 2H), 6.87 (s, 1H), 7.18-7.31 (m, 5H), 7.82 (t, J = 5.4 Hz, 1H). |
| Compound 112 | 2.22 (s, 6H), 2.42 (t, J = 7.1 Hz, 2H), 2.90 (t, J = 7.1 Hz, 2H), 3.08-3.12 (m, 1H), 3.30-3.34 (m, 1H), 3.43-3.47 (m, 1H), 3.56-3.61 (m, 2H), 4.36 (s, 2H), 6.79 (s, 2H), 6.87 (s, 1H), 7.21-7.32 (m, 5H), 7.91 (brs, 3H), 8.13 (t, J = 5.5 Hz, 1H). |
| Compound 113 | (CDCl$_3$) 1.40-1.52 (m, 11H), 1.55-1.64 (m, 2H), 2.00-2.08 (m, 1H), 2.54-2.70 (m, 2H), 3.07-3.14 (m, 1H), 3.52-3.70 (m, 4H), 3.93-4.12 (m, 2H), 4.47 (s, 2H), 5.85 (t, J = 4.0 Hz, 1H), 6.98-7.07 (m, 2H), 7.14-7.33 (m, 7H). |
| Compound 114 | 1.55-1.73 (m, 4H), 2.28-2.34 (m, 1H), 2.27-2.83 (m, 2H), 3.05-3.25 (m, 3H), 3.26-3.32 (m, 1H), 3.40-3.49 (m, 1H), 3.51-3.62 (m, 2H), 4.42 (s, 2H), 7.10-7.30 (m, 9H), 7.89 (t, J = 5.4 Hz, 1H), 8.68 (brs, 2H). |
| Compound 115 | 1.63-1.90 (m, 4H), 2.20-2.30 (m, 1H), 2.67 (s, 3H), 2.72-2.90 (m, 2H), 3.00-3.20 (m, 1H), 3.23-3.48 (m, 3H), 3.57-3.63 (m, 2H), 4.42 (s, 2H), 7.12-7.31 (m, 9H), 7.95 (m, 1H), 10.15 (brs, 1H). |
| Compound 116 | 3.25-3.35 (m, 1H), 3.50-3.56 (m, 1H), 3.60-3.75 (m, 3H), 4.44 (s, 2H), 7.05-7.35 (m, 9H), 7.61 (d, J = 6.0 Hz, 2H), 8.68 (d, J = 6.0 Hz, 2H), 8.71 (t, J = 5.5 Hz, 1H). |
| Compound 117 | 3.24-3.30 (m, 1H), 3.46-3.56 (m, 1H), 3.58-3.74 (m, 3H), 4.44 (s, 2H), 7.10-7.31 (m, 9H), 7.71 (d, J = 7 Hz, 2H), 8.27 (d, J = 7.0 Hz, 2H), 8.67 (t, J = 5.5 Hz, 1H). |

TABLE 15

| Compound No. | $^1$H NMR spectrum |
| --- | --- |
| Compound 118 | 1.36 (s, 9H), 2.11-2.18 (m, 2H), 2.99-3.11 (m, 3H), 3.20-3.29 (m, 1H), 3.38-3.46 (m, 1H), 3.52-3.61 (m, 1H), 4.41 (s, 2H), 6.66 (t, J = 4.5 Hz, 1H), 7.08-7.31 (m, 9H), 7.83 (t, J = 4.5 Hz, 1H). |
| Compound 119 | 2.41 (t, J = 7.1 Hz, 2H), 2.85-2.95 (m, 2H), 3.08-3.11 (m, 1H), 3.28-3.35 (m, 1H), 3.44-3.49 (m, 1H), 3.57-3.63 (m, 2H), 4.43 (s, 2H), 7.12-7.32 (m, 9H), 7.93 (brs, 3H), 8.15 (t, J = 5.5 Hz, 1H). |
| Compound 120 | 3.29-3.22 (m, 1H), 3.53-3.57 (m, 1H), 3.65-3.75 (m, 3H), 4.47 (s, 2H), 7.21-7.34 (m, 6H), 7.43 (s, 1H), 7.54 (d, J = 8.2 Hz, 1H), 7.76 (d, J = 6.7 Hz, 2H), 8.30 (d, J = 6.7 Hz, 2H), 8.73 (t, J = 5.4 Hz, 1H). |
| Compound 121 | 1.48 (s, 9H), 3.22-3.32 (m, 1H), 3.42-3.50 (m, 1H), 3.52-3.60 (m, 1H), 3.62-3.71 (m, 2H), 4.45 (s, 2H), 7.17-7.33 (m, 6H), 7.43 (s, 1H), 7.47 (d, J = 8.5 Hz, 2H), 7.53 (d, J = 8.2 Hz, 1H), 7.66 (d, J = 8.5 Hz, 2H), 8.28 (t, J = 5.4 Hz, 1H), 9.57 (s, 1H). |
| Compound 122 | 3.24-3.31 (m, 1H), 3.44-3.52 (m, 1H), 3.54-3.60 (m, 1H), 3.63-3.73 (m, 2H), 4.45 (s, 2H), 6.90 (brs, 2H), 7.18-7.35 (m, 6H), 7.43 (s, 1H), 7.55 (d, J = 8.2 Hz, 1H), 7.64 (d, J = 7.4 Hz, 2H), 8.24 (brs, 1H). |
| Compound 123 | 3.25-3.33 (m, 1H), 3.48-3.55 (m, 1H), 3.62-3.76 (m, 3H), 4.48 (s, 2H), 6.86-6.92 (m, 2H), 7.05-7.11 (m, 1H), 7.20-7.34 (m, 5), 7.73 (d, J = 7.1 Hz, 2H), 8.26 (d, J = 7.1 Hz, 2H), 8.69 (t, J = 5.5 Hz, 1H). |
| Compound 124 | 3.26-3.34 (m, 1H), 3.49-3.56 (m, 1H), 3.61-3.77 (m, 3H), 4.56 (s, 2H), 7.20-7.34 (m, 5H), 7.51-7.57 (m, 4H), 7.59-7.64 (m, 1H), 7.72 (d, J = 7.0 Hz, 2H), 8.26 (d, J = 7.0 Hz, 2H), 8.69 (t, J = 5.5 Hz, 1H). |
| Compound 125 | 3.30-3.33 (m, 1H), 3.51-3.54 (m, 1H), 3.63-3.66 (m, 1H), 3.74 (dd, J = 7.0, 9.5 Hz, 1H), 3.79 (dd, J = 5.9, 9.5 Hz, 1H), 4.65 and 4.66 (ABq, J = 13.5 Hz, 2H), 7.20-7.49 (m, 10H), 7.73 (d, J = 7.1 Hz, 2H), 8.27 (d, J = 7.1 Hz, 2H), 8.73 (t, J = 5.6 Hz, 1H). |

Example 138

Optical resolution of the Compound 21

An appropriate amount of the Compound 21 was spread on a chiral column manufactured by Daicel (Chiralpack AS) and eluted with a 1:1 mixed solvent of 2-propanol and n-hexane. As a result, the (+)-Compound 21 and the (−)-Compound 21 were produced.

Specific rotation of the (+)-compound 21 $[\alpha]_D^{20}=+26.1°$ cl, $CHCl_3$)

Specific rotation of the (−)-compound 21 $[\alpha]_D^{20}=-27.5°$ cl, $CHCl_3$)

Example 139

Human NK1 Receptor Binding Assay

A supernatant liquid was removed from an hNK1-CHO cell incubation flask in a confluent state, trypsin (0.25%)-EDTA (1 mmol/L) (Gibco) was added thereto and the cells were exfoliated and recovered. After they were washed with a buffer A (pH 7.5; 50 mmol/L Tris hydrochloride 50 mmol/L, 150 mmol/L NaCl and 0.02% BSA) for one time (at 1000 ppm for 5 minutes), cell numbers were adjusted and re-floated on a buffer for assay {a buffer A to which 40 µg/mL bacitracin (Sigma), 4 µg/mL leupeptin (Sigma), 4 µg/mL chymostatin (Sigma) and 4 µg/mL phosphoramidon (Sigma) were added}. The hNK1-CHO cells (100 µL) were placed in a tube (TPX-12, Maruemu) in which 300 µL of the buffer for assay was charged so as to make cells $10^5$ per tube, 50 µL of a hot solution ($^3H$-$Sar^9$-SP, final concentration: 0.3 mmol/L) and 50 µL of a substance to be tested were added (a system of 500 µL), stirred and made to react at room temperature for 60 minutes. After completion of the reaction, it was filtered through a GF/B filter (25 mm diameter, Whatman) which was previously dipped in 0.1% polyethyleneimine p-70 (Wako Pure Chemical), washed with the buffer A (4 mL each for three times), placed in a vial and dried at 60° C. for one night. After drying, 10 mL of a scintillator (AL-1, toluene base, Dojindo) was added thereto and dpm was measured by a liquid scintillation counter (for 5 minutes/vial).

With regard to a nonspecific binding, it was defined as the dpm when 10 µmol/L of the substance P was added instead of the substance to be tested. The experiment was conducted in duplicate and at least three experiments were repeated. $IC_{50}$ value was calculated using a probit method (statistic library II, Yukms).

An example of the result is shown in Table 16. The compound of the present invention showed a very strong antagonistic action in a human NK1 receptor binding assay.

TABLE 1 16

| Compound No. | $IC_{50}$ (nmol/L) |
| --- | --- |
| Compound 4 | 29.3 |
| Compound 20 | 5.8 |
| Compound 21 | 2.9 |
| (+)-Compound 21 | 9.0 |
| (−)-Compound 21 | 1.5 |
| Compound 22 | 6.4 |
| Compound 23 | 5.4 |
| Compound 26 | 5.9 |
| Compound 39 | 7.3 |
| Compound 40 | 7.3 |
| Compound 41 | 9.2 |
| Compound 42 | 4.0 |
| Compound 51 | 9.4 |
| Compound 54 | 8.5 |
| Compound 64 | 56.4 |
| Compound 74 | 33.6 |
| Compound 76 | 21.0 |
| Compound 78 | 19.0 |
| Compound 80 | 14.7 |
| Compound 86 | 6.0 |
| Compound 88 | 8.6 |
| Compound 90 | 44.0 |
| Compound 91 | 43.5 |
| Compound 93 | 42.2 |
| Compound 95 | 15.4 |
| Compound 96 | 28.5 |
| Compound 97 | 20.3 |
| Compound 98 | 27.0 |
| Compound 99 | 23.8 |
| Compound 100 | 11.9 |
| Compound 102 | 35.5 |
| Compound 104 | 6.5 |
| Compound 106 | 30.3 |

Example 140

Pharmacokinetic Test in Blood by a Single Administration to Guinea Pigs

Male guinea pigs of a Hartley strain (SPF, Nippon SLC) were purchased and subjected to a preliminary breeding for one week and the normally grown ones were fasted for one night and used for the test. The compound of the present invention was suspended in 1 g/dL methyl cellulose solution and 100 mg/kg was orally administered in an administering dose of 5 mL/kg. After 0.5, 1, 2, 4, 8 and 24 hour(s) from the oral administration, about 0.4 mL of blood was collected from the vein of median of foreleg using a heparinized capillary. Plasma prepared by its centrifugation (at 12,000 rpm for 10 minutes) was stored at −80° C. until the measurement. Measurement of the concentration in blood was conducted by a UV-detecting HPLC method.

An example of the result is shown in Table 17. When the pharmacokinetic property in blood after a single administration per os to guinea pigs was tested, the compound of the present invention showed a good transfer to the blood and a long half-life in the blood whereby a favorable pharmacokinetics were achieved.

TABLE 17

| | Pharmacokinetic parameter | | | |
| --- | --- | --- | --- | --- |
| Compound No. | Tmax (h) | Cmax (µg/mL) | AUC 0-24 h (µg/mL/mL) | t½ (h) |
| Compound 4 | 8 | 2 | 28.2 | N.C. |
| Compound 20 | 2 | 10.9 | 87.3 | 3.4 |
| Compound 21 | 4 | 26.9 | 314.9 | 3.2 |
| Compound 22 | 2 | 18.3 | 199.7 | 2.6 |
| Compound 23 | 4 | 17.5 | 235.7 | 3.5 |
| Compound 39 | 8 | 25.7 | 378.8 | 3.2 |
| Compound 40 | 4 | 22.8 | 278.7 | 4.0 |
| Compound 42 | 4 | 16.9 | 214.7 | 3.0 |
| Compound 51 | 1 | 13.8 | 102.6 | 3.4 |
| Compound 64 | 4 | 1.7 | 19.7 | 8.0 |

Example 141

Test for Transfer into Cerebral Center of Guinea Pigs

Male guinea pigs of a Hartley strain (four weeks age, SPF, Nippon SLC) were purchased, subjected to a preliminary breeding for not shorter than one week, fasted for one night and used for the test where one group comprised eight guinea pigs. As a substance to be tested, the Compound 21 which is the compound of the present invention was suspended in 1% methyl cellulose (CM) to make 20 mg/mL. As a substance for comparison, LY-303870 [(R)-1-[N-(2-methoxybenzyl)acetylamino]-3-(1H-indol-3-yl)-2-[N-(2-(4-(piperidin-1-yl)piperidin-1-yl)acetyl)amino]propane] was dissolved in a 1% aqueous solution of MC to make 20 mg/mL.

A test was conducted in accordance with a method of Iyengar, et al. Thus, a 1% aqueous solution of MC and the above-prepared solution of the test substance were orally administered in an administering dose of 5 mL/kg, then the animals were killed by carbon dioxide gas after 4 hours from administration of the test substance solution and after 1 hour from administration of the 1% aqueous MC solution and the comparative substance solution, the brain was excised and the striatum was collected. After measuring its wet weight, 50 mmol/L Tris-HCl (pH 7.5) was added thereto so as to make it 40 mg/mL followed by homogenizing for 10 seconds. After that, the homogenate was incubated at 37° C. for 15 minutes in order to remove the inherent substance P therefrom and stored at room temperature as a homogenate of guinea pig striatum.

Then, 450 μL of a binding buffer (50 mmol/L of Tris-HCl (pH 7.5), 3 mmol/L of $MnCl_2$, 0.2 mg/mL of BSA, 40 μg/mL of bacitracin, 2 μg/mL of chymostatin, 2.5 μg/mL of thiorphan and 4 μg/mL of leupeptin), 50 μL of 40 nmol/L [$^3$H] substance P and 50 μL of the striatum homogenate were added to a TPX-12 tube and incubated at room temperature for 1 hour. Further, in order to measure the nonspecific binding, 400 μL of a binding buffer, 50 μL of 40 nmol/L [$^3$H] substance P, 50 μL of 40 μmol/L unlabeled substance P and 500 μL of the striatum homogenate were added thereto and incubated at room temperature for 1 hour. After the incubation, the reaction was stopped by filtering through a GF/B filter (Whatman) dipped in 0.5% polyethyleneimine for not shorter than 2 hours and the filter was washed with a cold 50 mmol/L Tris-HCl (pH 7.5) twice. The filtrate was placed in a vial and dried at 56° C. for one night and 10 mL of a scintillator was added thereto followed by measuring using a liquid scintillation counter. All of the tests were conducted in duplicate.

An example of the result is shown in FIG. 1. For each of the control group (a group administered with 1% aqueous MS solution) and the group to which a test substance was administered, the value after deduction of each nonspecific binding (dpm) was defined as a specific binding (dpm). A test for the difference between mean values of the two groups was conducted by a t-test (SAS Pre-clinical Package, Ver. 5.0) and the case where p<0.05 was judged to be significant.

A suppressive action of the [$^3$H]substance P to NK1 receptor binding was investigated by oral administration of the compound of the present invention to guinea pigs using the striatum homogenate. The result was that, as shown in FIG. 1, the group to which the compound of the present invention was administered (228.2±15.5 dpm) showed a very low specific binding value (dpm) as compared with the control group (1083.4±95.5 dpm). Even when compared with a group to which a comparative substance LY 303870 being said to be a selective NK1 antagonist and to show excellent transfer to the center was administered, far low dpm value was achieved. When an occupying rate (%) of the NK1 receptor in the brain was calculated from the specific binding of the group to which the test substance was added against the control group and was expressed in terms of mean value ±standard deviation, that was 79.9±1.4% for the compound of the present invention and 33.1±3.5% for LY 303870. From the above result, it is apparent that the compound of the present invention shows a high transfer to the center and said compound is very useful as pharmaceuticals such as an antiemetic acting on central nerve systems.

INDUSTRIAL APPLICABILITY

As shown in Table 16, the benzyloxypropylamine derivatives in accordance with the present invention showed a strong antagonistic action to tachykinin receptors. Further, as will be apparent from Table 17, it showed a good transfer into the blood and a long half-life period in the blood in a pharmacokinetic test in the blood by oral administration to guinea pigs. Furthermore, as shown in FIG. 1, it showed a high transfer into the CNS under the oral administration condition in a predetermined dose to guinea pigs. As mentioned already, the benzyloxypropylamine derivative of the present invention is a strong antagonist to tachykinin receptors having a novel structure and shows a favorable pharmacokinetic property having an excellent transfer into the CNS as well as a good transfer into the blood, whereby it has a desirable characteristic as pharmaceuticals and its utility is very high.

The invention claimed is:

1. A benzyloxypropylamine derivative represented by the following formula (I) or a pharmaceutically acceptable salt thereof,

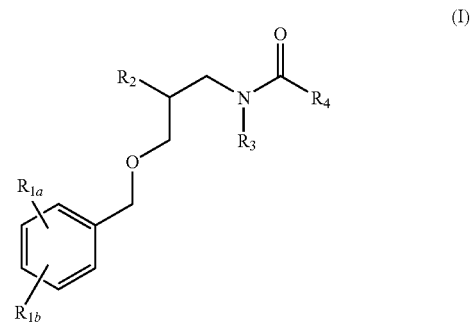

wherein in the formula, $R_{1a}$ and $R_{1b}$, which may be the same or different, is hydrogen, halogen, $C_{1-4}$ alkyl or trifluoromethyl; $R_2$ is phenyl which may be optionally substituted with halogen or diphenylmethyl; $R_3$ is hydrogen, $C_{1-4}$ alkyl or acetoxymethyl; and $R_4$ is a substituent selected from the following (a) to (j):

(a) piperidinyl which may be optionally substituted with $C_{1-4}$ alkyl, piperidinyl, carboxymethyl, tert-butoxycarbonyl, tert-butoxycarbonylmethyl or amino, (b) piperidinylamino which may be optionally substituted with tert-butoxycarbonyl, (c) piperidinylmethyl which may be optionally substituted with carboxy or tert-butoxycarbonyl, (d) pyridyl which may be optionally substituted with one or two group(s) selected from $C_{1-4}$ alkyl, $C_{1-4}$ alkoxy, halogen, hydroxy, oxy, amino, carboxy and benzyl, (e) $C_{1-4}$ alkyl which is substituted with pyridyl, oxypyridyl, carboxy, amino or tert-butoxycarbonylamino, (f) $C_{2-4}$ alkenyl which is substituted with pyridyl or oxypyridyl,
(g) phenyl which may be optionally substituted with a group selected from hydroxy, carboxy, ethoxycarbonyl, halogen, a $C_{1-4}$ alkyl which may be optionally substituted piperidinyl, pyrrolidinyl, amino, halogen or tert-butoxycarbonylamino and amino which may be optionally substituted with one or two $C_{1-4}$ alkyl or tert-butoycarbonyl,
(h) cyclohexyl which is substituted with amino or tert-butoxycarbonylamino,
(i) pyrazinyl and
(j) quinolyl.

2. The benzyloxypropylamine derivative according to claim 1, wherein $R_{1a}$ and $R_{1b}$ are trifluoromethyl substituents.

3. The benzyloxypropylamine derivative according to claim 1, wherein $R_{1a}$ and $R_{1b}$ are trifluoromethyl substituents located at the 3- and 5-positions of a benzyl group on the benzyloxypropylamine derivative represented by formula (I).

4. The benzyloxypropylamine derivative according to claim 3, wherein $R_2$ is phenyl.

5. The benzyloxypropylamine derivative according to claim 3, wherein $R_2$ is fluorophenyl.

6. The benzyloxypropylamine derivative according to claim 4, wherein $R_3$ is hydrogen.

7. The benzyloxypropylamine derivative according to claim 4, wherein $R_3$ is methyl.

8. N-[3-(3,5-bis(trifluoromethyl)benzyloxy)-2-(4-fluorophenyl)propyl]-1-oxyisonicotinic acid amide or a pharmaceutically acceptable salt thereof.

9. A pharmaceutical agent containing the benzyloxypropylamine derivative or a pharmaceutically acceptable salt thereof according to claim 1 as an effective ingredient.

10. The pharmaceutical agent according to claim 9, wherein said agent is an anti-inflammatory agent, an agent for allergic diseases, an analgesic, an antiemetic, an agent for irritable bowel syndrome, an agent for skin diseases, an agent for vasospastic diseases, an agent for cerebral ischemic diseases, an antidepressant, an anti-anxiety agent, an agent for autoimmune diseases, a muscle relaxant or an antispasmodic.

11. The pharmaceutical agent according to claim 10, wherein said agent is an antiemetic.

12. The benzyloxypropylamine derivative according to claim 5, wherein $R_3$ is hydrogen.

13. The benzyloxypropylamine derivative according to claim 5, wherein $R_3$ is methyl.

14. A pharmaceutical agent containing the benzyloxypropylamine derivative or a pharmaceutically acceptable salt thereof according to claim 2 as an effective ingredient.

15. A pharmaceutical agent containing the benzyloxypropylamine derivative or a pharmaceutically acceptable salt thereof according to claim 3 as an effective ingredient.

16. A pharmaceutical agent containing the benzyloxypropylamine derivative or a pharmaceutically acceptable salt thereof according to claim 4 as an effective ingredient.

17. A pharmaceutical agent containing the benzyloxypropylamine derivative or a pharmaceutically acceptable salt thereof according to claim 5 as an effective ingredient.

18. A pharmaceutical agent containing the benzyloxypropylamine derivative or a pharmaceutically acceptable salt thereof according to claim 6 as an effective ingredient.

19. A pharmaceutical preparation comprising the benzyloxypropylamine derivative or a pharmaceutically acceptable salt thereof of claim 1 and a pharmaceutically acceptable carrier or diluent.

20. A pharmaceutical preparation comprising the N-[3-(3,5-bis(trifluoromethy)benzyloxy)-2-(4-fluorophenyl)propyl]-1-oxyisonicotinic acid amide or a pharmaceutically acceptable salt thereof of claim 8 and a pharmaceutically acceptable carrier or diluent.

* * * * *